US008017791B2

(12) United States Patent
Dutta

(10) Patent No.: US 8,017,791 B2
(45) Date of Patent: Sep. 13, 2011

(54) TRI-SUBSTITUTED 2-BENZHYDRYL-5-BENZYLAMINO-TETRAHYDRO-PYRAN-4-OL AND 6-BENZHYDRYL-4-BENZYLAMINO-TETRAHYDRO-PYRAN-3-OL ANALOGUES, AND NOVEL, 3,6-DISUBSTITUTED PYRAN DERIVATIVES

(75) Inventor: Aloke K. Dutta, Novi, MI (US)

(73) Assignee: Wayne State University, Detroit, MI (US)

( * ) Notice: Subject to any disclaimer, the term of this patent is extended or adjusted under 35 U.S.C. 154(b) by 383 days.

(21) Appl. No.: 12/050,040

(22) Filed: Mar. 17, 2008

(65) Prior Publication Data

US 2008/0167478 A1    Jul. 10, 2008

Related U.S. Application Data

(63) Continuation-in-part of application No. 11/330,972, filed on Jan. 12, 2006, now abandoned, which is a continuation-in-part of application No. PCT/US2005/012748, filed on Apr. 15, 2005, and a continuation-in-part of application No. 10/311,796, filed on Mar. 28, 2003, now Pat. No. 6,995,268.

(60) Provisional application No. 60/563,189, filed on Apr. 16, 2004.

(51) Int. Cl.
*C07D 207/09* (2006.01)
*C07D 307/14* (2006.01)

(52) U.S. Cl. ........................................ 548/566; 549/492

(58) Field of Classification Search .................... 549/492
See application file for complete search history.

(56) References Cited

U.S. PATENT DOCUMENTS

| 5,232,929 | A | 8/1993 | DeSai et al. |
| 5,300,499 | A | 4/1994 | Chow |
| 5,344,835 | A | 9/1994 | Alker et al. |

FOREIGN PATENT DOCUMENTS

| EP | 0217286 A2 | 4/1987 |
| EP | 0417698 A1 | 3/1991 |
| WO | 9850534 A1 | 11/1998 |
| WO | 9925686 | 5/1999 |

OTHER PUBLICATIONS

Derivative [online] retrieved from internet on Jun. 3, 2010. URL; http:///www.merriam-webster.com/dictionary/derivative.*
Prueksaritanont, et al. Toxicology and Applied Pharmacology 217 (2006) 143-152.*
[Pub1.pdf]: M.J. Kuhar, "Neurotransmitter Uptake: A Tool in Identifying Neurotransmitter Specific Pathways," Life Sci., 13, 1623-34, 1973.
[Pub2.pdf]: M.E.A. Reith et al., "Strucural Requirements for Cocaine Congeners to Interact with Dopamine and Serotonin Uptake Sites in Mouse Brain and to Induced Stereotyped Behavior," Biochem. Pharmacol., 1986, 35, 1123-1129.
[Pub3.pdf]: M.C. Ritz et al., "Cocaine Inhibition of Ligand Binding at Dopamine, Norpinephrine and Serotonin Transporters: A Structure-Activity Study," Life. Sci., 1990, 46, 635-645.
[Pub4.pdf]: M.C. Ritz et al., "Cocaine Receptors on Dopamine Transporters are Related to Self-Administration of Cocaine," Science, 1987, 237, 1219-1223.
[Pub5.pdf]: B. Giros et al., "Hyperlocomotion and Indifference to Cocaine and Amphetamine in Mice Lacking the Dopamine Transporter," Nature, 1996, 379, 606-612.
[Pub6.]: B. Giros et al., "Hyperlocomotion and Indifference to Cocaine and Amphetamine in Mice Lacking the Dopamine Transporter," Nature, 1996, 379, 606-612.
[Pub7.pdf]: J.M. Maloteaux et al., Eur. J. Pharm., 1988, 156, 331-340.
[Pub8.pdf]: H.B. Niznik et al., Arch. Biochem. Biophys., 1990, 276, 424-432.
[Pub9.pdf]: K.M. Johnson, "Phencyclidine: Behavioral and Biochemical Evidence Supporting a Role for Dopamine," Fed. Proc., 1983, 42, 2579-3583.
[Pub10.pdf]: E.D. French et al., "Phencyclidine Binding Sites in the Nucleus Accumbens and Phencyclidine-Induced Hyperactivity are Decreased Following Legions of the Mesolimbic Dopamine System," Eur. J. Pharmacol., 1985, 116, 1-9.
[Pub11.pdf]: H. Kinemuchi et al., "The Neurotoxicity of 1-methyl-4-phenyl-1,2,3,6-tetrahydropyridine (MPTP) and its Relevance to Parkinson's Disease," Neurochem. Int., 1987, 11, 359-373.
[Pub12.pdf]: F.I. Carroll et al., "Cocaine Receptor: Biochemical Characterization and Structure-Activity Relationship of Cocaine Analogues at the Dopamine Transporter," J. Med. Chem., 1992, 35, 969-981.
[Pub13.pdf]: R.A. Millius et al., "Synthesis and Receptor Binding of N-substituted Tropane Derivatives," "High Affinity Ligands for Cocaine Receptor," J. Med. Chem., 1991, 34, 1728-1731.
[Pub14.pdf]: I. Chaudieu et al., "Role of the Aromatic Group in the Inhibition of Phencyclidine Binding and Dopamine Uptake by PCP Analogs," Pharmacol. Biochem. Behav., 1989, 32, 699-705.
[Pub15.pdf]: J. Vignon et al., "[3H]N-[1(2-Benzo(b)thienyl)cyclohexyl]piperidine([3H]BTCP): A New Phencyclidine Analog Selective for the Dopamine Uptake Complex," Eur. J. Pharmacol., 1988, 148, 427-436.
[Pub16.pdf]: P.H. Anderson, "Biochemical and Pharmacological Characterization of [3H]GBR 12935 Binding in Vitro to Rat Striatal Membranes: Labeling of the Dopamine Uptake Complex," J. Neurochem., 1987, 48, 1887-1896. [Pub17.pdf]: P.H. Anderson, "The Dopamine Uptake Inhibitor GBR 12909: Selectivity and Molecular Mechanism of Action," Eur. J. Pharmacol., 1989, 166, 493-504.
[Pub18.pdf]: R.B. Kolhatkar et al., "Interaction of cis-(6-Benzhydrylpiperidin-3-y)benzylamine Analogues with Monoamine Transporters: Structure-Activity Relationship Study of Structurally Constrained 3,6-Disubstituted Piperidine Analogues of (2,2-Diphenylethyl)-[1-(4-fluorobenzyl)piperidin-4-ylmethyl]amine," J. Med. Chem. 2003, 46, 2205-2215.
[Pub19.pdf]: C. DeVries et al., "Heteroaromatic Analogs of 1-2[2-(diphenylmethoxy{ethyl]- and 1-[2[bis(4-fluorophenyl) methoxy]ethyl]-4-(3-phenylpropyl)piperazines (GBR 12935 and GBR 12909) as High-Affinity Dopamine Reuptake Inhibitors," J. Med. Chem., 1997, 40, 705-716.

(Continued)

*Primary Examiner* — Shawquia Young
(74) *Attorney, Agent, or Firm* — Brooks Kushman P.C.

(57) ABSTRACT

Novel 3,6-disubstituted pyrans, optionally with a further substituent at the 4-position, are monoamine reuptake inhibitors with activity profiles of anti-depressants.

3 Claims, 19 Drawing Sheets

OTHER PUBLICATIONS

[Pub20.pdf]: D. Matecka et al., Development of Novel, Potent, and Selective Dopamine Reuptake Inhibitors Through Alteration of the Piperazine Ring of 1-[2-(diphenylmethoxy)ethyl]- and 1[2-[bis(4-fluorophenyl)methoxy]ethyl]-4-(3-phenylpropyl)piperazines (GBR 12935 and GBR 12909), J. Med. Chem., 1996, 39, 4704-4716.

[Pub21.pdf]: R.B. Rothman, "Tight Binding Dopamine Reuptake Inhibitors as Cocaine Antagonists," FEBS Lett., 1989, 257, 341-344.

[Pub22.pdf]: J.R. Glowa et al., "The Effects of GBR 12909 on Responding of Rhesus Monkeys Maintained Under Schedules of Cocaine- and Food-Delivery," NIDA. Res. Monogr., 1994, 141, 12.

[Pub23.pdf]: A.K. Dutta et al., "Structure-Activity Relationship Studies of Novel 4[2-[Bis(4-fluorophenyl)methoxy]ethy]-1-(3-phenylpropyl)piperidine Analogs: Synthesis and Biological Evaluation of the Dopamine and Serotonin Transporter Sites," J. Med. Chem., 1996, 39, 749-756.

[Pub24.pdf]: A.K. Dutta et al., "Highly Selective, Novel Analogs of 4-[2-(diphenylmethoxy)ethyl]-1-benzylpiperidine for the Dopamine Transporter: Effect of Different Aromatic Substitutions on their Affinity and Selectivity," J. Med. Chem., 1997, 40, 35-43.

[Pub25.pdf]: A.K. Dutta et al., "Potent and Selective Ligands for the Dopamine Transporter (DATE): Structure-Activity Relationship Studies of Novel 4-[2-(diphenylmethoxy)ethyl]-1-(3-phenylpropyl)piperidine Analogs," J. Med. Chem., 1998, 41, 699-756.

[Pub26.pdf]: Derwent Abstract, Eur. J. Nucl. Med., (1999), 26(4), 342-347, "In Vivo Imaging of Serotonin Transporters with [99mTc] TRODAT-1 in Nonhuman Primates" [AN 1999:196775].

[Pub27.pdf]: A.K. Dutta et al., "Tolerance in the Replacement of the Benzhydrylic O Atom in 4-[2-(Diphenylmethoxy)ethyl]-1-benzylpiperidine Derivatives by an N. Atom: Development of New-Generation Potent and Selective N-Analogue Molecules for the Dopamine Transporter," J. Med. Chem., vol. 41, No. 17, pp. 3293-3297.

[Pub28.pdf]: Database on STN CASDATA (Columbus, Ohio, USA) Abstract No. 132:119356, Hoepping et al., "Synthesis and biological evaluation of two novel DAT binding technetium complexes" Bioorg. Med. Chem. Lett. (1999) vol. 9, No. 22, pp. 3211-3216.

[Pub29.pdf]: F. Ivy Carroll et al., "Cocaine and 3B-(4'-Substituted phenyl) tropane-2B-carboxylic Acid Ester and Amide Analogues. New High-Affinity and Selective Compounds for the Dopamine Transporter," J. Med. Chem. 1995, 38, 379-388.

[Pub30.pdf]: Amara, S. G., Kuhan, M. J. Neurotransmitter transporters: recent progress. Annu. Rev. Neurosci, 1993, 16, 73-93.

[Pub31.pdf]: Rudnick, G. Mechanisms of biogenic amine neurotransmitter transporters. In neurotransmitter transporters: Structure and function; Reith, M. E. A., Eds.; Human Press: Totowa, N J, second edition, 381-432, 2002.

[Pub32.pdf]: Rudnick, G., Wall, S. C. The molecular mechanism of ectasy [3,4-methylenedioxymethamphetamine(MDMA)]-serotonin transporters are targets for MDMA induced serotonin release. Proc. Natl. Acad. Sci. USA, 1992, 89, 1817-1821.

[Pub33.pdf]: Steele, T., Nichols, D., Yim, G. Stereochemical effects of 3,4-methylenedioxymethamphetamine (MDMA) and related amphetamine derivatives on inhibition of uptake of [3H]monoamine into synaptosomes from different regions of rat brain. Biochem. Pharmacol. 1987, 36, 2297-2303.

[Pub34.pdf]: Kuhar, M.J., Ritz, M.C., Boja, J.W. The dopamine hypothesis of the reinforcing properties of cocaine. Trends. Neurosci. 1991, 14, 299-302.

[Pub35.pdf]: Tatsumi, M., Groshan, K., Blakely, R. Pharmacological profile of antidepressants and related compounds at human monoamine transporters. Eur. J. Pharmacol. 1997, 340, 249-258.

[Pub36.pdf]: Richelson, E. Interactions of antidepressants with neurotransmitter transporters and receptors and their clinical relevance. J. Clin. Psychiatry. 2003, 64, 5-12.

[Pub37.pdf]: Koch, S., Hemrick-Luecke, S., Thompson, L., Evans, D., Threlkeld, P., Nelson, D., Perry, K., Bymaster, F. Comparison of effects of dual transporter inhibitors on monoamine transporters and extracellular levels in rats. Neuropharmacology. 2003, 45, 935-944.

[Pub38.pdf]: Nemeroff, C. B. Psychopharmacology of affective disorders in the 21= century. Biol. Psychiatry. 44, 517-525, 1998.

[Pub39.pdf]: Iverson, L. Neurotransmitter transporters: fruitful targets for CNS drug discovery. Mol. Psychiatry. 5, 357-362, 2000.

[Pub40.pdf]: Schloss, P., Williams, D. C. The serotonin transporter: a primary target for antidepressant drugs. J. Psychopharmacol. 12, 115-121, 1998.

[Pub41.pdf]: Feighner, J. P. Mechanism of action of antidepressant medications. J. Clin. Psychiatry. 60, 4-11, 1999.

[Pub42.pdf]: Pinder, R. M., Wieringa, J. H. Third-generation antidepressants. Med. Res. Rev. 13, 259-325, 1993.

[Pub43.pdf]: Barbey, J. T., Roose, S. P. SSRI safety in overdose. J. Clin. Psychiatry. 59 Suppl 15:42-8, 1998.

[Pub44.pdf]: Dutta, A.K., Davis, M.C., Reith, M. E. A. Rational Design and synthesis of novel conformationally constrained 2,5-disubstituted cis- and tras-piperidine derivatives exhibiting differential activity for the dopamine transporter. Bioorg. Med. Lett. 2001, 11, 2337-2340.

[Pub45.pdf]: Kolhatkar R.B., Ghorai S.K., George C, Reith M. E. A, Dutta A K. Interaction of cis-(6-benzhydrylpiperidin-3-yl)-benzylamine analogs with monoamine transporters: Structure Activity Relationship study of structurally constrained 3,6-disubstituted piperidine analogs of (2,2-diphenylethyl)-[1-(4-fluorobenzyl)piperidine-4-ylmethyl]amine. J. Med. Chem. 2003, 46, 2205-2215.

[Pub46.pdf]: Zhang S, Reith M E A, Dutta A K. Design, synthesis, and activity of novel cis- and trans-3,6-disubstituted pyran biomimetics of 3,6-disubstituted piperidine as potential ligands for the dopamine transporter. Bioorg. Med. Chem. Lett. 13, 1591-1595, 2003.

[Pub47.pdf]: Zhang, S., Zhen, J., Reith, M.E.A., Dutta, A.K., "Structural requirements for 2,4- and 3,6-disubstituted pyran biomimetics of cis-(6-benzhydryl-piperdin-3-yl)-benzylamine compounds to interact with monoamine transporters," Bioorganic Medicinal Chemistry, 2004, 12, 6301-6315.

[Pub48.pdf]: J. Langston et al., "MPTP: Current Concepts and Controversies," Clin. Neuropharmac., 1986, 9, 485-507.

[Pub49.pdf]: Cookson, "J. Side Effects of Antidepressants," Br. J. Psychiatry, 20, 20-24, 1993.

[Pub50.pdf]: A.K. Dutta et al., "Positional Importance of the Nitrogen Atom in Novel Piperidine Analogs of GBR 12909: Affinity and Selectivity for the Dopamine Transporter," Med. Chem. Res., 1993, 3, 209-222.

[Pub51.pdf]: Shoemaker, H., et al., Naunyn Schmiedebergs Arch. Pharmacol., 1985, 329, 227-235.

[Pub52.pdf]: Baker Botts, "In Prints—Reach-Through Claims," http://www.bakerbotts.com/news/printpage.asp?pubid=19221417 (2 pgs.).

[Pub53.pdf]: Gourley, D.R.H., "Biological Responses to Drugs," Medicinal Chemistry, 3rd Ed., Part I, p. 25.

[Pub54.pdf]: Zhang, S., et al., "Design, Synthesis, and Preliminary SAR Study of 3- and 6-Side Chain Extended Tetrahydro-Pyran Analogues of cis- and trans-(6-benzhydryl-piperidin-3-yl)-benzylamine," Bioorg. Med. Chem. 14, 3953-3966, 2006.

[Pub55.pdf]: Zhang, S., et al., "Design, Synthesis, and Preliminary SAR Study of 3- and 6-Side Chain Extended Tetrahydro-Pyran Analogues of cis- and trans-(6-benzhydryl-piperidin-3-yl)-benzylamine," Bioorg. Med. Chem. 14, 3953-3966, 2006.

[Pub56.pdf]: Zhang, S., et al., "Discovery of Novel tri-substituted Asymmetric Pyran Derivatives, (2S, 4R, 5R)-2-benzhydryl-5-benzylamino-tetrahyddropyran-4-ol, Exhibiting Stereospecific Manner," J. Med. Chem. 48, 4962-4971, 2005.

English Abstract of JP Publ. No. 09-249566, Sep. 22, 1997 (2 pgs.).

Prof. Arthur Cammers, University of Kentucky Outline Synthetic Organic Chemistry 535 Session Jun. 2007, online "http://www.chem.uky.edu/courses/che535/AC/2007.1S/06-2007-S-CHE535.pdf", p. 57-65, Oct. 6, 2007.

Dalpozzo, R. et al., "Bartoli Indole Synthesis," Current Organic Chemistry, 2005, 9, 163-178.

Li, Jie Jack, "Name Reactions: A Collection of Detailed Reaction Mechanisms," Third Expanded Edition, Springer 2006, pp. 271-272.

Knochel, Paul et al., "Highly Functionalized Organomagnesium Reagents Prepared Through Haolen-Metal Exchange," Angew. Chem Int. Ed. 2003, 42, 4302-4320.

Hutchins, R.O. et al., "Selective Reductive Displacement of Alkyl Halides and Sulfonate Esters with Cyanoborohydride Reagents in Hexamethylphosphoramide," J. Org. Chem. 1977, 42, pp. 82-91.

Dorwald, F.A., "Side Reactions in Organic Synthesis," 2005, Wiley: VCH, Weinheim p. IX of Preface.

Singh, S., "Chemistry, Design, and Structure—Activity Relationship of Cocaine Antagonists," Chem. Rev. 2000, 100, pp. 925-1024.

Beasley, C.M., Holman, S.L., Potvin, J.H., "Fluoxetine compared with imipramine in the treatment of inpatient depression. A multicenter trial." Ann. Clin. Psychiatry. 5, 199-207, 1993.

K. Ghorai et al., "High Affinity Hydroxypiperidine Analogues of 4-(2-Benzhydryloxyethyl)-1-(4-fluorobenzyl)piperidine for the Dopamine Transporter: Stereospecific Interactions in Vitro and in Vivo," J. of Med. Chem., v. 46, Apr. 3, 2003, p. 1222.

Goldstein, B.J., Goodnick, P.J., Selective serotonin reuptake inhibitors in the treatment of affective disorders-III. Tolerability, safety and pharmacoeconomics. J. Psychopharmacol. 12(3 Suppl B): 55-87, 1998.

* cited by examiner (a) oxalyl chloride, DMSO, Et$_3$N/CH$_2$Cl$_2$ (b) 4-fluorobenzylamine, AcOH, NaCNBH$_3$/ClCH$_2$CH$_2$Cl (a) SnCl$_2$·2H$_2$O/EtOH/EtOAc (b) 4-fluorophenylacetyl chloride, Et$_3$N/CH$_2$Cl$_2$ (d) NaBH$_4$, BF$_3$·Et$_2$O/THF

Scheme 1

(R,R)-(-)-N,N'-Bis(3,5-di-tert-butylsalicylidene)-1,2-cyclohexanediaminocobalt a) methyldiphenylphosphonium bromide/BuLi/THF b) mCPBA/CH$_2$Cl$_2$
c) Jacobsen's catalyst/H$_2$O d) TPP/DEAD/benzene

Scheme 3 a) vinyl magnesium bromide/CuI/THF b) NaH/allyl bromide/DMF c) Grubbs' catalyst/benzene
d) mCPBA/CH$_2$Cl$_2$ e) amine/ethanol a) NaN$_3$/NH$_4$Cl/THF-H$_2$O (8:1), 80°C, overnight. b) H$_2$/Pd-C, MeOH, 4 hr. c) aldehyde/AcOH/NaCNBH$_3$, ClCH$_2$CH$_2$Cl, room temperature, 4 hr

Scheme 8

TRI-SUBSTITUTED 2-BENZHYDRYL-5-BENZYLAMINO-TETRAHYDRO-PYRAN-4-OL AND 6-BENZHYDRYL-4-BENZYLAMINO-TETRAHYDRO-PYRAN-3-OL ANALOGUES, AND NOVEL, 3,6-DISUBSTITUTED PYRAN DERIVATIVES

CROSS-REFERENCE TO RELATED APPLICATION

This application is a continuation-in-part of U.S. Ser. No. 11/330,972 filed Jan. 12, 2006, which is a continuation-in-part of International Patent Application No. PCT/US2005/012748, filed Apr. 15, 2005 and published in English, which claims the benefit of U.S. Provisional Application Ser. No. 60/563,189, filed Apr. 16, 2004. This application is also a continuation-in-part of U.S. application Ser. No. 10/311,796, filed Mar. 28, 2003. The entire disclosure of each of these applications is hereby incorporated by reference.

BACKGROUND OF THE INVENTION

1. Field of the Invention

The invention pertains to pharmacologically active 3,6-disubstituted pyran compounds and similar compounds having additional substitution on the pyran ring. The compounds show high activity at monoamine transporters, and thus can be used to alter reuptake of monoamines in treatment of numerous diseases in mammalian species for which alteration of the monoamine transport system is indicated.

2. Background Art

The monoamine transporters terminate the action of released biogenic amines such as dopamine (DA), norepinephrine (NE) and serotonin (5-HT) in the central nervous system (CNS) and are known as dopamine transporter (DAT), norepinephrine transporter (NET) and serotonin transporter (SERT), respectively. These transporters play a vital role in maintaining the extracellular concentration of biogenic amine neurotransmitters. Drugs binding to the DAT are typically regarded as stimulants. Cocaine- and amphetamine-related compounds are known to produce their action by binding to both DAT and SERT with cocaine acting as a blocker and amphetamine as a substrate. On the other hand, drugs binding to the SERT and NET are known to produce, among other effects, potent antidepressant activity.[8-10]

Major depression disorder is a significant health problem, and behind cardiovascular disease, depression is considered as the second most debilitating disease in the world. Unipolar depression is ranked number 1 before all other somatic and psychiatric illness. It is believed that more than 20% of individuals suffer from a depressive episode at least once in their lifetime. Depression is potentially fatal since many people suffering from depression contemplate suicide and other life threatening acts.

Selective monoamine uptake inhibitors have been implicated in the treatment of depression. In these classes specifically, serotonin and norepinephrine transporter blockers have been used in therapy for depression. Antidepressants are thought to elicit their therapeutic effects by increasing synaptic concentrations of serotonin and norepinephrine in the synapse. Earlier developed tricyclic antidepressants acted by enhancing both serotonin and norepinephrine transmissions. However, due to their non-specific interactions with the other CNS receptors, they exhibited toxic side effects which have limited their clinical use. Development of selective serotonin reuptake inhibitors (SSRI) alleviated many side effects exhibited by traditional tricyclic antidepressants and thus have proven to be more effective. However, the delayed onset action of SSRI sometime proved to have fatal consequences for patients afflicted with manic depression and in need of immediate help. SSRIs also have been implicated in number of other side effects which include insomnia, sexual dysfunction and nausea, etc. More recently, SSRIs have been implicated in suicide risk in adolescent population who were medicated with these drugs, raising some serious questions on the safety of SSRI. Lately, serotonin and norepinephrine dual uptake inhibitors have proven to be more efficacious in that regard. Fast onset of action associated with serotonin norepinephrine reuptake inhibitors (SNRI) was found to be more desirable as there is a pressing need for more faster acting antidepressant agents with reduced undesirable side effects.

SUMMARY OF THE INVENTION

It has been surprisingly discovered that 3,6-disubstituted pyrans as hereinafter defined, and in particular 3,6-disubstituted pyrans also containing a further substituent on the pyran ring, exhibit potent activity on monoamine transport systems, and are thus useful in probing the effects of binding to monoamine transport systems and the corresponding relationships to various afflictions affecting the CNS, or as a treatment for various CNS-related disorders in which the monoamine transport system is implicated. It has been surprisingly and unexpectedly discovered that the novel 3,6-disubstituted and 2,5,-4-trisubstituted pyran molecules of the present invention operate as powerful blockers for monoamine transporters.

DETAILED DESCRIPTION OF THE PREFERRED EMBODIMENTS 3,6-disubstituted pyran derivatives have been discovered to be powerful agents targeting monoamine transporter systems. The pyran analogs are the bioisosteric versions of earlier structurally constrained cis-3,6-disubstituted piperidine derivatives which exhibited potent and selective affinities toward DAT in a stereo-selective manner, for Example compound 1b as shown below. The pyran series of compounds yielded results which indicate that the mode of interactions of these pyran molecules with monoamine transporters is different from their piperidine counterparts even though similar stereoselectivity, cis-configuration of most active piperidine 1a and pyran 1b, was maintained for optimal DAT activity in both cases.

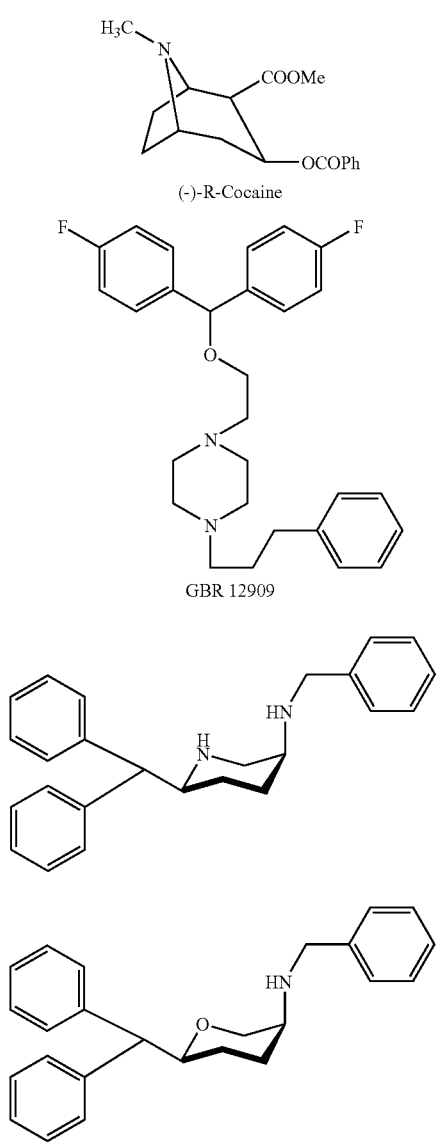

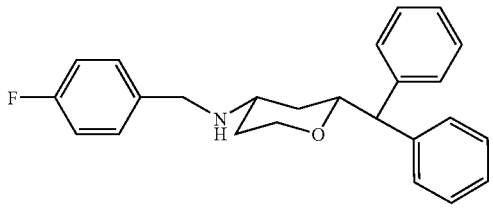

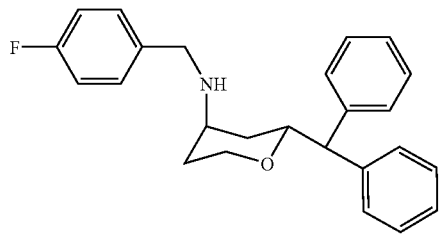

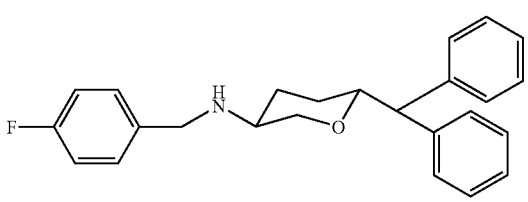

Figure 1:
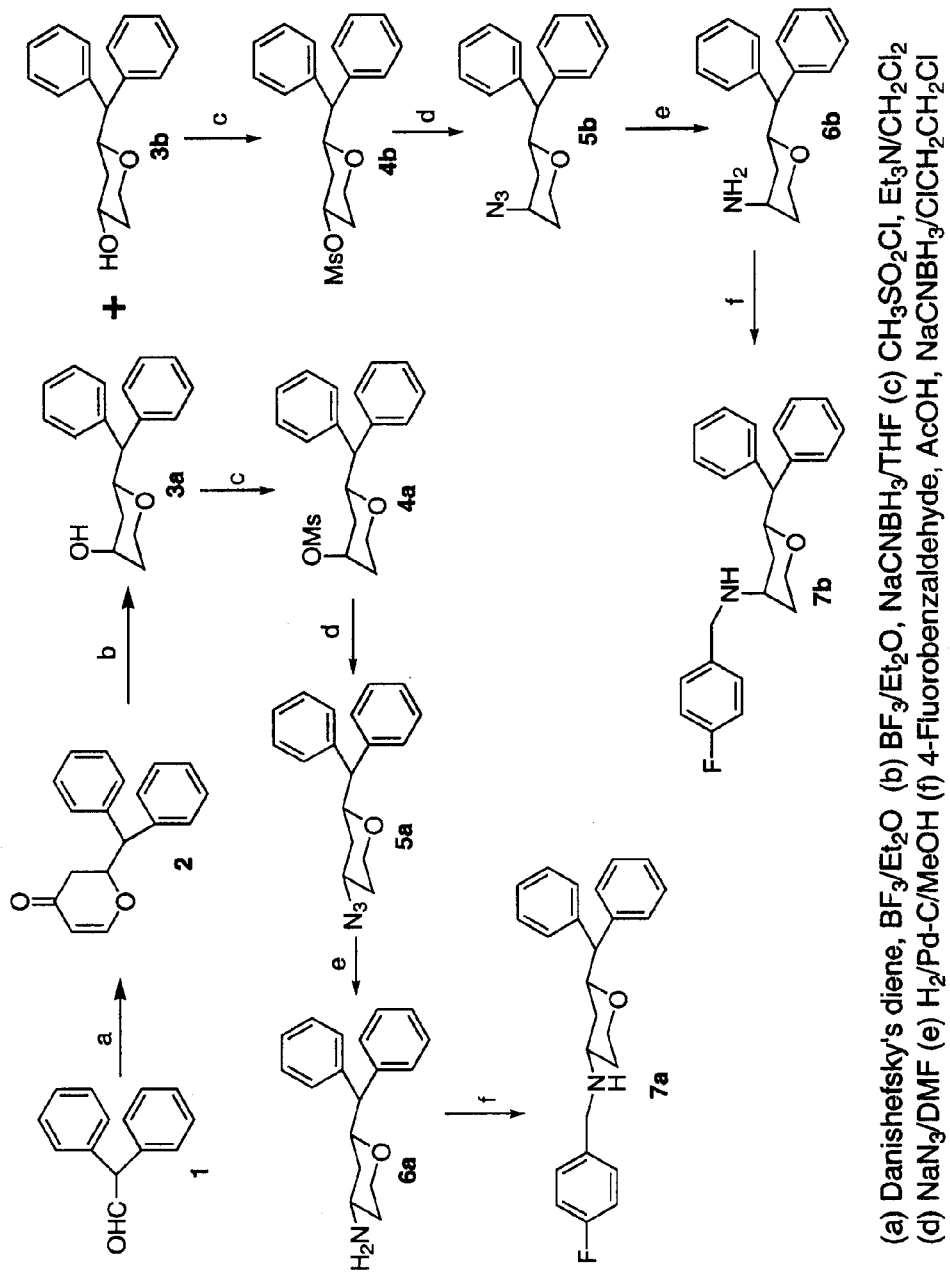
FIG. 1 provides a scheme for the preparation of compounds an embodiment of the present invention.
Figure 2:
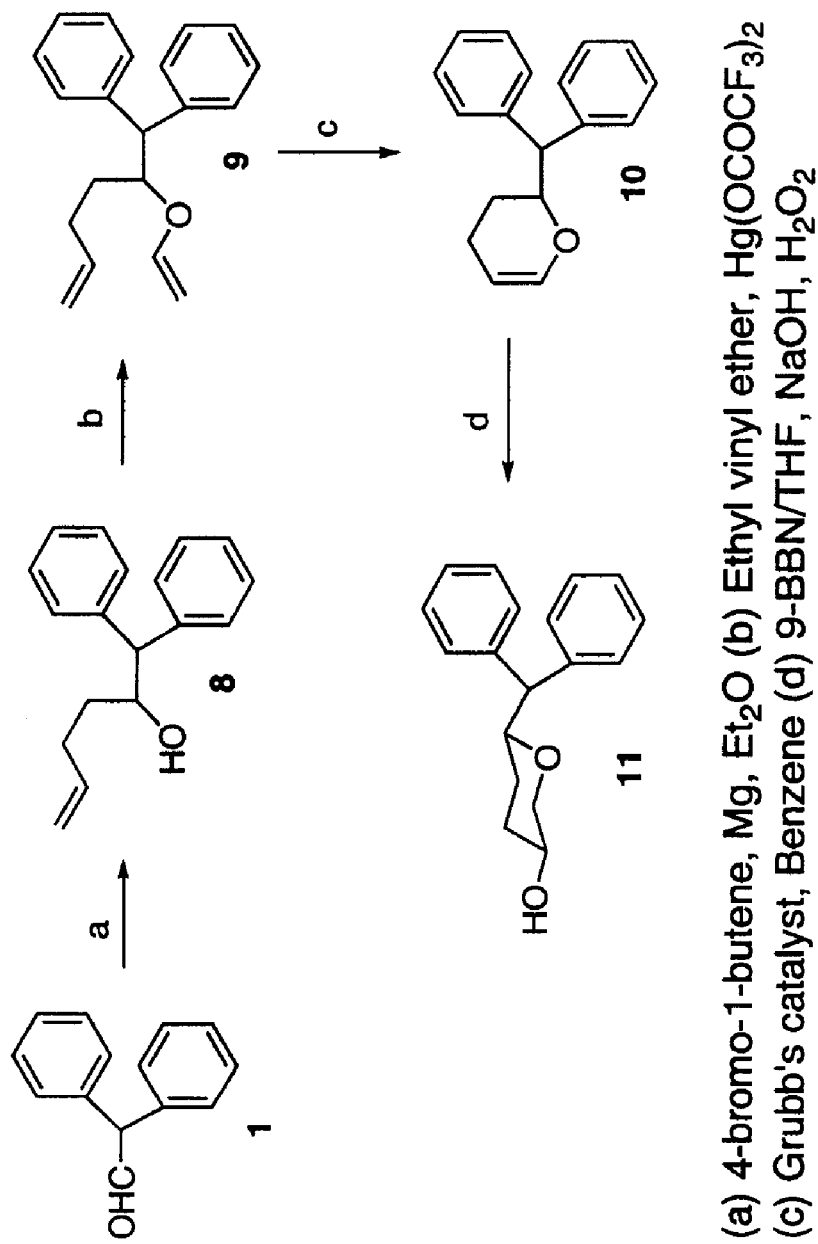
FIG. 2 provides a scheme for the preparation of compounds an embodiment of the present invention.
Figure 3:
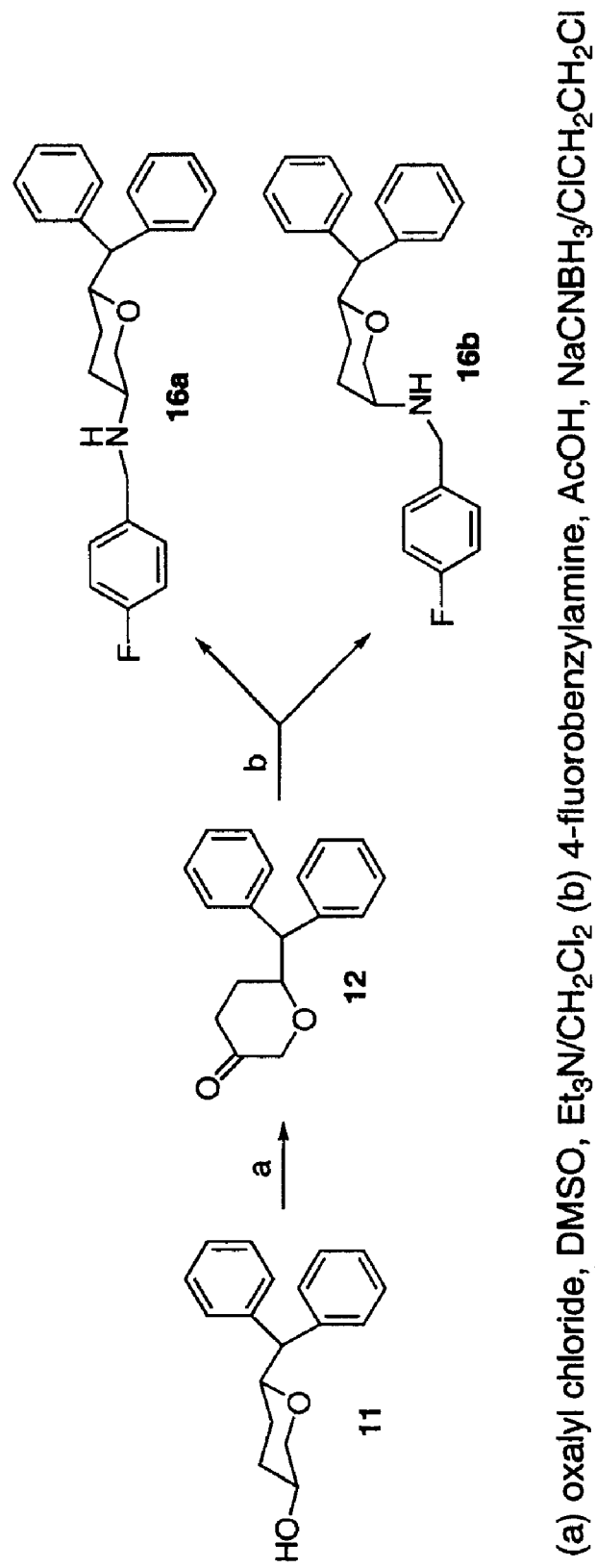
FIG. 3 provides a scheme for the preparation of compounds an embodiment of the present invention.
Figure 4:
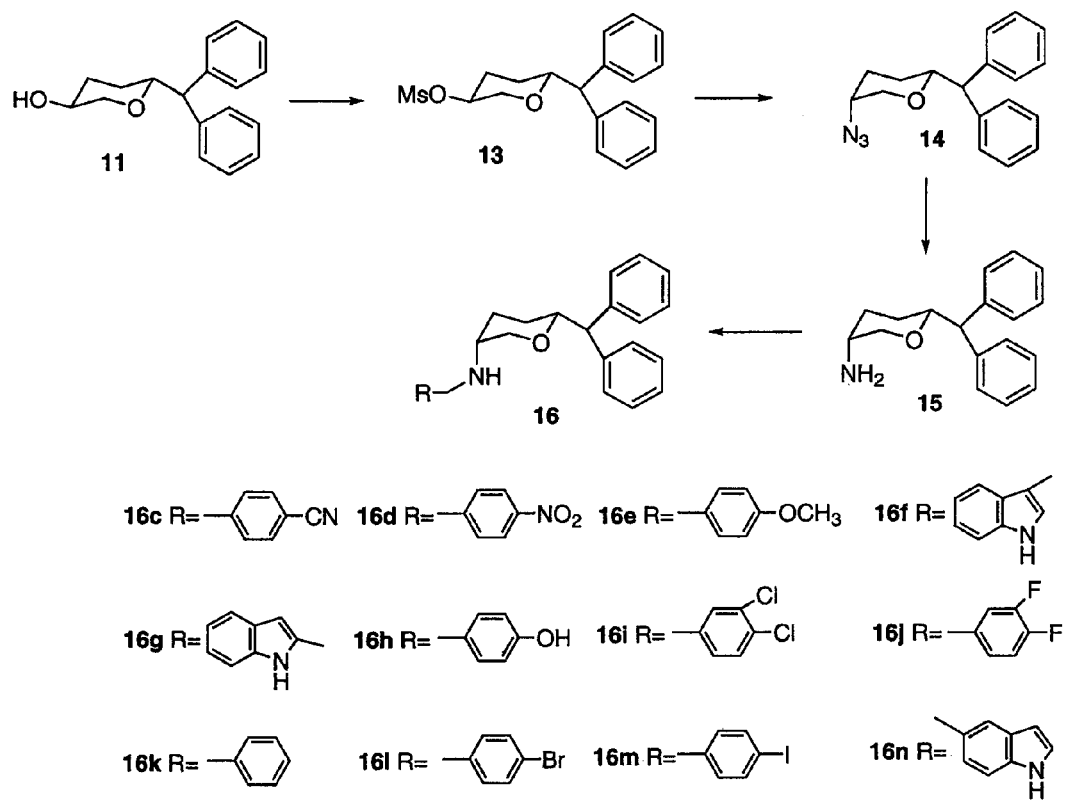
FIG. 4 provides a scheme for the preparation of compounds an embodiment of the present invention.
Figure 5:
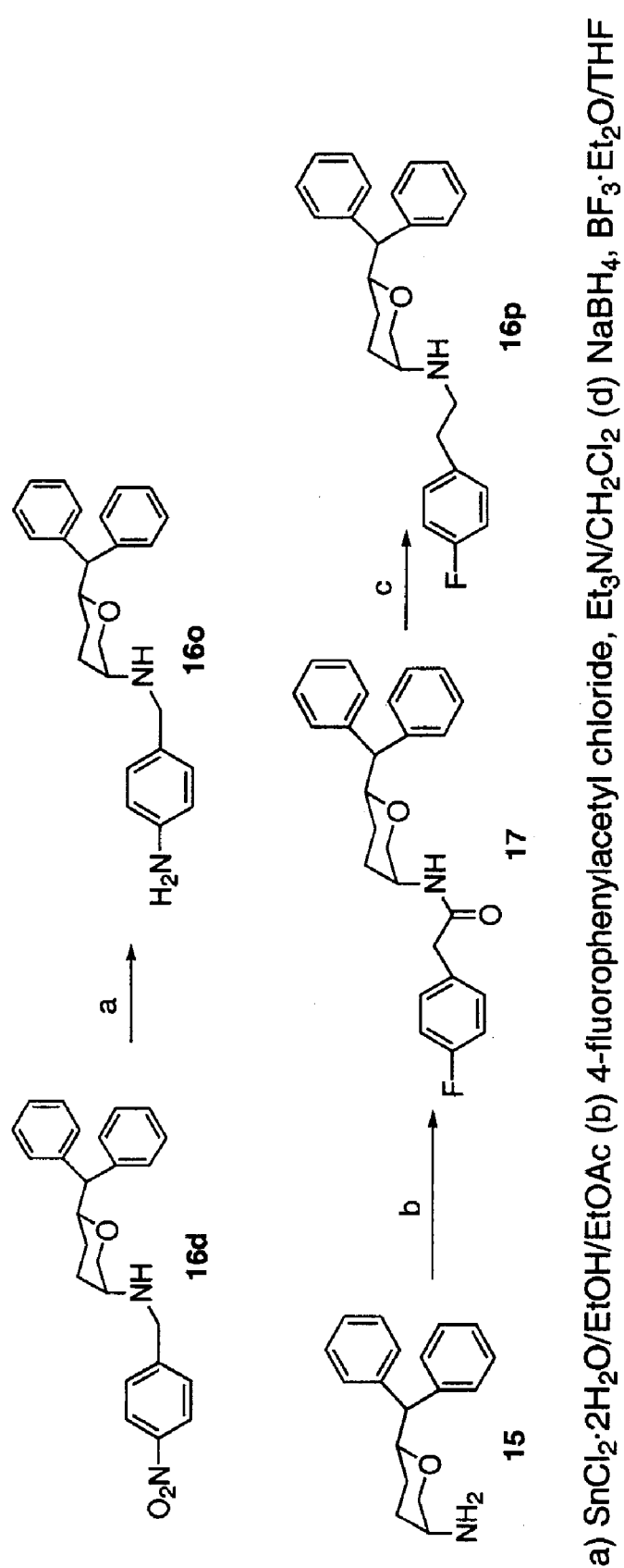
FIG. 5 provides a scheme for the preparation of compounds an embodiment of the present invention.
Figure 6:
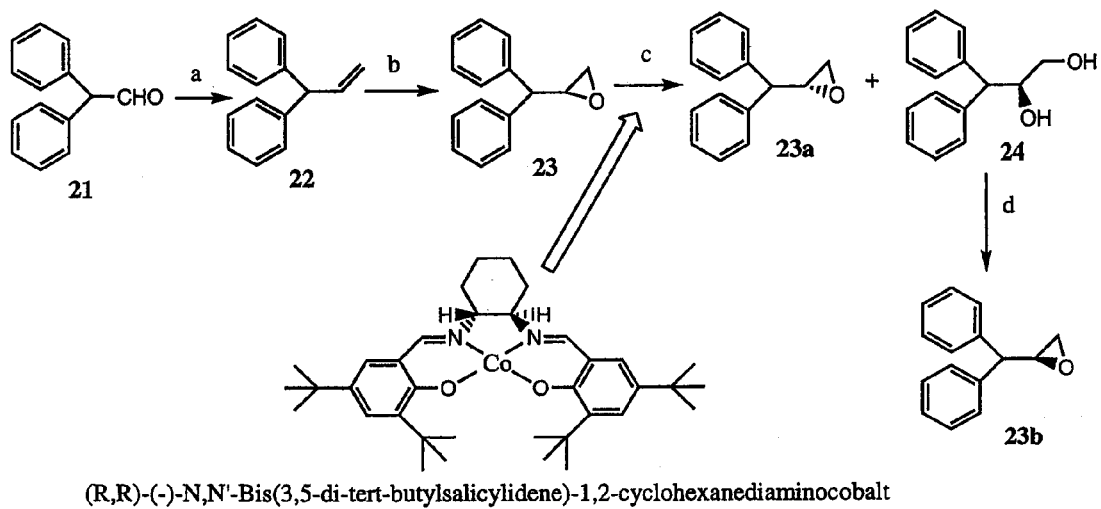
FIG. 6 provides a scheme for the preparation of compounds an embodiment of the present invention.
Figure 7:
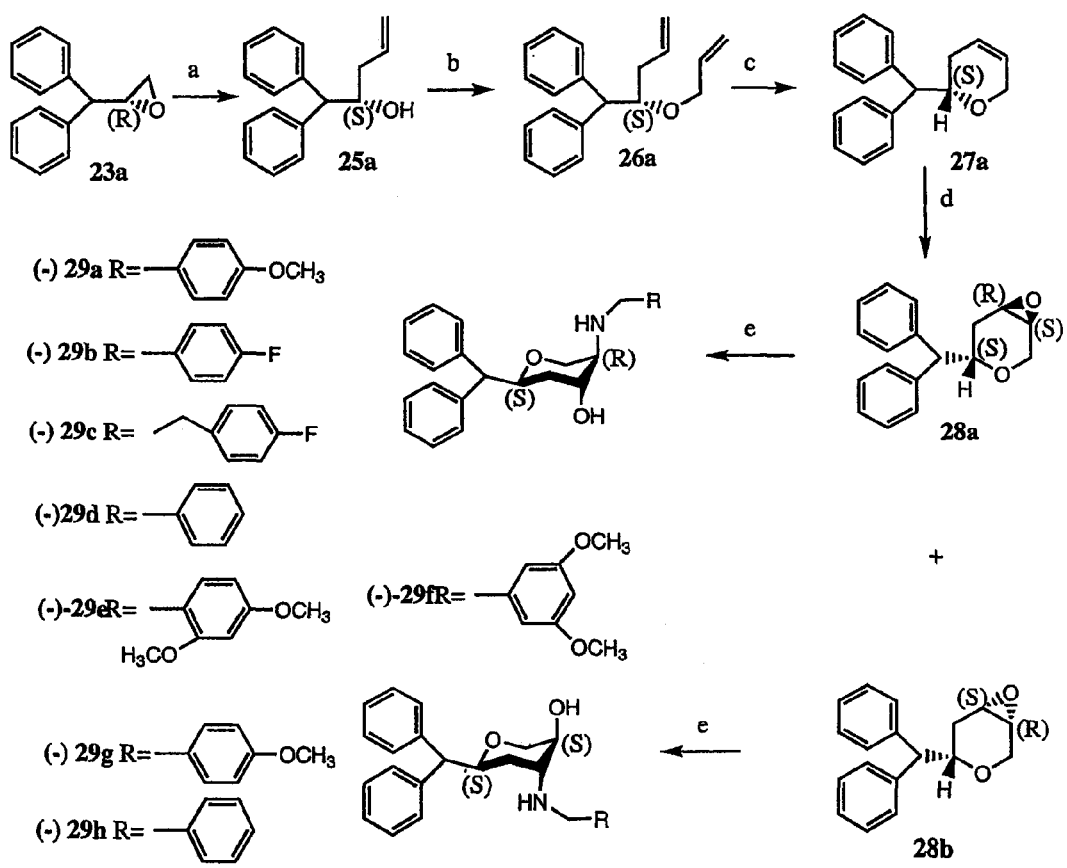
FIG. 7 provides a scheme for the preparation of compounds an embodiment of the present invention.
Figure 8:
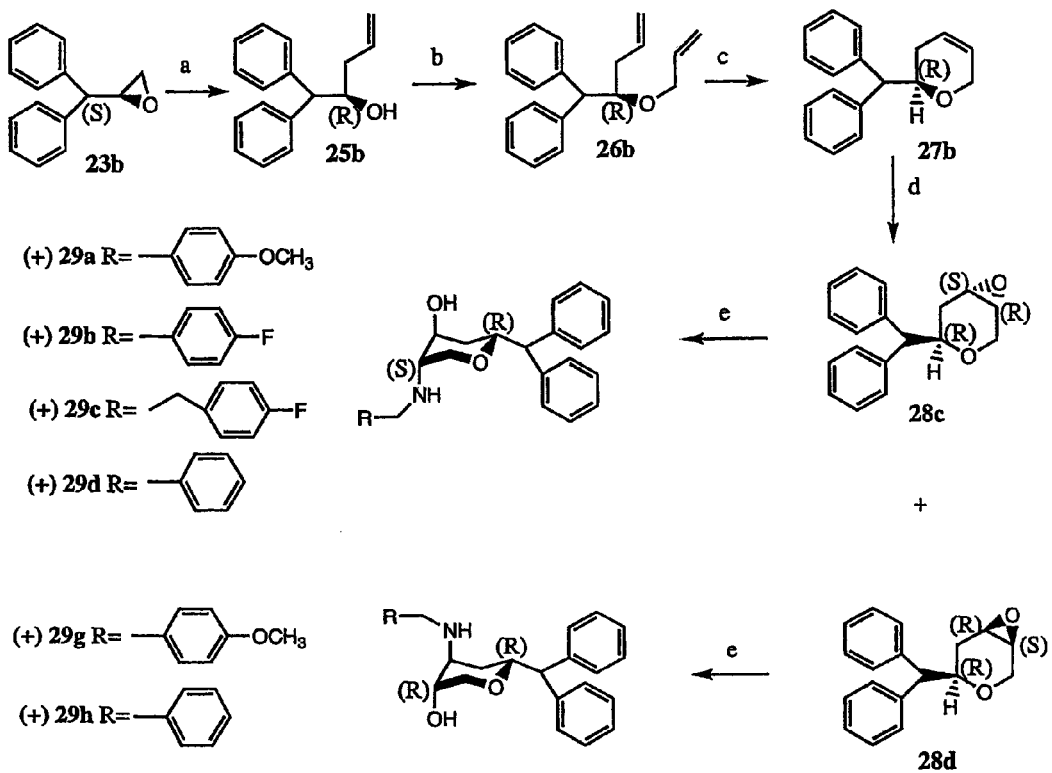
FIG. 8 provides a scheme for the preparation of compounds an embodiment of the present invention.
Figure 9:
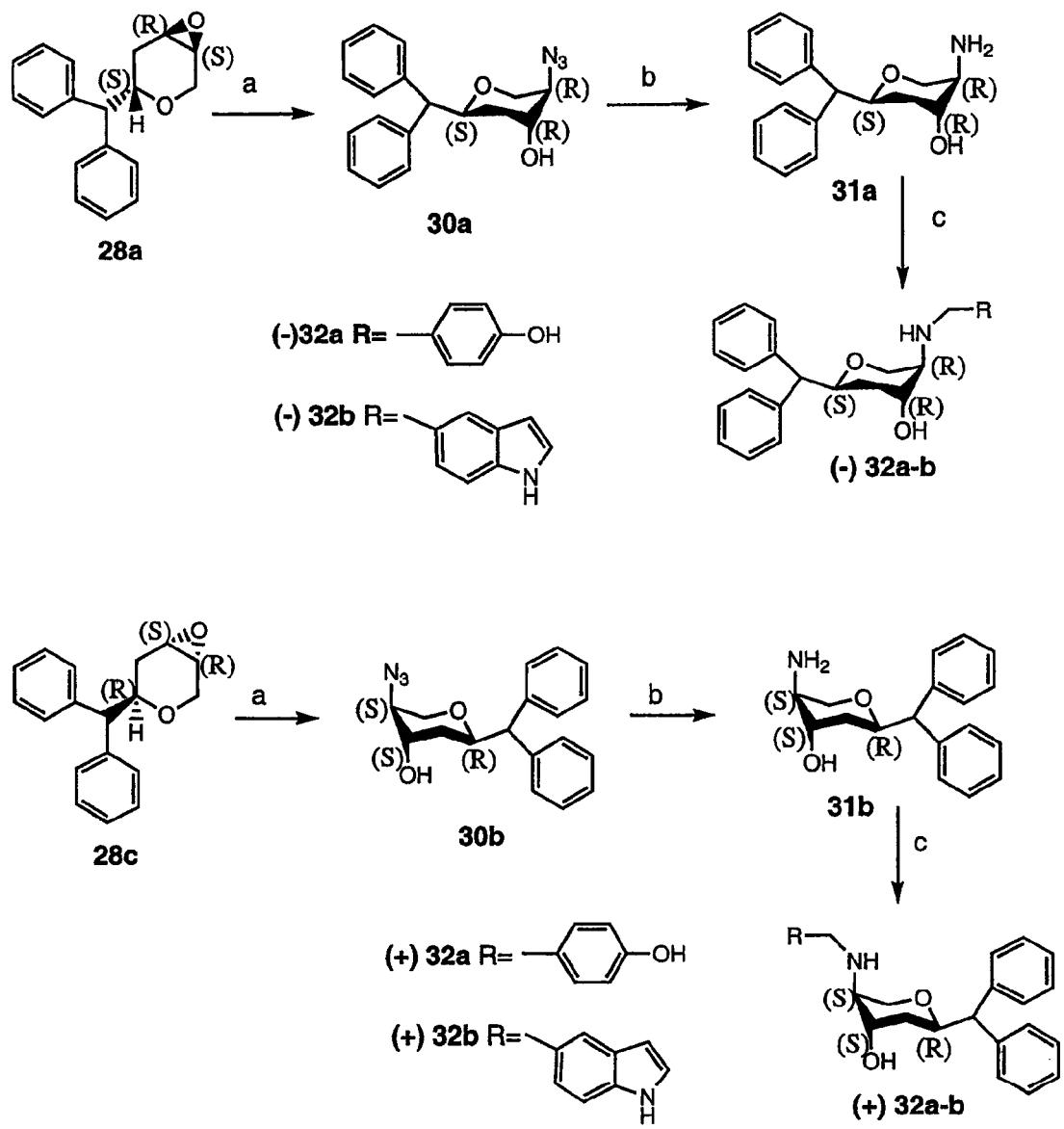
FIG. 9 provides a scheme for the preparation of compounds an embodiment of the present invention.
Figure 10:
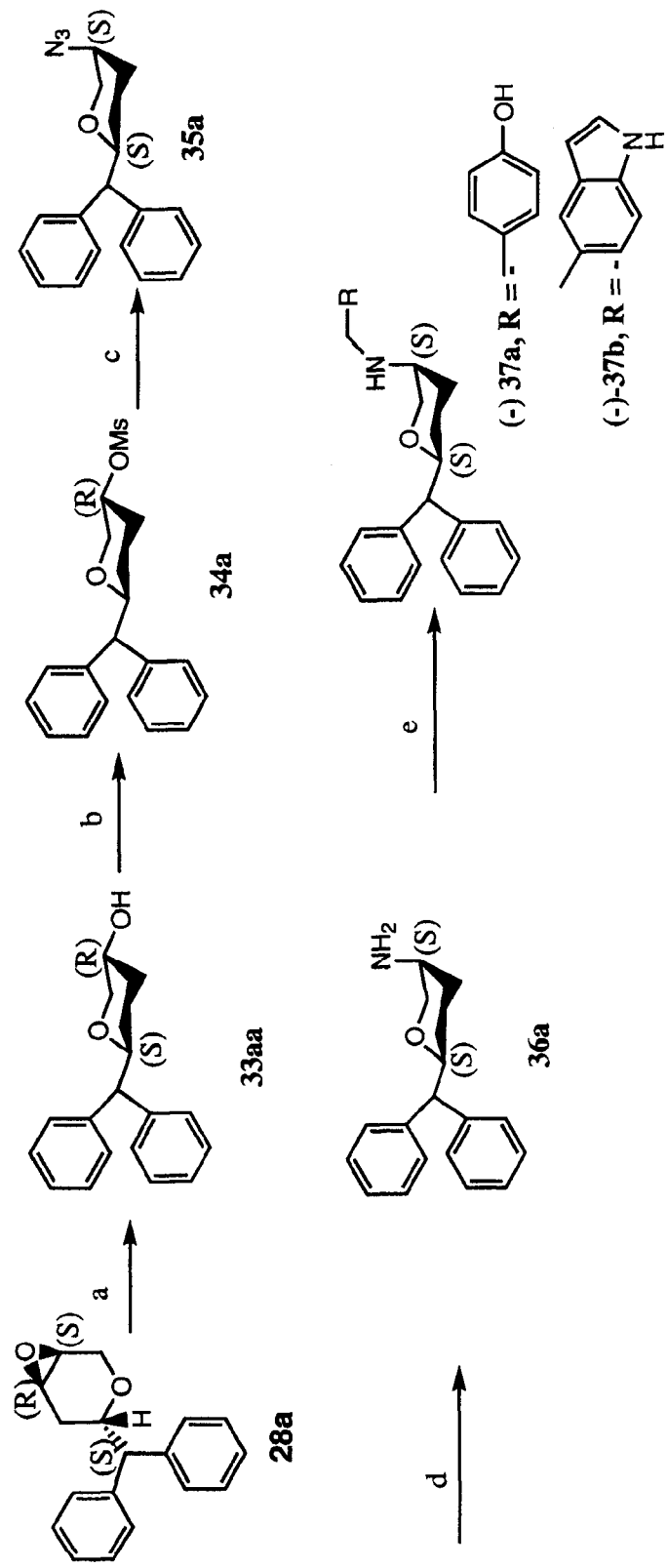
FIG. 10 provides a scheme for the preparation of compounds an embodiment of the present invention.
Figure 11:
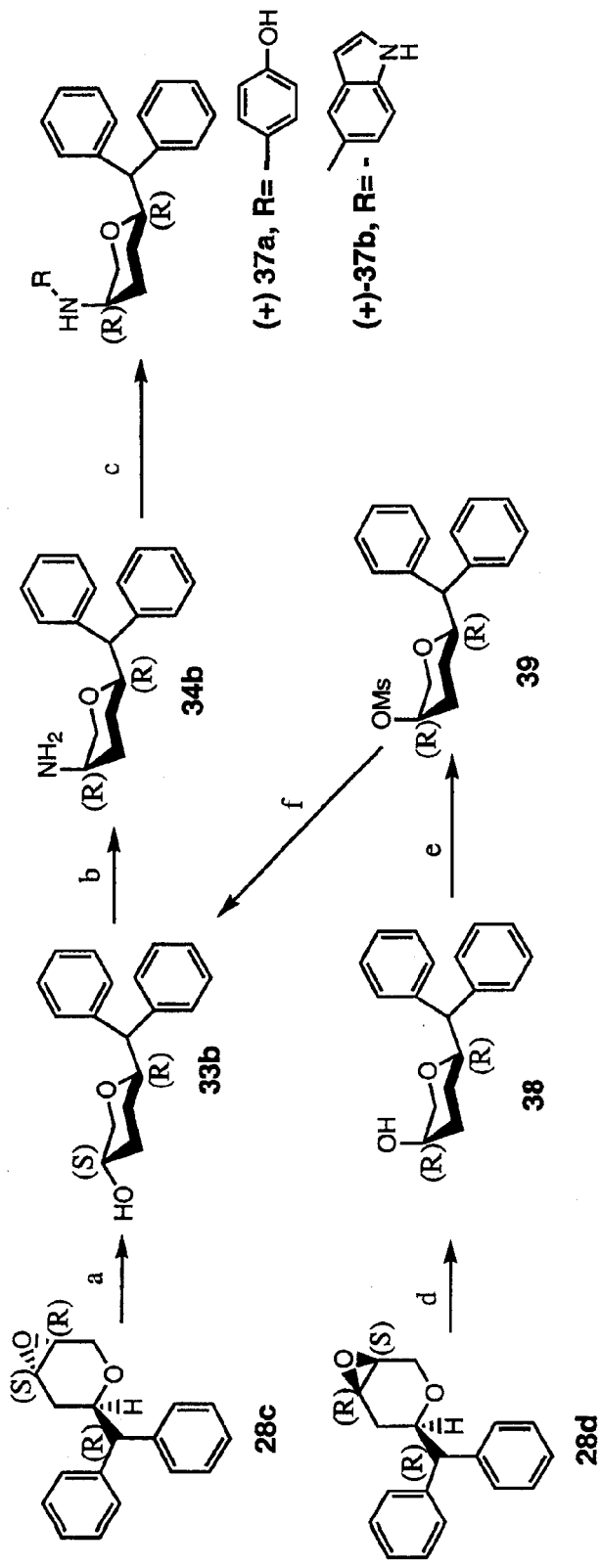
FIG. 11 provides a scheme for the preparation of compounds an embodiment of the present invention.
Figure 12:
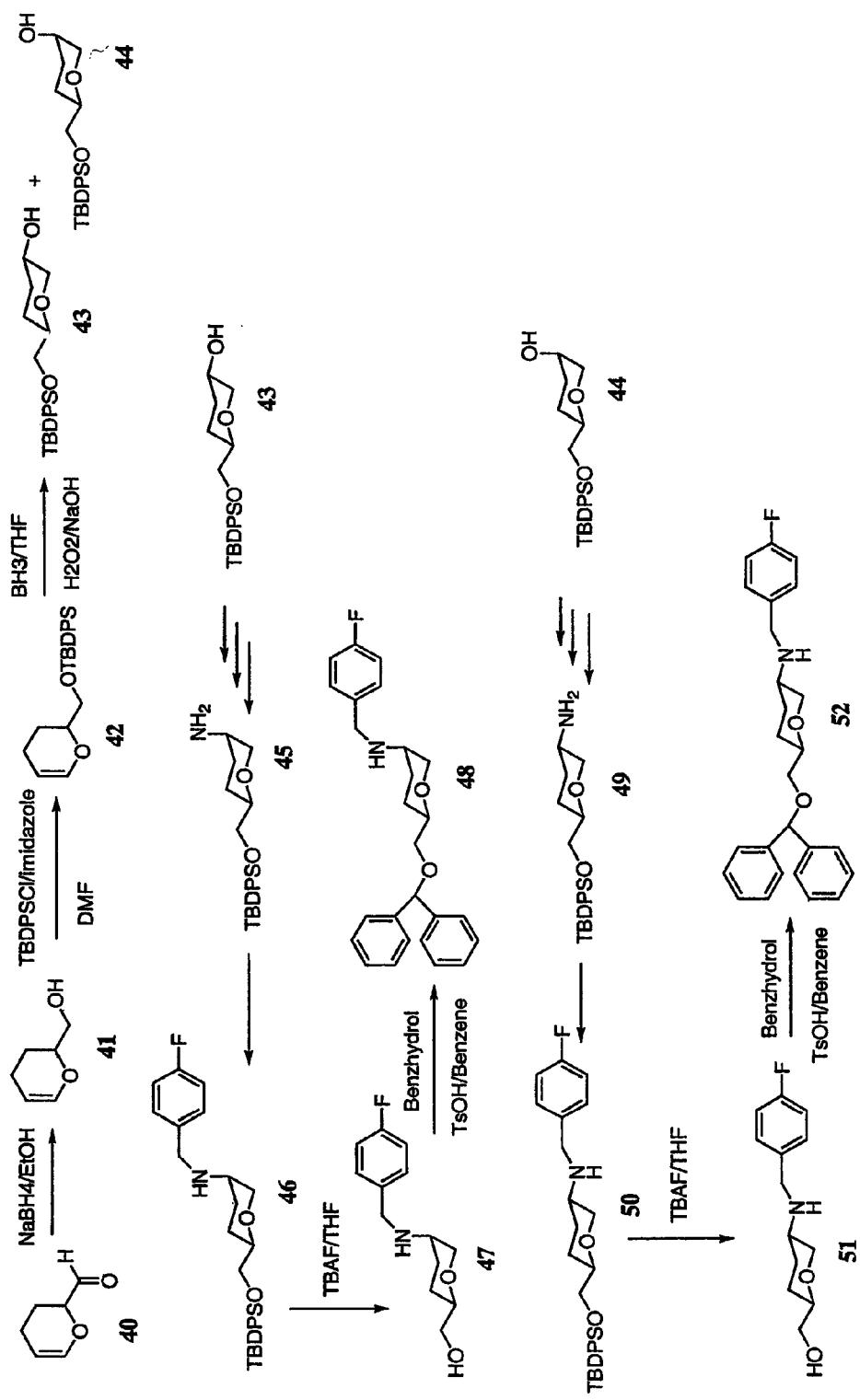
FIG. 12 provides a scheme for the preparation of compounds an embodiment of the present invention.
Figure 13:
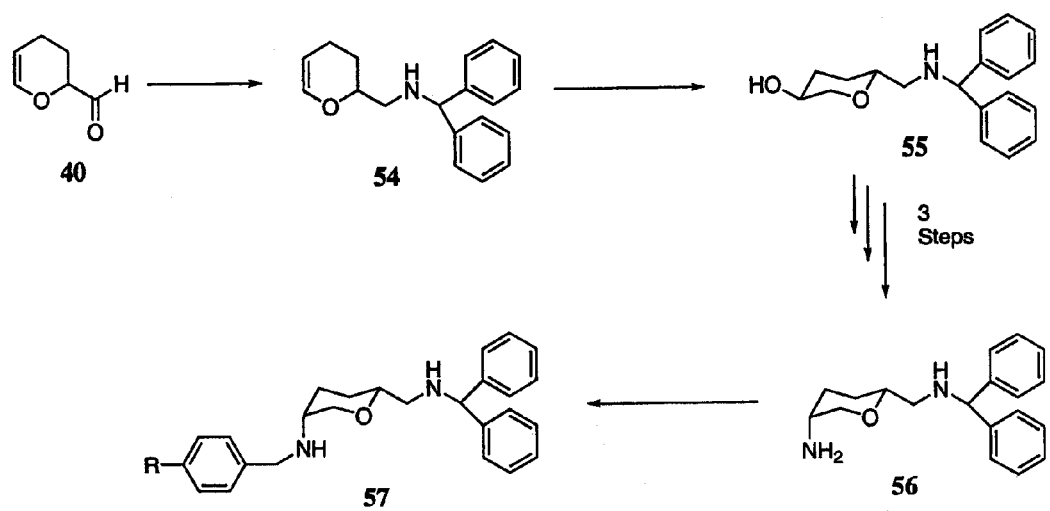
FIG. 13 provides a scheme for the preparation of compounds an embodiment of the present invention.
Figure 14:
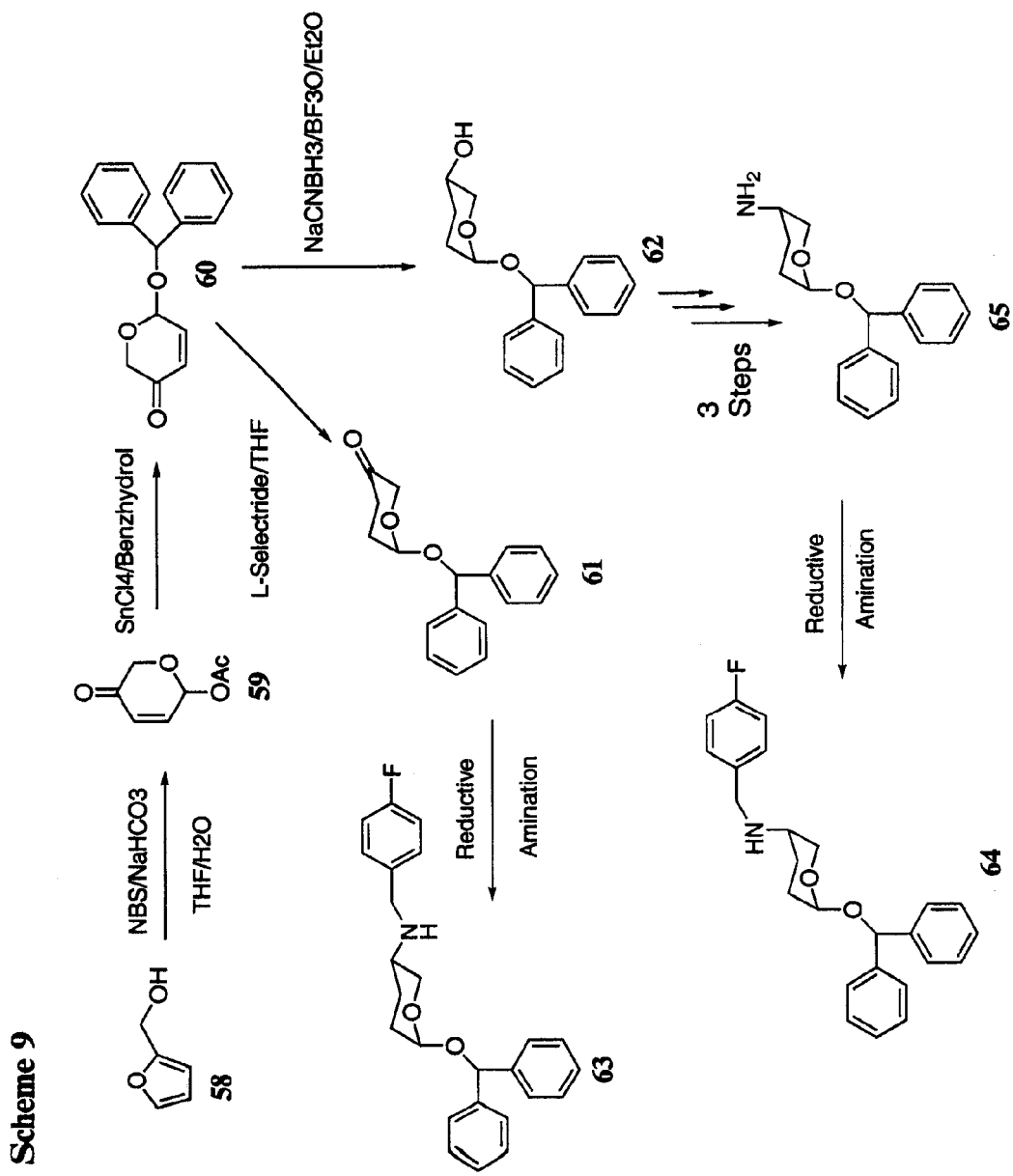
FIG. 14 provides a scheme for the preparation of compounds an embodiment of the present invention.

In general, there is a slight reduction of affinity in these pyran derivatives for the DAT compared to their piperidine counterparts (see Table 1). This loss of affinity could be due to the replacement of the basic N-atom in the piperidine derivative by a less basic O-atom resulting in an altered mode of interactions. In this regard, the cis-3,6-disubstituted pyran derivatives, as shown in structure 1b above, actually represent pharmacophoric structures for DAT interaction, as either cis- or trans-2,4-disubstituted and trans-3,6-disubstituted compounds, shown as 1c, 1d and 1e and FIG. 2, were much weaker at DAT (see Table 1). Interestingly, one of the notable features observed in pyran derivatives bearing a potential H-bonding hydroxyl or amino functionality in the aromatic ring, was their significant increase of activity towards NET which was not observed for the corresponding piperidine counterparts. This affinity for NET is attributed to a formation of H-bonding between the functional groups in the benzyl moiety of the pyran molecules and the NET. Support for this came from the design of a molecule in which the original potential H-bonding bearing functional hydroxyl group connected to a phenyl moiety was modified into a bio-isosteric equivalent indole substituent where an indole amino moiety effectively replaced the hydroxyl group. The resulting indole derivative was also potent at NET, thus, confirming the potential involvement of an H-bond interaction.

TABLE 1

Affinity of Drugs at Dopamine, Serotonin, and Norephinephrine Transporters in Rat Striatum

| Compound | Inhibition of [$^3$H]Win 35, 428 binding to DAT IC$_{50}$, nM,[a] | Inhibition of [$^3$H]citalopram binding to SERT, IC$_{50}$, nM[a], | Inhibition of [$^3$H]nisoxetine binding to NET, IC$_{50}$, nM[a] | Inhibition of [$^3$H]DA1[a] uptake by DAT, IC$_{50}$, nM, |
|---|---|---|---|---|
| GBR 12909 | 10.6 ± 1.9 | 132 ± 0 | 496 ± 22 | |
| 1c | 1,302 ± 68 | 3,313 ± 170 | 5,101 ± 1,037 | |

TABLE 1-continued

Affinity of Drugs at Dopamine, Serotonin, and Norephinephrine Transporters in Rat Striatum

| Compound | Inhibition of [³H]Win 35, 428 binding to DAT IC$_{50}$, nM,[a] | Inhibition of [³H]citalopram binding to SERT, IC$_{50}$, nM[a], | Inhibition of [³H]nisoxetine binding to NET, IC$_{50}$, nM[a] | Inhibition of [³H]DA1[a] uptake by DAT, IC$_{50}$, nM, |
|---|---|---|---|---|
| 1d | 1,581 ± 283 | 4,778 ± 1,808 | 17,543 ± 2,153 | |
| 1e[b] | 313 ± 71 | 8,410 ± 163 | 12,700 ± 3,180 | |
| 1b | 303 ± 14 | 1577 ± 97 | 274 ± 29 | 242 ± 39 |
| 1a | 114 ± 10.6 | 2130 ± 110 | 612 ± 130 | |

The present inventor contemplated that introduction of a hydroxyl group as a third substitutent in the inventive 3,6-disubstituted pyran templates could allow additional interaction with the monoamine transporter, potentially resulting in compounds with interesting activity and selectivity. While introducing such a hydroxy group in the pyran ring, it was also desired to explore the additional influence of stereospecificity and regioselectivity in the interaction of the pyran compounds with monoamine transporters. For this purpose, a novel asymmetric synthesis method via isomeric epoxide ring opening was used to introduce all three substituents in a stereo- and region-specific manner, followed by their biological evaluation at all three monoamine transporters.

The results of the work described above was the generation of a novel trisubstituted pyran template based on 3,6-disubstituted pyran derivatives. These trisubstituted derivatives represent a unique molecular template with a pyranyl backbone structure as blockers for monoamine transporters. Successful design and asymmetric synthesis of these analogs has been accomplished. The results indicate a clear separation of activity between enantiomers and demonstrate the presence of (2S,4R,5R) absolute configuration in the most active enantiomer for interaction with NET and SERT. It has been further surprisingly discovered that there are interesting differences in the activity profiles of these compounds, depending on the nature of the substitution on the phenyl ring of an N-benzyl moiety.

The compounds defined herein may be synthesized by methods known to chemists, in general. However, certain of the synthesis steps leading to stereoisomers of the trisubstituted pyrans are novel, and their use is also claimed herein. Several general reaction schemes are worthy of some discussion. Details of the synthesis and a more complete description of reaction schemes follows.

The compounds described herein are all potent inhibitors of monoamine transport, and exhibit reversible but strong binding affinities for the various monoamine transporters. However, some of the compounds exhibited preferable binding to the NET and/or SERT. This binding behavior places these compounds in a different category than analogues not containing a 3,6-substituted pyran ring system such as piperidine compounds with otherwise similar structure.

For example, in vitro data, which has been shown by many studies to correlate with in vivo activity, indicates that (−) isomers of the present invention are potent blockers for serotonin (SERT) and norepinephrine (NET) transporters. Compounds (−)29a, (−)-29e-, (−)29f, (−)32b and (−)37a are dual transport blockers as they bind to both the SERT and NET. Compounds of this class are known to those skilled in the art as SNRI (serotonin and norepinephrine reuptake inhibitors) and are considered potent anti-depressants. Compounds (−)29b, (−)29d, (−)32a, (+)32a, and (+)37a, are more selective for the NET and are known as NRI, also considered potent anti-depressants. Reboxetine, an NRI, was recently approved for use as an anti-depressant. SNRI are now considered to have favorable pharmokinetics as compared to SSRI (serotonin blocker only). Other disorders for which use of such compounds have been documented include panic disorder, post traumatic stress disorder, social phobia, and obsessive-compulsive disorder.

In an embodiment of the present invention, the CNS-active compounds of the present invention are substituted pyran compounds described by formulae I:

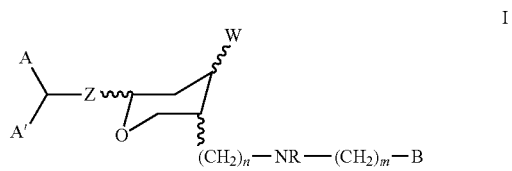

I or a pharmaceutically acceptable derivative or salt thereof, wherein

A an A' are individually selected from the group of optionally substituted C$_4$-C$_{14}$ aryl and heteroaryl wherein heteroatoms of heteroaryl A and/or A' are selected from the group consisting of O, N, and S;

Z is a chemical bond or —Y—(CH$_2$)$_o$—;

Y is NH or O;

o is 0, 1, 2, 3, or 4;

R is H, C$_{1-8}$ alkyl, C$_{2-8}$ alkenyl, or C$_{2-8}$ alkynyl;

W is hydrogen, —OH, or —NHR;

B is optionally substituted C$_4$-C$_{14}$ aryl or optionally substituted C$_4$-C$_{14}$ heteroaryl; and n and m are each independently 0, 1, 2, 3, or 4.

The compounds of formula I contain a pyran ring which is substituted in the 3 and 6 positions, and in preferred embodiments further substituted by a hydroxyl group (or derivative thereof) in the 4 position. In the structure given above, the squiggle bonds between the pyran ring and the W and (CH)$_2$ groups indicates that these groups may be bound at axial or equatorial positions. The AA'CHZ group may be bound in a similar manner.

In a variation of the compounds having formula I, the CNS-active compounds of the present invention correspond to contain a pyran ring which is substituted in the 3 and 6 positions, and in preferred embodiments further substituted by a hydroxyl group (or derivative thereof) in the 4 position. In the structure given above, the squiggle bonds between the pyran ring and the W and (CH)$_2$ groups indicates that these groups may be bound at axial or equatorial positions. The AA'CHZ group may be bound in a similar manner.

In a variation of the compounds having formula I, any carbon of —(CH$_2$)$_n$ be substituted by —OR$^4$ or —COOR$^5$ where R$^4$ is H, C$_{1-8}$ alkyl, C$_{5-10}$ cycloalkyl, or C$_{2-18}$ alkylene; and R$^5$ is C$_{1-8}$ alkyl or C$_{2-18}$ alkylene. In another variation of the compounds having formula I, A and A' are preferably aryl (inclusive of heteroaryl) groups optionally substituted by C$_{1-4}$ alkyl, C$_{2-6}$ alkenyl, C$_{2-6}$ optionally halogenated alkynyl, C$_{2-4}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$; where R$^4$ is H, C$_{1-18}$ alkyl, C$_{5-10}$ cycloalkyl, or C$_{2-18}$ alkylene; and R$^8$ is C$_{1-8}$ alkyl, C$_{5-6}$ cycloalkyl, C$_{2-8}$ alkenyl, or a 5 or 6-member aromatic ring including heterocyclic rings. B may be selected from the same groups as set forth above for A and A'. Preferably, A and A' are an optionally substituted phenyl, napthyl, anthryl, furanyl, thienyl, or pridinyl group. Similarly, B may be selected from the same groups. Most preferably, A is unsubstituted phenyl and A' is unsubstituted phenyl or mono- or disubstituted phenyl where substituents are preferably $C_{1-4}$ alkyl, $C_{1-4}$ alkoxy or halo. B is preferably phenyl, most preferably phenyl substituted by halo, cyano, $C_{1-4}$ alkoxy, or nitro, most preferably monosubstituted by halo, cyano, or nitro, or disubstituted by halo, preferably chloro and/or fluoro.

Preferred compounds are also those in which the —(CH$_2$)-n group are bound equatorially or axially at the 3-position of the pyran ring. Most preferably, the compounds of formula I are (−)-isomers of 3,6-disubstituted pyrans also containing a hydroxyl substituent (or derivative thereof) at the 4 position. In these compounds, the meanings of A, A', B, etc., are the same as for the general formula previously given. Most preferred isomers are those depicted in FIGS. 7-11.

In a still another variation of the compounds having formula I, at least one of A and A' are selected from the group consisting of:

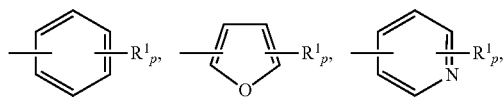

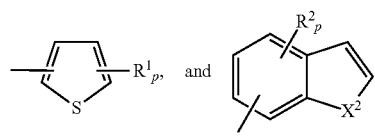

wherein:

p is 0-6;

$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^2$ has the meaning of $R^1$ and also a 5 or 6 membered heterocycle containing 1 or more heteroatoms selected from the group consisting of N, O, and S;

$X^2$ is N, O, or S;

$R^4$ is H, $C_{1-18}$ alkyl, $C_{5-10}$ cycloalkyl, or $C_{2-18}$ alkylene; and $R^8$ is $C_{1-8}$ alkyl, $C_{5-4}$ cycloalkyl, $C_{2-8}$ alkenyl, or a 5 or 6-member aromatic ring including heterocyclic rings;

B is selected from the group consisting of

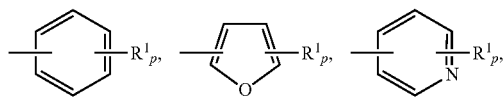

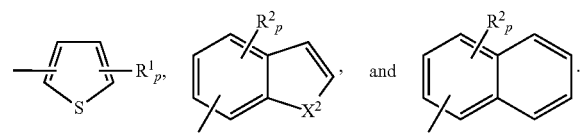

More specific examples of the compounds having formula I, include compounds having the following formulae:

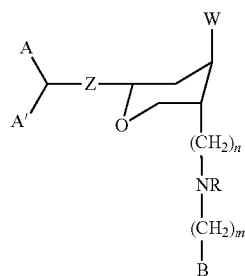

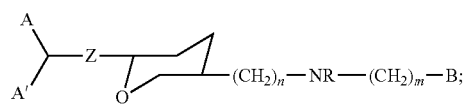

wherein W, A, A', Z, n, m, and R are set forth above.

Still more specific compounds having formula I, include compounds having the following formulae:

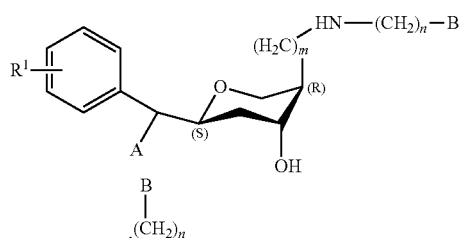

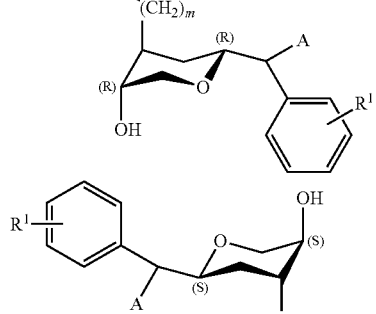

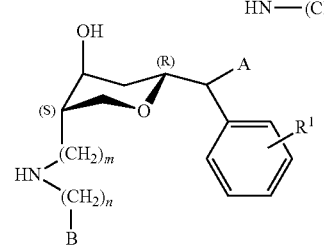

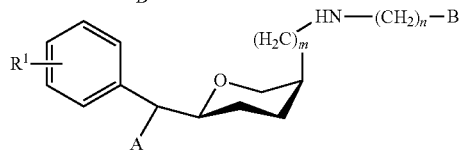

wherein:

B is optionally substituted $C_4$-$C_{14}$ aryl or optionally substituted $C_4$-$C_{14}$ heteroaryl;

$R^1$ is $C_{1-4}$ alkyl, $C_{2-4}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^4$ is H, $C_{1-18}$ alkyl, $C_{5-10}$ cycloalkyl, or $C_{2-8}$ alkylene; and $R^8$ is $C_{1-8}$ alkyl, $C_{5-6}$ cycloalkyl, $C_{2-8}$ alkenyl, or a 5 or 6-member aromatic ring including heterocyclic rings.

In another variation of the compounds having formula I, the CNS-active compounds of the present invention are described by formulae IIIa-h:

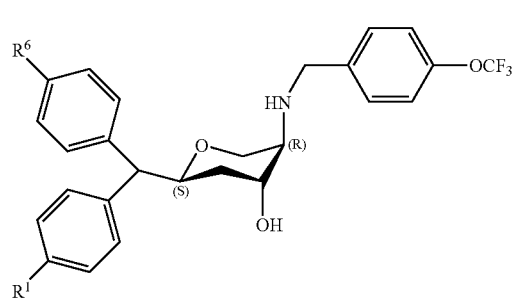

IIIa

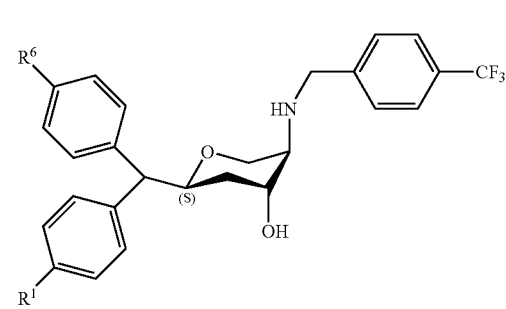

IIIb

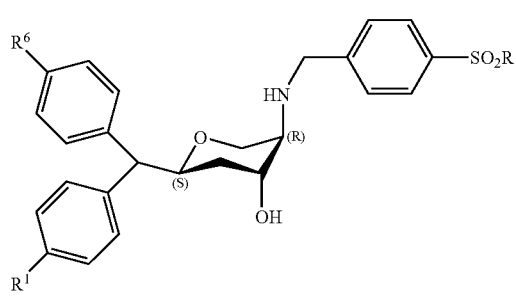

IIIc

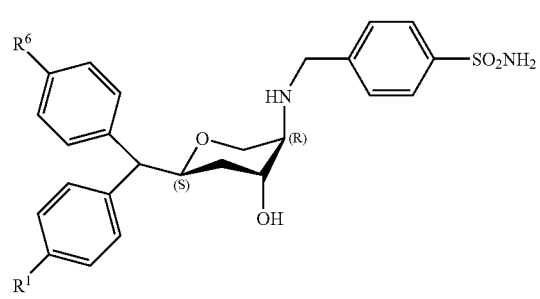

IIId

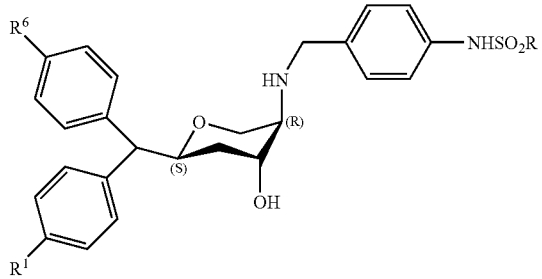

IIIe

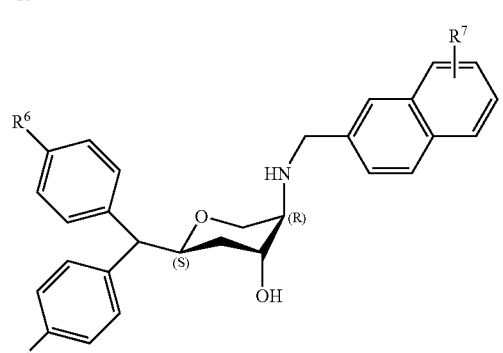

IIIf

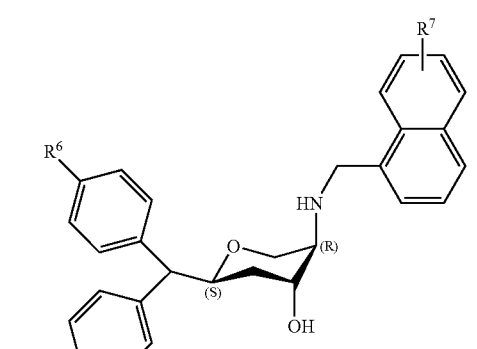

IIIg

IIIh or a pharmaceutically acceptable derivative or salt thereof, wherein:

R is H, $C_{1-8}$ alkyl, $C_{2-8}$ alkenyl, or $C_{2-8}$ alkynyl;

$R^1$, $R^6$, and $R^7$ are each independently $C_{1-4}$ alkyl, $C_{2-4}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^4$ is H, $C_{1-8}$ alkyl, $C_{5-10}$ cycloalkyl, or $C_{2-18}$ alkylene; and $R^8$ is $C_{1-8}$ alkyl, $C_{5-6}$ cycloalkyl, $C_{2-8}$ alkenyl, or a 5 or 6-member aromatic ring including heterocyclic rings.

In another variation of the compounds having formula I, the CNS-active compounds of the present invention are described by formulae IVa-c:

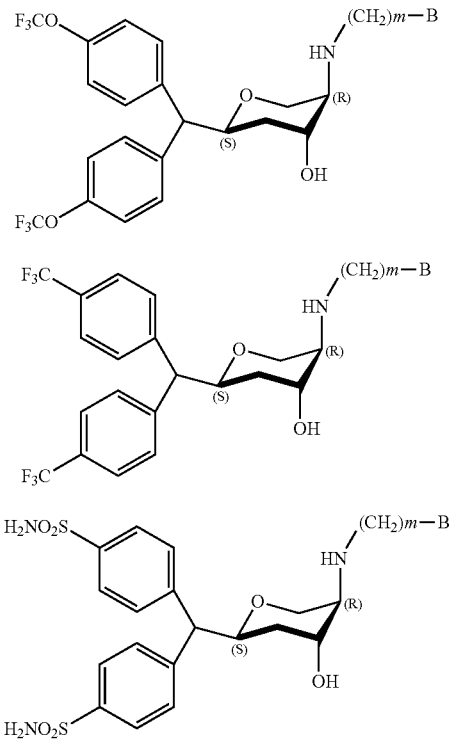

or a pharmaceutically acceptable derivative or salt thereof, wherein:

m is 0-4;

B is selected from the group consisting of:

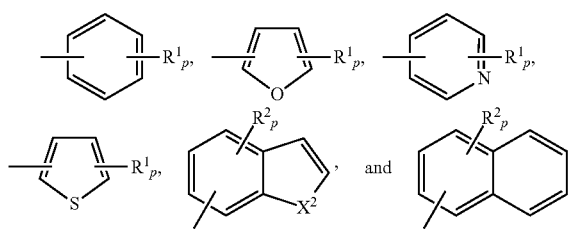

p is 0-6;

$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^2$ has the meaning of $R^1$ and also a 5 or 6 membered heterocycle containing 1 or more heteroatoms selected from the group consisting of N, O, and S;

$X^2$ is N, O, or S;

$R^4$ is H, $C_{1-18}$ alkyl, $C_{5-10}$ cycloalkyl, or $C_{2-18}$ alkylene; and $R^8$ is $C_{1-8}$ alkyl, $C_{5-6}$ cycloalkyl, $C_{2-8}$ alkenyl, or a 5 or 6-member aromatic ring including heterocyclic rings.

In another variation of the compounds having formula I, the CNS-active compounds of the present invention are described by formulae V:

or a pharmaceutically acceptable derivative or salt thereof, wherein:

m is 0-4;

Z is a chemical bond or —Y—(CH$_2$)$_o$—

Y is NH or O;

o is 0, 1, 2, 3, or 4;

at least one of A and A' are selected from the group consisting of:

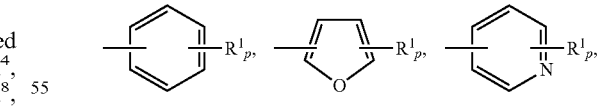

p is 0-6;

$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^2$ has the meaning of $R^1$ and also a 5 or 6 membered heterocycle containing 1 or more heteroatoms selected from the group consisting of N, O, and S, and $X^2$ is N, O, or S;

$R^4$ is H, $C_{1-8}$ alkyl, $C_{5-10}$ cycloalkyl, or $C_{2-18}$ alkylene;

$R^8$ is $C_{1-8}$ alkyl, $C_{5-4}$ cycloalkyl, $C_{2-8}$ alkenyl, or a 5 or 6-member aromatic ring including heterocyclic rings;

B is selected from the group consisting of

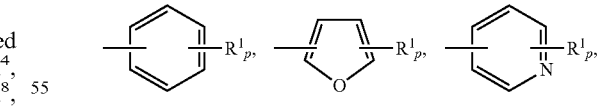

In another variation of the compounds having formula I, the CNS-active compounds of the present invention are described by formulae VIa-d:

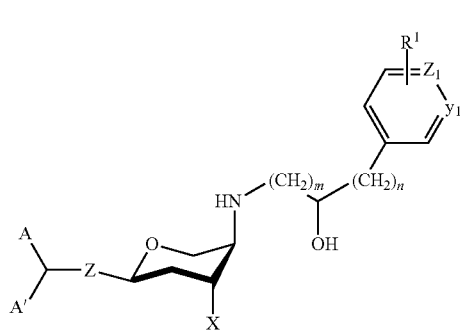

VIa

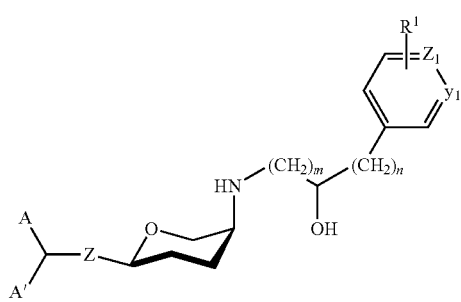

VIb

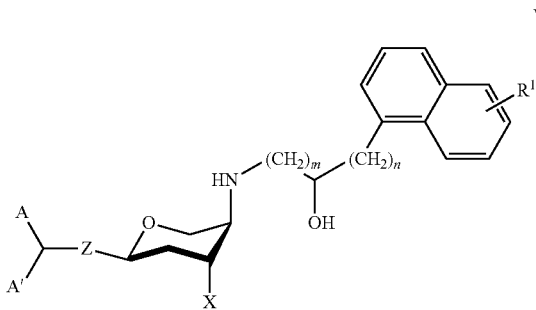

VIc

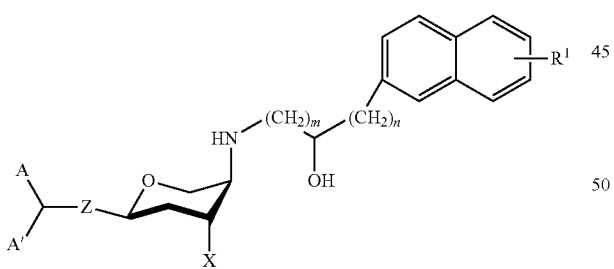

VId or a pharmaceutically acceptable derivative or salt thereof, wherein:

m and n are 0-4;
X is H, OH, $NH_2$, or NHR;
$Z^1$ and $Y^1$ are C- or N-atom;
Z is selected from the group consisting of a chemical bond and —Y—$(CH_2)_o$—;
Y is NH or O;
o is 0, 1, 2, 3, or 4;
at least one of A and A' are selected from the group consisting of:

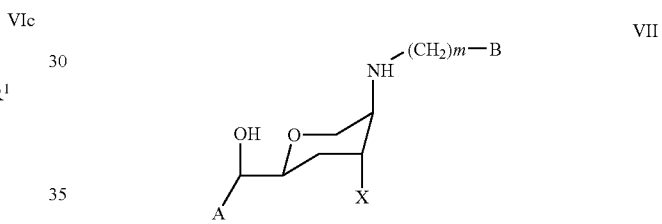

p is 0-6;
$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —$COOR^4$, —OH, —$NO_2$, —$NH_2$, —$NHR^4$, —$SO_2NH_2$, —$NHSO_2R^8$, —$OCF_3$, or —$OR^8$;
$R^2$ has the meaning of $R^1$ and also a 5 or 6 membered heterocycle containing 1 or more heteroatoms selected from the group consisting of N, O, and S;
$X^2$ is N, O, or S;
$R^4$ is H, $C_{1-8}$ alkyl, $C_{5-10}$ cycloalkyl, or $C_{2-18}$ alkylene; and
$R^8$ is $C_{1-8}$ alkyl, $C_{5-6}$ cycloalkyl, $C_{2-8}$ alkenyl, or a 5 or 6-member aromatic ring including heterocyclic rings.

In another variation of the compounds having formula I, the CNS-active compounds of the present invention are described by formulae VII:

VII or a pharmaceutically acceptable derivative or salt thereof, wherein:

m is 0-4;
X is —H, —OH, —$NH_2$, or —NHR;
at least one of A and A' are selected from the group consisting of:

p is 0-6;
$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —$COOR^4$, —OH, —$NO_2$, —$NH_2$, —$NHR^4$, —$SO_2NH_2$, —$NHSO_2R^8$, —$OCF_3$, or —$OR^8$;
$R^2$ has the meaning of $R^1$ and also a 5 or 6 membered heterocycle containing 1 or more heteroatoms selected from the group consisting of N, O, and S;
$X^2$ is N, O, or S;
$R^4$ is H, $C_{1-18}$ alkyl, $C_{5-10}$ cycloalkyl, or $C_{2-18}$ alkylene; and
$R^8$ is $C_{1-8}$ alkyl, $C_{1-6}$ cycloalkyl, $C_{2-8}$ alkenyl, or a 5 or 6-member aromatic ring including heterocyclic rings; and B is selected from the group consisting of

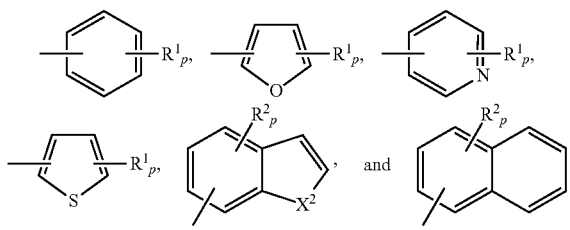

In another variation of the compounds having formula I, the CNS-active compounds of the present invention are described by formulae VIIIa-b:

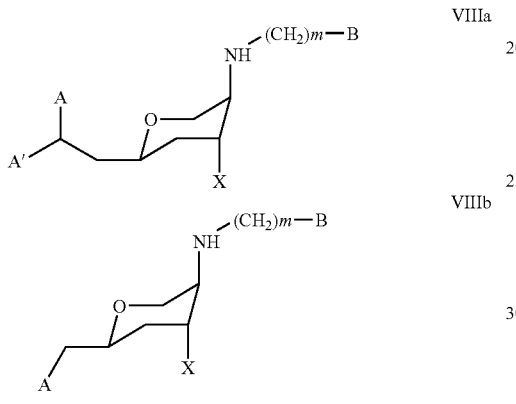

or a pharmaceutically acceptable derivative or salt thereof, wherein:

m is 0-4;

X is H, OH, $NH_2$, or NHR;

at least one of A and A' are selected from the group consisting of:

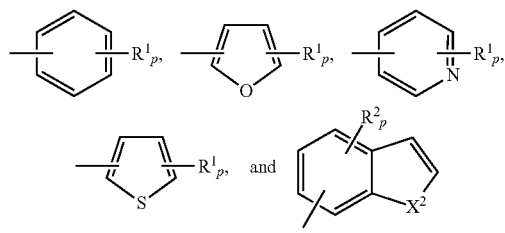

p is 0-6;

$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^2$ has the meaning of $R^1$ and also a 5 or 6 membered heterocycle containing 1 or more heteroatoms selected from the group consisting of N, O, and S;

$X^2$ is N, O, or S;

$R^4$ is H, $C_{1-8}$ alkyl, $C_{5-10}$ cycloalkyl, or $C_{2-18}$ alkylene; and $R^8$ is $C_{1-8}$ alkyl, $C_{5-6}$ cycloalkyl, $C_{2-8}$ alkenyl, or a 5 or 6-member aromatic ring including heterocyclic rings.

B is selected from the group consisting of:

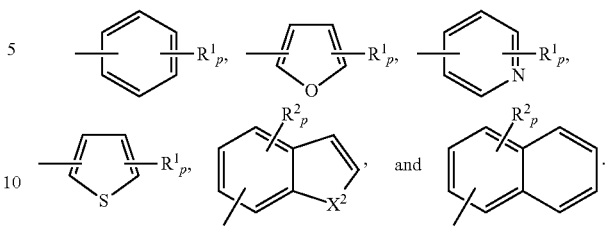

In another variation of the compounds having formula I, the CNS-active compounds of the present invention are described by formulae IXa-b:

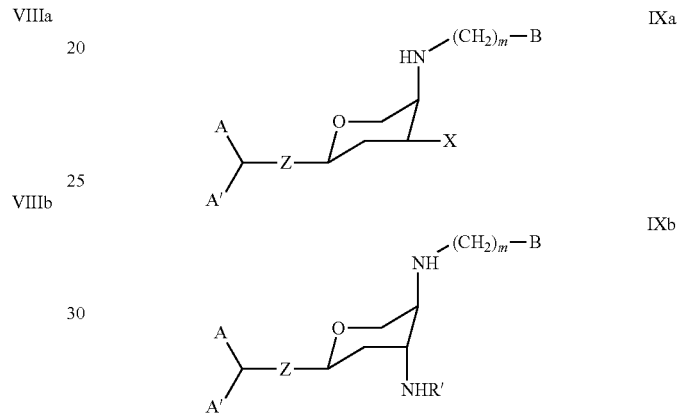

or a pharmaceutically acceptable derivative or salt thereof, wherein:

m is 0-4,

X is H, OH, $NH_2$, or NHR;

Z is a chemical bond or —Y—(CH$_2$)$_o$—;

Y is NH or O;

o is 0, 1, 2, 3, or 4.

at least one of A and A' are selected from the group consisting of:

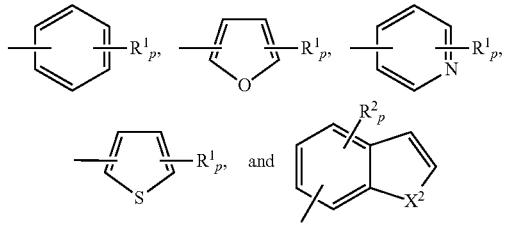

p is 0-6;

$R^1$ is $C_{1-4}$ alkyl, $C_{2-6}$ alkenyl, $C_{24}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;

$R^2$ has the meaning of $R^1$ and also a 5 or 6 membered heterocycle containing 1 or more heteroatoms selected from the group consisting of N, O, and S;

$X^2$ is N, O, or S;

$R^8$ is $C_{1-8}$ alkyl, $C_{1-6}$ cycloalkyl, $C_{2-8}$ alkenyl, or a 5 or 6-member aromatic ring including heterocyclic rings; and B is selected from the group consisting of:

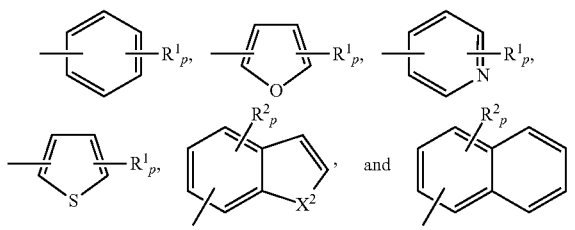

In another embodiment of the present invention, the CNS-active compounds are described by formula X:

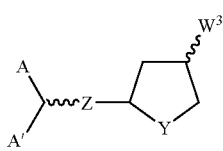

X or a pharmaceutically acceptable derivative or salt thereof, wherein:
A, A', and B are individually selected from the group of optionally substituted $C_4$-$C_{14}$ aryl and heteroaryl wherein heteroatoms of heteroaryl
A and/or A' are selected from the group consisting of O, N, and S;
Z is a chemical bond or —Y—$(CH_2)_o$;
Y is NH or O;
o is 0, 1, 2, 3, or 4;
R is H or $C_{1-8}$ alkyl; and
$W^3$ is an alkyl amine derivative or an aryl amine derivative.

In a variation of the compounds having formula X, the CNS-active compounds of the present invention are described by formulae XIa-b:

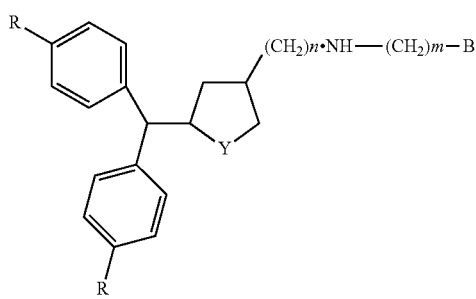

XIa

XIb or a pharmaceutically acceptable derivative or salt thereof, wherein:
m and n are 0-4;
Z is a chemical bond or —Y—$(CH_2)_o$—;
Y is NH or O;
o is 0, 1, 2, 3, or 4;

Y is NH, O;
at least one of A and A' are selected from the group consisting of:

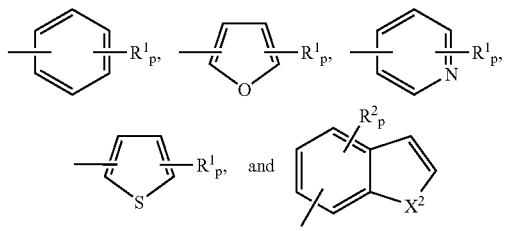

p is 0-6;
$R^1$ is $C_{1-4}$ alkyl, $C_{2-6}$ alkenyl, $C_{2-6}$ optionally halogenated alkynyl, $C_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;
$R^2$ has the meaning of $R^1$ and also a 5 or 6 membered heterocycle containing 1 or more heteroatoms selected from the group consisting of N, O, and S;
$X^2$ is N, O, or S;
$R^4$ is H, $C_{1-8}$ alkyl, $C_{5-10}$ cycloalkyl, or $C_{2-18}$ alkylene;
$R^8$ is $C_{1-8}$ alkyl, $C_{5-6}$ cycloalkyl, $C_{2-8}$ alkenyl, or a 5 or 6-member aromatic ring including heterocyclic rings;
B is selected from the group consisting of:

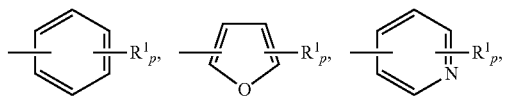

In another variation of the compounds having formula X, the CNS-active compounds of the present invention are described by formulae XII:

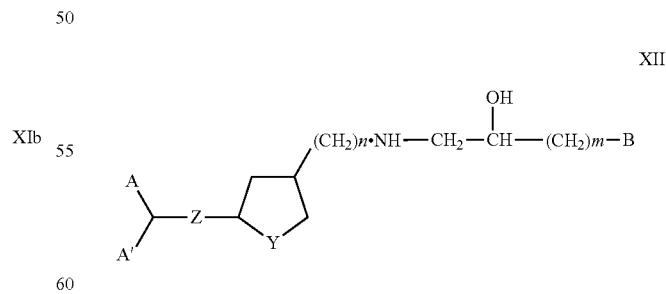

XII wherein
m and n are 0-4;
Z is a chemical bond or —Y—$(CH_2)_o$;
Y is NH or O;
o is 0, 1, 2, 3, or 4;

at least one of A and A' are selected from the group consisting of:

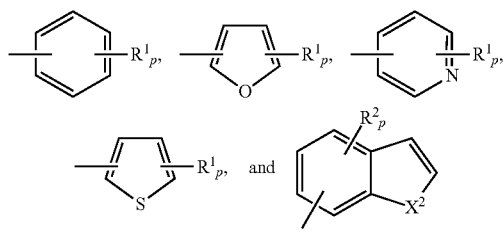

is 0-6;
R$^1$ is C$_{1-4}$ alkyl, C$_{2-6}$ alkenyl, C$_{2-6}$ optionally halogenated alkynyl, C$_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;
R$^2$ has the meaning of R$^1$ and also a 5 or 6 membered heterocycle containing 1 or more heteroatoms selected from the group consisting of N, O, and S;
X$^2$ is N, O, or S;
R$^4$ is H, C$_{1-8}$ alkyl, C$_{5-6}$ cycloalkyl, or C$_{2-18}$ alkylene; and
R$^8$ is C$_{1-8}$ alkyl, C$_{5-6}$ cycloalkyl, C$_{2-8}$ alkenyl, or a 5 or 6-member aromatic ring including heterocyclic rings; and
B is selected from the group consisting of:

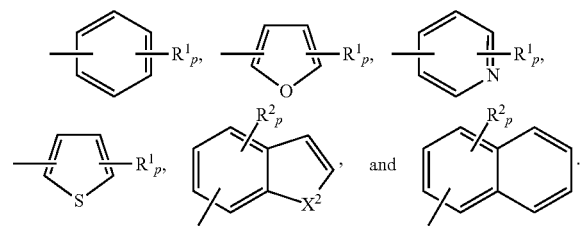

The subject invention compounds may be used as such or in the form of their pharmaceutically acceptable derivatives and/or salts. By the term "derivative" is meant a chemically modified form of the "base compound" which will liberate an active form of the base compound or metabolite thereof following administration, and does not include salts of the base compound. However, derivatives may also, when appropriate, also be used in the form of salts. The particular type of derivative is dependent, in most cases, on the nature of functional group(s) present on the base compound or its salt, and selection of a suitable derivative is within the skill of the art. For example, when hydroxyl groups are present, ethers or esters are common derivatives, especially the latter, as are also carbamates.

In general, the derivative is hydrolyzable to the base compound in vivo or is enzymatically converted, in one or more steps, to the base compound (or a salt thereof). In the case of primary or secondary amino groups, common derivatives include amides, imides, ureas, and the like. Preparation of all these derivatives may take place by standard methods of organic chemistry. Simple esters may be produced from hydroxyl groups by esterification with a carboxylic acid, sulfonic acid, etc., a carboxylic acid anhydride, a carboxylic acid chloride, etc. Carbamates may be prepared by reaction with an organic isocyanate.

Further derivatives include inclusion compounds and clathrates, for example inclusion complexes formed from the contact of host molecules such as α, β, and γ-cyclodextrins, or chemically modified cyclodextrins well known to the art. Urea inclusion compounds are also derivatives. In these derivatives, the gurst molecules (base compounds) are not chemically bound, but are present due to molecular attraction, hydrogen bonding, surface energy effects, etc. In general, such complexes are stoichiometric, but non-stoichiometric complexes may also be used. Such complexes are easily prepared by one skilled in the art. For example, cyclodextrin complexes may be prepared by kneading together cyclodextrin and base compound in water followed by removal of free water.

Salts are most useful forms of the subject invention compounds, and are formed by the neutralization of basic nitrogen atoms in the base compound by an organic or inorganic acid. Useful organic acids are in particular carboxylic acids and sulfonic acids. Examples of mono-, di-, and polycarboxylic acids which are useful include formic acid, acetic acid, propionic acid, butyric acid, maleic acid, fumaric acid, malic acid, tartaric acid, citric acid, succinic acid, sulfosuccinic acid, tannic acid, and the like. An example of a sulfonic acid is toluene sulfonic acid. Examples of inorganic acids include hydrochloric acid, sulfuric acid, nitric acid, phosphoric acid, polyphosphoric acid, molybdic acid, nitrous acid, sulfurous acid, and the like. The salts are prepared by simply neutralizing the base compound all or in part, generally in aqueous solution. In such cases, water of hydration may be a part of the salt thus produced.

The compounds may be administered by any suitable technique, including intravenous administration, but are preferably administered in solid form, for example as a tablet or capsule, optionally in conjunction with conventional pharmaceutical additives such as tableting aids, lubricants, fillers, pH-adjusting substances, pH-regulating substances (buffers), emulsifiers, dispersing aids, antioxidants, UV-stabilizers, etc. Such ingredients are well known. The compositions may also be administered in other forms, such as syrups, dispersions, etc.

The dosage to be administered to a mammalian species is dependent on numerous factors such as the particular species, its weight, the type of disorder, the desired degree of treatment, and the individual itself. Dosages can be readily determined by one skilled in the art by routine tests, for example time/serum level measurements, dose/response curves, etc. The dosages are in particular easy to range, as numerous monoamine transport-affecting drugs are commercially available, have extensive in vitro and in vivo results presented in the literature, or are in clinical trials. This is true for both human and non-human subjects, anti-anxiety medication being common for use in domestic dogs and cats, for example.

Dosage ranges which are useful also vary with respect to the activity of the individual compounds, for example the measured in vitro or in vivo activities reported in Tables 1 to 5 herein, as well as whether the compound is administered in a fast or slow release formulation, its solubility, its rate of transfer into the plasma or into the extracellular space, etc. Preferable serum concentrations range from 200 ng/mL to 80 ng/mL, more preferably 180 ng/mL to 85 ng/mL, with the foregoing constraints in mind. In non-slow-release formulations, dosages for the average mammal may range from 0.05 mg/Kg of body weight to about 10 mg/Kg of body weight, more preferably 0.1 mg/Kg to 5 mg/Kg. Slow release formulations will involve greater amounts of active ingredient.

Chemistry

Target compounds 7a,b and 16a-p were synthesized by following synthetic procedures shown in Scheme 1 to Scheme 5 depicted in FIGS. 1-5.

Synthesis of the target compounds 7a and 7b, shown in Scheme 1, was accomplished in high yields by following efficient synthetic routes. The basic pyranose ring structure in compound 2 was achieved by [4+2] Hetero-Diels-Alder cycloaddition (a) of Danishefsky's diene and aldehyde 1 in the presence of $BF_3.Et_2O$ which produced 2 in 80% yield. Reduction of 2 with $NaCNBH_3$ in presence of $BF_3$-$Et_2O$ in THF (b) produced racemic cis- and trans-mixture of 3a and 3b (2.5:1) in 96% yield. The two isomers were separated by careful flash chromatography, and their structures were assigned by NMR and NOE. Compounds 6a and 6b were synthesized from 3a and 3b respectively in high yields by three steps (c,d,e) which involve first mesylation with methanesulfonyl chloride in dry dichloromethane to produce 4a and 4b, followed by treatment with sodium azide in DMF with inversion of configuration to produce azides 5a and 5b. This azido displacement reaction resulted in production of the cis-isomer 5a from trans-4a and the trans-isomer 5b from cis-4-b. Finally, catalytic hydrogenation of the azides 5a and 5b with Pd/C produced the amine precursors 6a and 6b in good yield. Reductive amination (f) of 6a and 6b furnished 7a and 7b, respectively, in 72.6% and 54% yield.

Scheme 2 delineates the preparation of the key pyran 3,6-disubstituted intermediate 11 with trans-stereochemistry. Briefly, aldehyde 1 was converted (a) into 8 by reacting with an in situ prepared Grignard reagent prepared from 4-bromo-1-butene and magnesium in dry ether, in 91% yield. O-vinylation of 8 with ethyl vinyl ether (b) in the presence of $Hg(OCOCF_3)_2$ at room temperature produced 9 in 66% yield. Ring closing metathesis (c) of 9 in presence of a Grubb's catalyst in refluxing benzene afforded olefin 10 in 92.6% yield. Hydroboration of 10 with 9-BBN in THF, followed by oxidation (d) gave exclusively trans-isomer 11 in 93.5% yield. Compound 11 was used next as a starting precursor for the synthesis of various derivatives with different substitutions at the exocyclic N-atom as shown in the scheme 3 and scheme 4.

First, as shown in scheme 3, compound 11 was subjected to a Swern oxidation reaction (a) which produced ketone 12 in 91% yield. Reductive amination of 12 with 4-fluorobenzylamine (b) produced 16a as a major product in 45% yield. As described in the synthesis of compound 6a-b in Scheme 1, compound 11 was next converted as shown in Scheme 4, into a cis-amine intermediate 15 via three steps consisting first, of mesylation with methanesulfonyl chloride in dry dichloromethane (a), followed by substitution with sodium azide in DMF (b), and finally, catalytic hydrogenation with Pd—C in methanol (c). Reductive amination of 15 with various aldehydes (d) furnished target compounds 16b-n in good yield (Scheme 4).

The synthesis of compounds 16o and 16p is described in Scheme 5. 16o was synthesized by the reduction of 16d with tin (II) chloride dihydrate in ethanol and ethyl acetate in 60% yield (a). Amide Intermediate 17 was obtained from the reaction of amino-compound 15 with 4-fluoro-phenylacetyl chloride (b). Reduction of 17 with freshly generated borohydrate (c) gave the target compound 16p.

Following synthesis of 2,4-disubstituted cis and trans compounds 7a and 7b, they were characterized in binding assays for the three monoamine transporters (Table 2). Note that Table 2 contains data from numerous compounds and is more extensive in this regard than Table 1. In Table 1, compounds 1c, 1d, 1e, and 1b, are compounds 7a, 7b, 16a, and 16k of Table 2, respectively. Results indicated that the positional change from 3,6-disubstitution to 2,4-disubstitution adversely affected the binding activity of these two molecules. It is interesting to note that even though the activity of the 2,4-species was low, the preferential affinity for the DAT was still exhibited in the cis version. These results unexpectedly confirmed that the cis-3,6-disubstituted pyran template is a basic pharmacophoric requirement for interaction with DAT.

In the 3,6-disubstituted, replacement of a fluoro-substituent in the "B" aryl moiety by electron withdrawing substituents resulted in more potent compounds for the DAT as illustrated in the cyano-substituted molecule 16c and nitro-substituted molecule 16d. Nitro-substitution produced the most active compound among these synthesized analogs for the DAT (IC50=38.3 nM). Surprisingly, however, the electron donating methoxy substitutent in 16e produced comparable potency at the DAT ($IC_{50}$=84 nM). Introduction of 3,4-difluoro substituents in 16j reduced potency at all three transporters compared to the 4-fluoro 16b. With the dichlorosubstituted compound 16i, no improvement in activity was observed compared to unsubstituted 16k, indicating no correlation with, and a different mode of binding interaction of, as compared to tropane- and methylphenidate-type of compounds. As far as other halogen derivatives are concerned, the bromo compound 16l exhibited somewhat higher activity at DAT compared to unsubstituted 16k whereas the iodo compound 16m displayed comparable potency.

Compared to the methoxy substituted compound 16e, the hydroxy substituted compound 16h retained the activity at DAT (IC50=78.4 nM for 16h and IC50=84 nM for 16e), but its selectivity was shifted in favor of NET shown by the much higher activity at NET (IC50=22.6 nM for the NET, NET/DAT=0.29) (Table 3). The amino-substituted compound 16o also exhibited high potency at NET. These two substitutents can act as both hydrogen-bond donor or acceptor site, although in different capacity. The big shift towards activity and selectivity at NET caused by these two polar substitutents might indicate a critical involvement of hydrogen bond in interaction with NET. Similar results were not observed in structurally constrained piperidine analogs, reflecting the existence of different interaction modes between these two templates, and again confirming the unpredictability as between these respective classes of compounds. Since a high degree of homogeneity has been demonstrated between the DAT and NET structural sequence, it is highly surprising to observe that a subtle change in pyran structure can induce differential interactions in favor of the NET.

The nature of hydrophobic interaction of the aromatic moiety, was investigated by replacing the phenyl aromatic moiety in the benzyl group by bioisosteric indole moieties. Thus, replacement with a 2- and 3-indole moiety as illustrated in compounds 16g and 16f, led to moderate to diminished potency at DAT. Interestingly, the 2-indole substituted derivative 16g was 3.5 fold more active at DAT compared to the 3-substituted 16f (227 vs. 794 nM) and was also more active than the unsubstituted 16k. A similar increase in affinity for the NET was also observed for the 2-substituted indole compared to the 3-substituted compound (401 vs. 1860 nM). To assay the importance of the position of the indole N-atom along with hydrophobic interaction, the 5-substituted indole derivative 16n was designed and synthesized. In this regard, 5-substitution was chosen as it will assume the bioisosteric configuration of the p-hydroxyphenyl moiety of 16h. The binding results for 16n indicated high affinity, similar to 16h, for the NET, indicating the involvement of H-bonding with the indole amino moiety. This result further demonstrates the existence of an H-bond donor or acceptor site in the NET which, when oriented correctly with respect to ligand's H-bond forming functionality, can provide potent interaction.

In compound 16p, the fluorobenzyl moiety was replaced by a 4-fluorophenylethyl moiety which did not result, surprisingly, in decreased activity at DAT compared to 16b, in contrast to the results observed in constrained piperidine counterparts where a drop in DAT activity resulted from such modification. This result likely indicates that a different pharmacophoric orientation is required, probably via a distance geometry approach, to produce optimum activity in the pyran template. As we expected, exocyclic-N-substitution with an aromatic moiety is necessary in pyran derivatives for their activity at the monoamine transporter systems, as compound 15 exhibited little or no activity at the DAT.

Selected compounds with relatively higher activity at the DAT were tested in the DA uptake assay. For the most part no differential uptake and binding activity was observed with the exception of compound 16d which showed a three fold higher potency in inhibiting binding than uptake.

In order to demonstrate a difference in spatial distribution in the lowest energy conformers between 3,6-disubstituted and 2,4-disubstituted pyran derivatives, a preliminary molecular modeling study was performed. 2,4-Disubstituted compound 7a and the 3,6-disubstituted compound 16b were chosen for this study. Compounds were minimized first with the SYBYL molecular modeling program (version 6.9, 2002, Tripos Associates, Inc., St. Louis, Mo.), On a Silicon Graphics Octane IRIX 6.5 workstation. Minimized molecules obtained from this operation were next subjected to a grid search protocol to search for the lowest energy conformer.

First, each structure was fully minimized using standard Tripos force field with a distance dependent dielectric function, a 0.05 Kcal/mol Å energy gradient convergence criterion was used and the six-membered pyran ring was treated as an aggregate. The Powell method was used during minimization, and charges were computed using the Gasteiger-Huckel method within Sybyl 6.9. The number of iterations was 1000. After minimization the energy for 2,4-disubstituted molecule 7a was 5.85 Kcal/mol and the energy for 3,6-disubstituted molecule 16b was 5.63 Kcal/mol.

In the next step, using grid search protocol, the conformational search on each minimized molecule was performed by rotating the torsion angle of compounds 7a, and 16b formed by atoms α-β-γ-δ(see FIG. 3) from 0° to 360° by 10° increments. This method was used to perform a simple systematic search such that each specified torsion angle is varied over a grid of equally spaced values. While searching for the lowest energy conformer, a cutoff value of 8 Kcal/mol was specified relative to the lowest conformer, and charges were computed using the Gasteiger-Hückel method. Also, the six-membered pyran ring was treated as an aggregate. For compound 7a, a conformer with torsional angle 77.8° C. was found to have lowest energy, 3.16 Kcal/mol, whereas compound 16b produced lowest energy 5.61 Kcal/mol with a torsion angle 300°. These two lowest energy conformers were used next for overlapping.

In the final step, the two minimized structures were overlapped. During overlapping, the alignment program within Sybyl6.9 was employed, and the method used was common structure method. The compound 16b was used as template molecule and the six-membered pyran ring was used as common substructure for overlapping.

The pharmcophoric activity of the cis-3,6-disubstituted tetrahydro-pyran template at monoamine transporter systems was thus confirmed by SAR exploration with this template with various substituents on the exocyclic N-atom, producing potent activities at both DAT and NET. Compound 16d with the electron withdrawing nitro-substituent turned out to be the most active for the DAT. Interestingly, the compounds 16h and the 16o with para-hydroxy and para-amino substituents exhibited high potency for the NET, indicating formation of H-bonding. This was further confirmed by the bioisosteric version 16n which exhibited strong selective potency at NET. The SAR results for the current pyran molecules do not correspond with those for otherwise analogous piperidine derivatives, indicating differential interaction modes with monoamine transporters.

In still another embodiment of the present invention, a method of reducing monoamine reuptake in a mammalian species. The method of this embodiment comprising administering a binding amount of a monoamine receptor binder comprising at least one compound of the invention set forth above. In a variation of this embodiment, the method comprises administering to a patient exhibiting signs of depression, a compound of the invention in an amount effective to inhibit reuptake of serotonin at the SERT and norepinephrine at the NET. In still another variation of this embodiment, the method of the invention comprises administering to a patient exhibiting signs of depression, a compound of the invention in an amount effective to inhibit norepinephrine reuptake at the NET.

Figure 15:
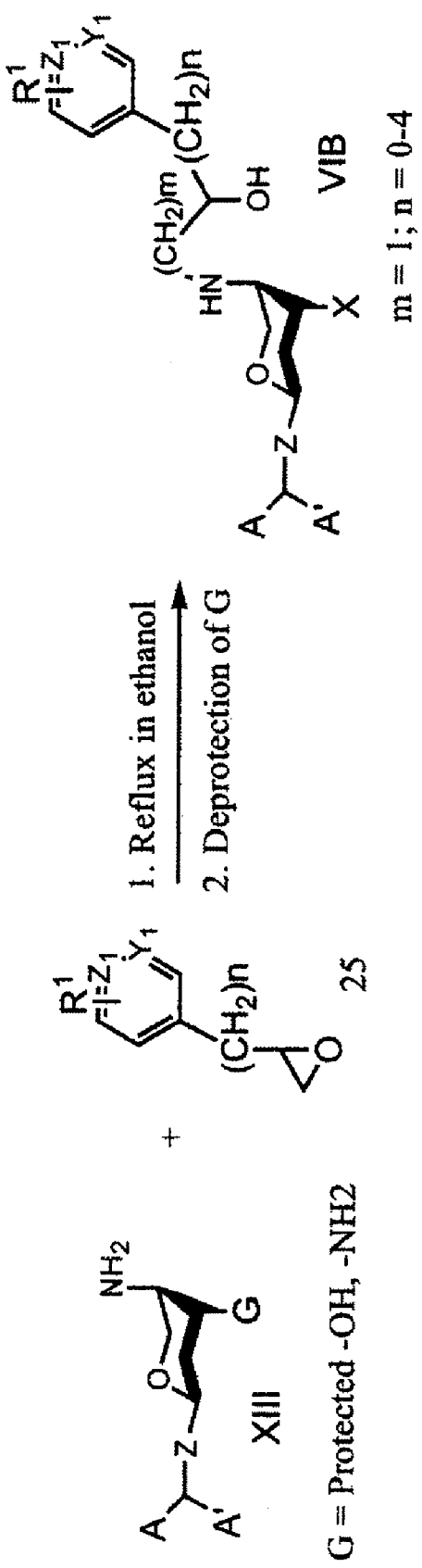
FIG. 15 provides a scheme for the preparation of compounds having formula VIb.

FIG. 15 provides a scheme for the preparation of compounds having formula VIb. Preparation of compounds having formulae VIa, VIc, and VId is accomplished by analogous methodology.

Figure 16A:
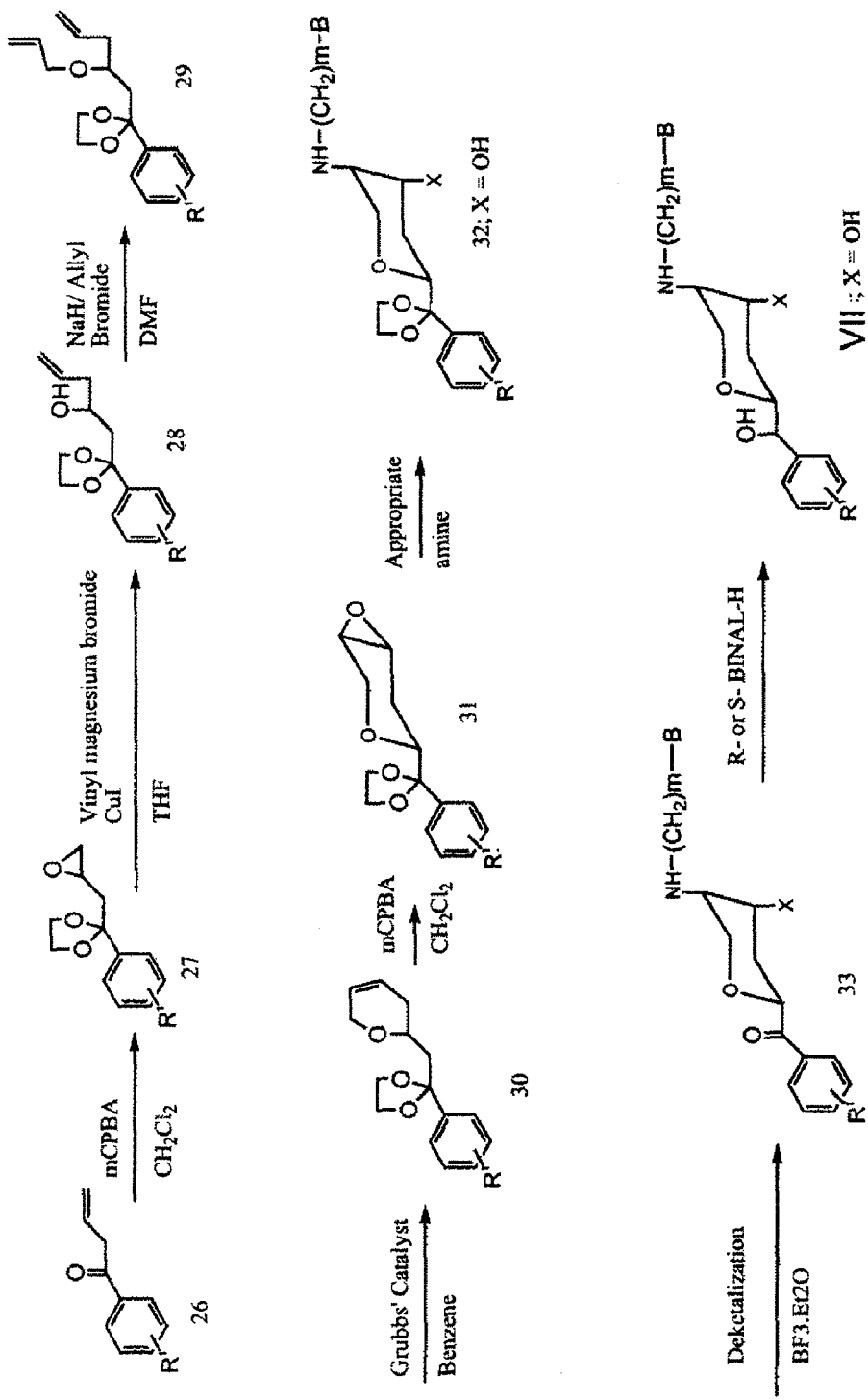
FIGS. 16A and 16B provide schema for the preparation of compounds having formula VII.
Figure 16B:
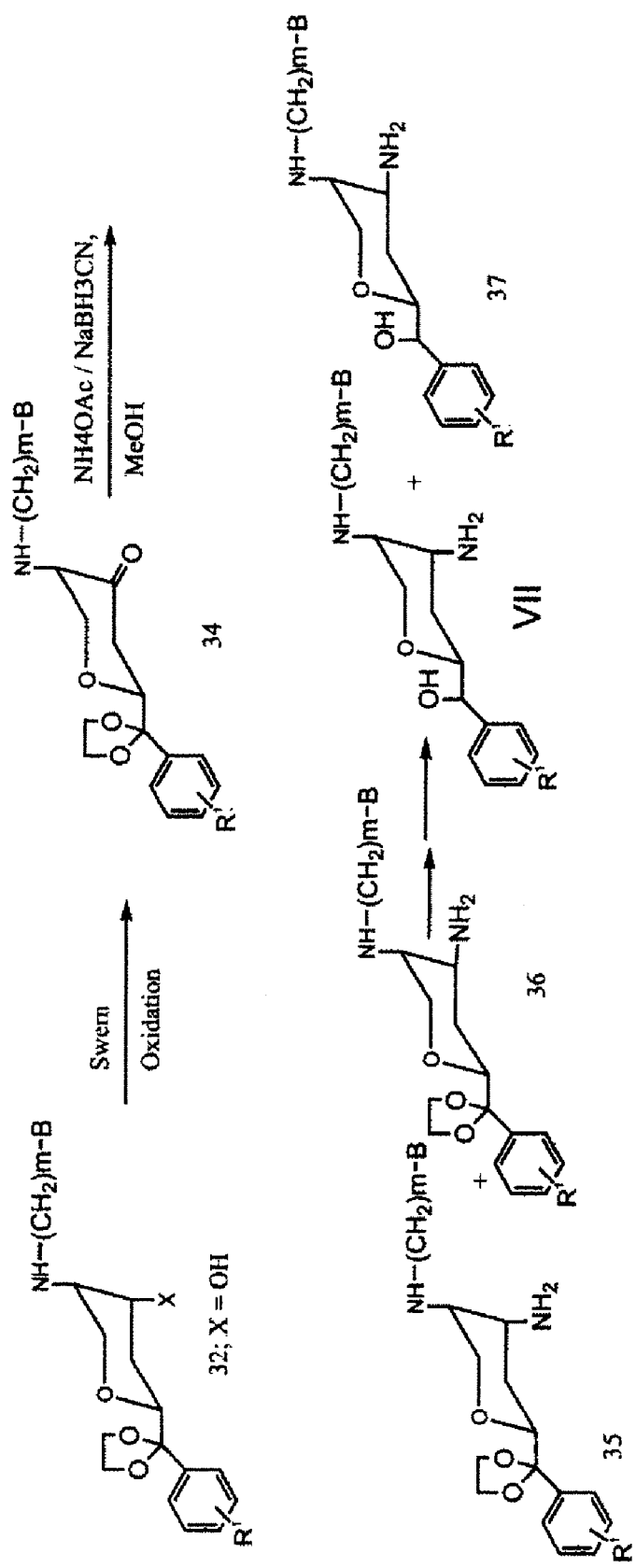

FIGS. 16A and 16B provide a scheme for the preparation of compounds having formula VII. Appropriate starting material 26 is converted into intermediate 31. Epoxide ring opening followed by deketalization produces intermediate 33. Chiral reduction is next provide asymmetric target compounds.

Figure 17:
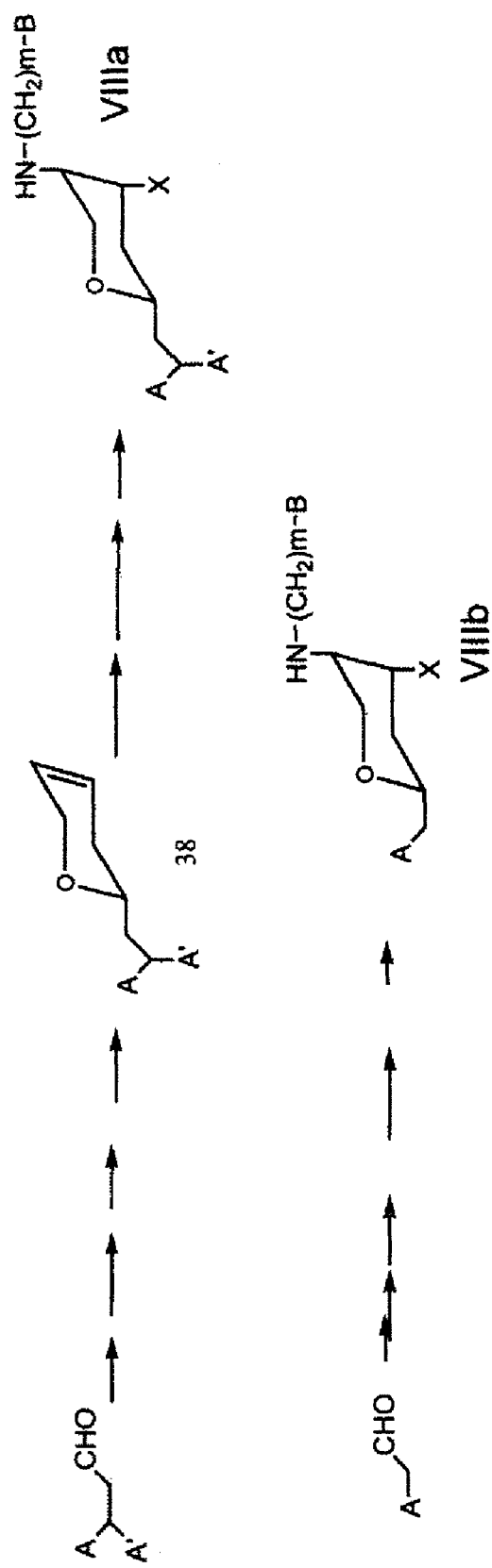
FIG. 17 provides a scheme for the preparation of compounds having formulae VIIIa and VIIIb.

FIG. 17 provides a scheme for the preparation of compounds having formulae VIIa and VIIIb.

Figure 18:
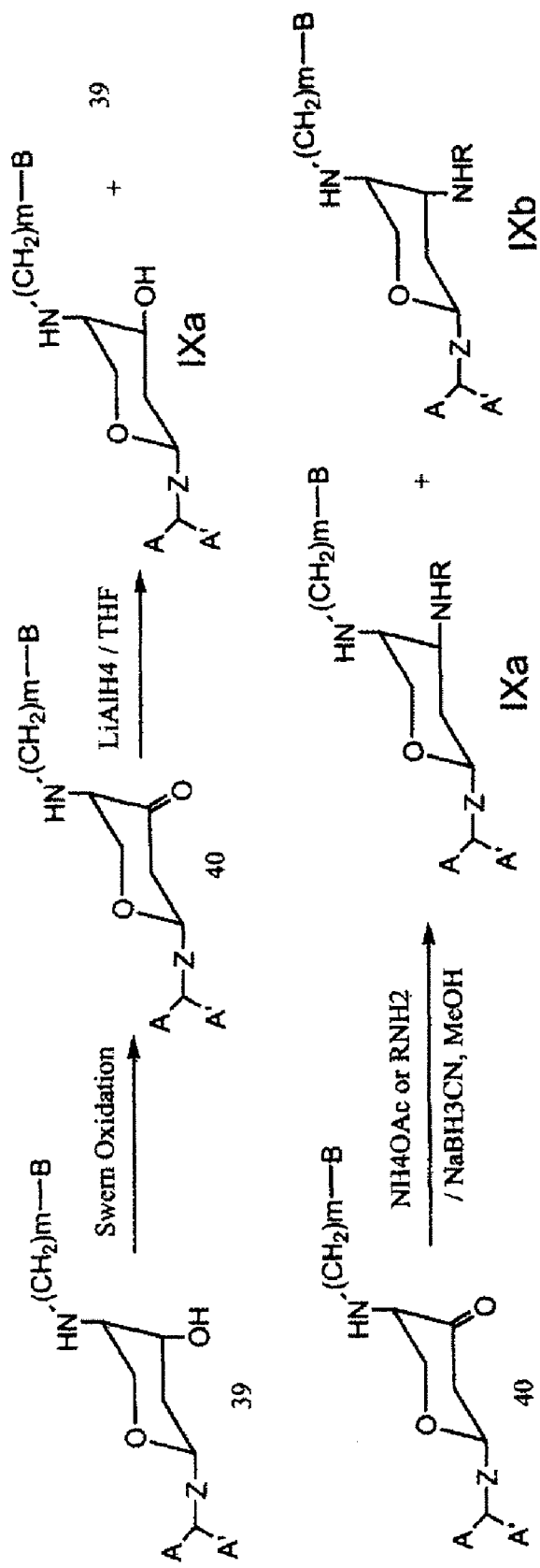
FIG. 18 provides a scheme for the preparation of compounds having formulae IXa and IXb.

FIG. 18 provides a scheme for the preparation of compounds having formulae IXa and IXb. The synthesis will start from a suitable starting material represented by structure 39.

Experimental Details

Reagents and solvents were obtained from commercial suppliers and used as received unless otherwise indicated. Dry solvent was prepared according to the standard procedure as described by Vogel. All reactions were performed under inert atmosphere ($N_2$) unless otherwise noted. Analytical silica gel-coated TLC plates (Si 250F) were purchased from Baker, Inc. and were visualized with UV light or by treatment with phosphomolybdic acid (PMA). Flash chromatography was carried out on Baker Silica Gel 40 mM. $^1$H NMR spectra were routinely obtained with GE300 MHz and 400 MHz FT NMR. The NMR solvent used was $CDCl_3$ as indicated. TMS was used as an internal standard. Elemental analyses were performed by Atlantic Microlab, Inc and were within ±0.4% of the theoretical value, but are not reported herein for reasons of brevity.

[$^3$H]WIN 35,428 (86.0 Ci/mmol), [$^3$H]nisoxetine (80.0 Ci/mmol) and [$^3$H]dopamine (48.2 Ci/mmol) were obtained from Dupont-New England Nuclear (Boston, Mass., U.S.A.). [$^3$H]citalopram (85.0 Ci/mmol) was from Amersham Pharmacia Biotech Inc. (Piscataway, N.J., U.S.A.). Cocaine hydro-chloride was purchased from Mallinckrodt Chemical Corp. (St. Louis, Mo., U.S.A.). WIN 35,428 napthalene sulfonate was purchased from Research Biochemicals, Inc. (Natick, Mass., U.S.A.). (−)-Cocaine HCl was obtained from the National Institute on Drug Abuse. GBR 12909 Dihydrochloride (1-[2-[bis(4-Fluorophenyl)-methoxy]ethyl]-4-[3-phenylpropyl]piperazine) was purchased from SIGMA-ALDRICH (#D-052; St. Louis, Mo.).

Synthesis of
2-benzhydryl-2,3-dihydro-4H-pyran-4-one (2)

A solution of boron trifluoride diethyl etherate (7.8 g, 55 mmol) in dry ether (50 ml) was added to a stirred mixture of E-1-methoxy-3-trimethylsilyloxybuta-1,3-diene (8.3 g, 48 mmol), diphenylacetaldehyde 1 (11.4 g, 58 mmol) and dry ether (300 ml) cooled to −78° C. After one hour, the mixture was allowed to reach 0° C. for three hours. The deep red reaction mixture was quenched with saturated aqueous NaHCO$_3$, and the mixture was allowed to come to room temperature. The organic phase was separated and the aqueous phase was extracted with ether (3×70 ml). The combined organic phases were washed with brine, and dried over anhydrous Na$_2$SO$_4$. Evaporation of solvent under reduced pressure and purification of the crude product by chromatography (hexane/ethyl acetate 8:2) gave 2-diphenylmethyl-2,3-dihydro-4H-pyran-4-one 2 (10.2 g, 80.2%, yield) as a yellow solid.

$^1$H NMR (400 Mhz, CDCl$_3$) 2.38 (dd, J=3.2 Hz, 16.8 Hz, 1H, H-3) 2.51 (m, 1H, H-3) 4.23 (d, J=9.2 Hz, 1H, (Ph)$_2$CH) 5.15 (dt, J=3.2 Hz, 8.8 Hz, 1H, H-2) 5.44 (d, J=6.4 Hz, 1H, H-5), 7.16-7.38 (m, 1H, H-6, aromatic-CH).

Synthesis of Cis and Trans-2-benzhydryl-tetrahydropyran-4-ol 3a and 3b

NaCNBH$_3$ (0.75 g, 12 mmol) was added portionwise to a mixture of 2-diphenylmethyl-2,3-dihydro-4H-pyran-4-one 2 (1.05 g, 4 mmol) and boron trifluoride etherate (1.99 g, 14 mmol) in dry THF (50 ml) cooled to −78° C. The reaction mixture was allowed to reach room temperature and the reaction was quenched with saturated aqueous NaHCO$_3$ (30 ml). The organic phase was separated, and the aqueous phase was extracted with ethyl ether (3×20 ml). The organic phases were combined and dried over anhydrous Na$_2$SO$_4$. Removal of the solvent under reduced pressure, and purification by flash chromatography (hexane/ethyl acetate 7:3) first afforded trans-2-benzhydryl-tetrahydropyran-4-ol 3a (0.73 g, 68% yield).

$^1$H NMR (400 MHz, CDCl$_3$) 1.22 (q, J=12 Hz, 1H, H-3ax) 1.46 (dq, J=4.8 Hz, 12 Hz, 1H, H-5ax) 1.74-1.86 (m, 2H, H-3 eq, H-5 eq) 3.40 (dt, J=2 Hz, 12 Hz, 1H, H-6ax) 3.707 (m, 1H, H-4) 3.941-4.039 (m, 2H, H-6 eq, (Ph)$_2$CH)7.15-7.4 (m, 10H, aromatic-CH).

Eluted second was cis-2-benzhydryl-tetrahydropyran-4-ol, 3b (0.3 g, 28.1% yield).

$^1$H NMR (400 MHz, CDCl$_3$) 1.5-1.58 (m, 4H, H-3, H-5 eq, OH)1.84 (m, 1H, H-5ax) 3.79 (m, 1H, H-6 eq) 3.876 (d, J=8.8 Hz, (Ph)$_2$CH) 3.908 (dt, J=3.2 Hz, 111.2 Hz, 1H, H-6ax) 4.184 (m, 1H, H-4 eq) 4.524 (dt, J=4 Hz, 8.8 Hz, 1H, H-2) 7.16-7.38 (m, 10H, aromatic-CH).

Procedure A

Synthesis of methanesulfonic acid Trans-2-benzhydryl-tetrahydropyran-4-yl ester 4a Methanesulfonyl chloride (0.62 g, 5.41 mmol) in dry methylene chloride (10 ml) was added dropwise to a mixture of trans-2-diphenylmethyl-4-hydroxypyran 3a (0.73 g, 2.70 mmol), triethylamine (0.41 g, 4.06 mmol) in methylene chloride (10 ml) and was cooled to 0° C. After one hour, the reaction was gradually allowed to reach room temperature over a period of four hours. Additional methylene chloride (20 ml) was added to the reaction mixture, and the mixture was washed in turn with saturated aqueous sodium bicarbonate, brine and water, then dried over anhydrous sodium sulfate. The solvent was removed under reduced pressure, and purification by flash chromatography gave compound 4a (0.93 g, 99.9% yield) as an oil.

$^1$H NMR (300 mHz, CDCl$_3$): 1.54 (m, 1H, H-3ax) 1.82 (m, 1H, H-5ax) 1.95 (m, 1H, H-3 eq) 2.1 (m, 1H, H-5 eq) 2.95 (s, 3H, CH$_3$SO$_2$) 3.46 (dt, 1H, H-6ax) 3.96 (d, 1H, (Ph)$_2$CH) 4.1 (m, 2H, H-2, H-6 eq) 4.83 (m, 1H, H-4) 7.15-7.38 (m, 10H, aromatic-CH).

Synthesis of methanesulfonic acid cis-2-benzhydryl-tetrahydropyran-4-ylester 4b Cis-2-diphenylmethyl-4-hydroxy-pyran 3b (0.3 g, 1.12 mmol) was reacted with methanesulfonyl chloride (0.26 g, 2.24 mmol) (Procedure A) to give compound 4b (0.38 g, 98%) as an oil.

$^1$H NMR (300 MHz, CDCl$_3$): 1.609 (m, 1H, H-3ax) 1.8-1.96 (m, 4H, —OH, H-3 eq, H-5) 2.96 (s, 3H, CH$_3$SO$_2$) 3.8-3.94 (m, 3H, H-6, (Ph)$_2$CH)4.46 (dt, J=2 Hz, 10 Hz, 1H, H-2) 5.1 (m, 1H, H-4) 7.16-7.38 (m, 10H, aromatic-CH).

Procedure B

Synthesis of cis azido-2-benzhydryl-tetrahydropyran (5a)

Into a solution of trans-2-diphenylmethylpyran-4-yl methanesulfonate 4a (0.33 g, 0.95 mmol) in dry DMF (40 ml) was added sodium azide (0.18 g, 2.85 mmol). The mixture was heated to 100° C. and stirred for 4 hr. The mixture was diluted with ethyl ether, washed with 2M aqueous NaHCO$_3$ and brine, and then dried over anhydrous Na$_2$SO$_4$. Removal of the solvent and purification by flash chromatography (Hexane/Ethyl Acetate 9:1) afforded compound 5a (0.23 g, 82.7% yield) as a liquid.

$^1$H NMR (400 MHz, CDCl$_3$) 1.5-1.68 (m, 3H, H-3, H-5 eq)1.855 (m, 1H, H-5ax) 3.74-3.86 (m, 2H, H-6) 3.87 (d, J=9.2 Hz, 1H, (Ph)$_2$CH)4.02 (m, 1H, H-4) 4.393 (dt, J=3.2 Hz, 13 Hz, 1H, H-2) 7.16-7.38 (m, 10H, aromatic-CH).

Synthesis of trans 4-azido-2-benzhydryl-tetrahydropyran 5b

Cis-2-diphenylmethylpyran-4-yl methanesulfonate 4b (0.38 g, 1.10 mmol) was reacted with sodium azide (0.29 g, 4.4 mmol) in dry DMF (Procedure B) to yield compound 5b (0.26 g, 80%) as a liquid.

$^1$H NMR (500 MHz, CDCl$_3$) 1.32 (q, J=11 Hz, 1H, H-3ax) 1.61 (dq, J=5.5 Hz, 13 Hz, 1H, H-5ax) 1.82 (m, 1H, H-3 eq) 1.90 (m, 1H, H-5 eq) 3.44-3.50 (m, 2H, H-4, H-6ax) 3.96 (d, J=8.5 Hz, 1H, (Ph)$_2$CH) 4.03 (dt, J=2 Hz, 9 Hz, 1H, H-2) 4.08 (ddd, J=2 Hz, 5.5 Hz, 12.5 Hz, 1H, H-6 eq) 7.16-7.38 (m, 10H, aromatic-CH).

Procedure C

Synthesis of cis-(2-benzhydryl-tetrahydropyran-4-yl)-amine (6a)

Cis-4-azido-2-diphenylmethyltetrahydropyran 5a (0.23 g, 0.78 mmol) was hydrogenated (60 psi) in the presence of 10% Pd—C (0.02 g, 10% wt) for 4 hr. The reaction mixture was filtered through a short bed of celite, and removal of the solvent afforded 0.21 g (quantitative yield) of product. This product was pure enough to continue to the next reaction step.

$^1$H NMR (300 MHz, CDCl$_3$) 1.21-1.4 (m, 4H, H-3, NH$_2$) 1.59 (m, 1H, H-Sax) 1.87 (m, 1H, H-5 eq) 3.37 (m, 1H, H-4) 3.77 (m, 1H, H-6 eq) 3.91 (dt, J=2.4 Hz, 11.7 Hz, 1H, H-6ax)

3.94 (d, J=9.3 Hz, 1H, (Ph)$_2$CH) 4.56 (dt, J=2.4 Hz, 10.2 Hz, 1H, H-2) 7.16-7.38 (m, 10H, aromatic-CH).

Synthesis of Trans-(2-benzhydryl-tetrahydropyran 11)-amine (6b)

Trans-4-azido-2-diphenylmethyltetrahydropyran 5b (0.26 g, 0.89 mmol) was hydrogenated (Procedure C) to yield compound 6b (0.24 g, quantitative).

$^1$H NMR (400 MHz, CDCl$_3$) 1.15-1.25 (m, 1H, H-3) 1.4-1.52 (m, 1H, H-3) 1.7-1.88 (m, 2H, H-5) 2.99 (m, 1H, H-4) 3.41 (dt, J=2 Hz, 12.4 Hz, 1H, H-6ax) 3.9-4.06 (m, 3H, H-2, H-6ax, (Ph)$_2$CH) 4.7 (bs, 2H, NH$_2$) 7.16-7.38 (m, 10H, aromatic-CH).

Procedure D

Synthesis of cis-(2-benzhydryl-tetrahydropyran 4-yl)-(4-fluorobenzyl)-amine (7a)

To a solution of cis-4-amino-2-diphenylmethylpyran 6a (0.2 g, 0.75 mmol), 4-fluorobenzaldehyde (0.83 g, 0.67 mmol) and glacial acetic acid (0.45 g, 0.75 mmol) in 1,2-dichloroethane (20 ml), was added portion wise NaCNBH$_3$ (0.57 g, 0.9 mmol) dissolved in methanol (5 ml). After 4 hr, water was added to quench the reaction and the mixture was stirred for 30 minutes at 0° C. Then the mixture was made basic with saturated aqueous NaHCO$_3$ and extracted thrice with methylene chloride (3×30 ml). The combined organic phases were washed with brine, water and dried over anhydrous Na$_2$SO$_4$. Solvent was removed in vacuo to collect the crude residue, which was purified by flash chromatography (Hexane/Ethyl Acetate/Triethylamine 3:2:0.2) to give cis-2-diphenylmethyl-4-(4-fluorobenzylamino)-tetrahydropyran 7a (0.20 g, 72.6%) as a liquid.

$^1$H NMR (400 MHz, CDCl$_3$) 1.24 (bs, 1H, —NH) 1.28 (m, 1H, H-3)1.45-1.58 (m, 2H, H-3, H-5 eq) 1.83 (tt, J=4 Hz, 13 Hz, 1H, H-5ax) 3.07 (m, 1H, H-4) 3.65 (s, 2H, (F)Ph-CH$_2$) 3.75 (m, 1H, H-6 eq) 3.91 (d, J=9.6 Hz, 1H, (Ph)$_2$CH) 3.94 (dt, J=2.4 Hz, 12 Hz, 1H, H-6ax) 4.59 (dt, J=3.2 Hz, 9.6 Hz, 1H, H-2) 6.9-7.4 (m, 14H, aromatic-CH).

The free base 7a was converted into its oxalate salt: mp 177-181° C. C,H,N Anal: [C$_{25}$H$_{26}$NOF.(COOH)].

Synthesis of trans-(2-benzhydryl-tetrahydropyran-4-yl)-(4-fluoro-benzyl)-amine 7b trans-4-Amino-2-diphenylmethyl pyran 6b (0.24 g, 0.90 mmol) was reacted with 4-fluorobenzaldehyde (0.11 g, 0.90 mmol) in presence of acetic acid (0.05 g, 0.9 mmol), and then reduced with NaCNBH$_3$ (0.07 g, 1.08 mmol) to yield compound 7b (0.18 g, 54%) (Procedure D).

$^1$H NMR (500 MHz, CDCl$_3$) 1.13 (q, J=10.5 Hz, 1H, H-3ax)1.32 (broad, NH) 1.38 (dq, J=5 Hz, 12.5 Hz, 1H, H-5ax) 1.74 (m, 1H, H-3 eq)1.87 (m, 1H, H-5 eq) 2.722 (tt, J=4 Hz, 11.5 Hz, 1H, H-4) 3.444 (dt, J=2 Hz, 12 Hz, 1H, H-6ax) 3.683 (d, J=13.5 Hz, 1H, (F)Ph-CH) 3.754 (d, J=13 Hz, 1H, (F)Ph-CH) 3.936 (d, J=9 Hz, 1H, (Ph)$_2$CH) 4.0-4.08 (m, 2H, H-2, H-6 eq) 6.9-7.38 (m, 14H, aromatic-CH).

Free base was converted into its oxalate salt: mp 185-187° C. C,H,N Anal: [C$_{25}$H$_{26}$NOF.(COOH)].

Synthesis of 1,1-diphenyl-hex-5-en-2-ol (8)

A dry three-neck, round-bottom flask fitted with a reflux condensor, air-balance drop funnel and nitrogen inlet was charged with Mg (0.11 g, 4.44 mmol) and a crystal of I$_2$. The flask was warmed (heat gun) to volatilize the I$_2$ under vacuum, and then was allowed to cool. Dry ethyl ether (10 ml) was added next followed by introduction of catalytic neat 4-bromo-1-butene (0.02 g). The reaction was initiated by brief warming and then the rest of total amount of bromide (0.4 g, 2.96 mmol) in dry ethyl ether (5 ml) was added dropwise over 5 minutes. The mixture was refluxed for 30 minutes and then was allowed to reach 0° C. Into the stirred Grignard reagent solution was added dropwise a solution of diphenylacetaldehyde 1 (0.64 g, 3.26 mmol) in dry ethyl ether (5 ml), and the reaction mixture was stirred for an additional 3.5 hr at room temperature. Saturated aqueous NaHCO$_3$ was added to the reaction mixture at 0° C., the organic phase was separated and the aqueous phase was extracted with ethyl ether (3×20 ml). The combined organic phases were washed with brine and water, then dried over anhydrous Na$_2$SO$_4$. The solvent was removed under reduced pressure, and flash chromatography of the crude residue (SiO$_2$, hexane/Ethyl Acetate 9:1) gave 1,1-diphenyl-hex-5-en-2-ol 8 (0.68 g, 91%) as a liquid.

$^1$H NMR (400 MHz, CDCl$_3$) 1.45-1.70 (m, 2H, H-3) 1.69 (bd, —OH)2.1-2.4 (m, 2H, H-4) 3.91 (d, J=8.4 Hz, 1H, H-1) 4.39 (m, 1H, H-2) 4.95-5.1 (m, 2H, H-6) 5.81 (m, 1H, H-5) 7.16-7.38 (m, 10H, aromatic-CH).

Synthesis of 1,1-diphenyl-2-(1-ethenoxy)-hex-5-ene (9)

Into a mixture of 1,1-diphenyl-hex-5-en-2-ol 2 (7 g, 27.78 mmol) in ethyl vinyl ether (250 ml) was added Hg(OCOCF$_3$)$_2$ (2.37 g, 5.56 mmol) and was stirred overnight at room temperature. The reaction mixture was neutralized by addition of sat. aqueous NaHCO$_3$. The organic phase was separated and the aqueous layer was extracted with ethyl ether, and dried over anhydrous Na$_2$SO$_4$. Removal of the solvent and purification by flash chromatography (Hexane/Ethyl Acetate 20:1) gave 1,1-diphenyl-2-(1-ethenoxy)-hex-5-ene 9 (5.1 g, 66%) as a liquid.

$^1$H NMR (400 MHz, CDCl$_3$) 1.58-1.78 (m, 2H, H-3) 2.08-2.30 (m, 2H, H-4) 3.86 (dd, J=1.6 Hz, 8.4 Hz, 1H, H-2') 4.15 (d, J=8 Hz, 1H, Ph$_2$CH)4.25 (dd, J=1.6 Hz, 14 Hz, 1H, H-2') 4.50 (m, 1H, H-2) 5.00 (m, 2H, H-6)5.77 (m, 1H, H-5) 6.15 (dd, J=6.8 Hz, 14.8 Hz, 1H, H-1') 7.16-7.38 (m, 10H, aromatic-CH).

Synthesis of 2-benzhydryl-3,4-dihydro-2H-pyran (10)

A solution of 1,1-diphenyl-2-(1-ethenoxy)-hex-5-ene 9 (5.1 g, 18.3 mmol) and Grubb's catalyst (1.5 g, 1.83 mmol) in benzene (200 ml) was heated under reflux for 20 hr. The solvent was removed under vacuo and the residue was chromatographed over silica gel (Hexane/Ethyl Acetate 20:1) to give 2-diphenyl-3,4-dihydro-2H-pyran 10 (4.25 g, 92.6%) as a liquid.

$^1$H NMR (400 MHz, CDCl$_3$) 1.52-1.66 (m, 1H, H-3) 1.76-1.84 (m, 1H, H-3) 1.92-2.14 (m, 2H, H-4) 4.08 (d, J=9.2 Hz, 1H, Ph$_2$CH) 4.59 (dt, J=2.4 Hz, 8.8 Hz, 1H, H-2) 4.72 (m, 1H, H-5) 6.38 (d, J=6.4 Hz, 1H, H-6) 7.16-7.50 (m, 10H, aromatic-CH).

Synthesis of Trans-6-benzhydryl-tetrahydropyran-3-ol (11)

Into a solution of 0.5M 9-BBN-THF complex (24 ml, 12 mmol) in dry THF (20 ml) was added in a drop wise manner 2-diphenyl-3,4-dihydro-2H-pyran 10 (1 g, 4 mmol) dissolved in dry THF (10 ml). The mixture was kept under stirring at room temperature. After the completion of initial addition reaction, the intermediate reaction mixture was oxidized with 5.3 ml 3N sodium hydroxide and 3 ml of 30% hydrogen peroxide. The reaction was continued at 55° C. for 1 hr to insure the completion of oxidation. After the mixture was diluted with sat. aqueous $NaHCO_3$, the organic layer was separated, and the aqueous layer was extracted with ethyl acetate (3×40 ml). The combined extract was dried over anhydrous $Na_2SO_4$. The solvent was removed in vacuo and the crude product was purified by flash chromatography (Hexane/Ethyl Acetate 7:3) to furnish trans-6-diphenyltetrahydropyran-3-ol 11 (1 g, 93.5%) as a liquid.

$^1$H NMR (300 MHz, $CDCl_3$) 1.32-1.44 (m, 2H, H-5) 1.54-1.64 (m, 1H, H-4) 1.75 (bs, 1H, OH) 2.02-2.14 (m, 1H, H-4) 3.14 (t, J=10.2 Hz, 1H, H-2ax) 3.67 (m, 1H, H-3) 3.90 (d, J=9.3 Hz, 1H, $Ph_2CH$) 3.95-4.04 (m, 2H, H-2 eq, H-6) 7.16-7.38 (m, 10H, aromatic-CH).

Synthesis of 6-benzhydryl-dihydropyran-3-one (12)

Into a solution of DMSO (0.13 g, 1.64 mmol) in methylene chloride (5 ml) at −78° C. was added a solution of oxalyl chloride (0.11 g, 0.82 mmol) in methylene chloride (1 ml) in a dropwise manner. A solution of trans-2-diphenylmethyl-tetrahydropyran-5-ol 11 (0.2 g, 0.75 mmol) in methylene chloride (2 ml) was added next. The reaction was continued for 15 minutes, triethylamine (0.38 g, 3.73 mmol) was next added portion wise and the reaction mixture was allowed to come to room temperature for over a period of 30 minutes. Additional methylene chloride (10 ml) was added, and washed with sat. aqueous $NaHCO_3$, brine, and then dried over anhydrous $Na_2SO_4$. Removal of the solvent and purification by flash chromatography ($SiO_2$, Hexane/Ethyl Acetate 8.5:1.5) gave 2-diphenylmethyl-dihydro-pyran-5-one 12 (0.18 g, 91%) as a liquid.

$^1$H NMR (300 MHz, $CDCl_3$) 1.9-1.98 (m, 2H, H-5) 2.38-2.62 (m, 2H, H-4) 4.0 (d, J=17.1 Hz, 1H, H-2) 4.05 (d, J=9 Hz, 1H, $Ph_2CH$) 4.17 (dd, J=1.8 Hz, 16.2 Hz, 1H, H-2) 4.44 (dt, J=5.2 Hz, 8.4 Hz, 1H, H-6) 7.16-7.38 (m, 10H, aromatic-CH).

$^{13}$C NMR (75 MHz, $CDCl_3$) (ppm) 21.50, 32.00, 55.72, 65.62, 76.05, 126.89, 127.09, 128.60, 128.68, 128.90, 128.97, 141.36, 141.62, 146.77.

Synthesis of Trans-(6-benzhydryl-tetrahydropyran-3-yl)-(34-fluorobenzyl)-amine (16a)

2-diphenylmethyl-dihydropyran-5-one 12 (0.18 g, 0.68 mmol) was reacted with 4-fluorobenzylamine (0.08 g, 0.68 mmol) in the presence of glacial acetic acid (0.041 g, 0.68 mmol) in 1,2-dichloroethane (10 ml) at room temperature, and then reduced by $NaCNBH_3$ (0.051 g, 0.81 mmol) (Procedure D) to yield a mixture of 16a and 16b. cis-2-Diphenylmethyl-5-(4-fluorobenzylamino)-tetrahydropyran 16b eluted first (0.04 g, 15%).

$^1$H NMR (300 MHz, $CDCl_3$) 1.33 (m, 1H, H-5) 1.46-1.72 (m, 2H, H-5, H-4) 1.935 (m, 1H, H-4) 2.031 (bm, 1H, NH) 2.641 (m, 1H, H-3) 3.571 (dd, J=1.8 Hz, 11.4 Hz, 1H, H-2ax) 3.75 (m, 2H, (F)Ph-$CH_2$) 3.95-4.14 (m, 3H, H-6, H-2 eq, $Ph_2CH$) 6.9-7.38 (m, 14H, aromatic-CH).

Free base 16b was converted into oxalate: mp 229-230° C. C,H,N Anal: [$C_{25}H_{26}NOF.(COOH)$].

Eluted second was trans-2-diphenylmethyl-5-(4-fluorobenzylamino)-tetrahydropyran 16a (0.11 g, 45%).

$^1$H NMR (300 MHz, $CDCl_3$) 1.24-1.44 (m, 2H, H-5) 1.55 (m, 1H, H-4) 1.748 (bm, NH) 2.02 (m, 1H, H-4) 2.68 (m, 1H, H-3) 3.11 (t, J=10.8 Hz, 1H, H-2ax) 3.76 (s, 2H, (F)-Ph-$CH_2$) 3.89 (d, J=9 Hz, 1H, $Ph_2CH$) 3.99 (dt, J=3 Hz, 8.7 Hz, 1H, H-6) 4.08 (m, 1H, H-2 eq) 6.9-7.38 (m, 14H, aromatic-CH).

Free base 16a was converted into the oxalate: mp 141-143° C. C,H,N Anal: [$C_{25}H_{26}NOF.(COOH)_2$ $0.65H_2O$].

Synthesis of Methanesulfonic Acid trans-6-benzhydryl-tetra-hydropyran-3-yl ester (13)

Methanesulfonyl chloride (0.33 g, 2.87 mmol) was reacted with trans-2-diphenylmethyl-tetrahydropyran-5-ol 11 (0.38 g, 1.43 mmol) in the presence of triethylamine (0.22 g, 2.15 mmol) in methylene chloride (10 ml) to give trans-2-diphenylmethyl-tetrahydropyran-5-yl methanesulfonate 13 (0.39 g, 77.8%) as an oil (Procedure A).

$^1$H NMR (400 MHz, $CDCl_3$) 1.47 (m, 1H, H-5) 1.62-1.78 (m, 2H, H-5, H-4) 2.25 (m, 1H, H-4) 2.96 (s, 3H, $CH_3SO_2$) 3.36 (t, J=10.4 Hz, 1H, H-2ax) 3.89 (d, J=8.8 Hz, 1H, $Ph_2CH$) 4.00 (dt, J=2 Hz, 9.6 Hz, 1H, H-6) 4.14 (m, 1H, H-2 eq) 4.61 (m, 1H, H-3) 7.16-7.38 (m, 10H, aromatic-CH).

Synthesis of Cis-3-azido-6-benzhydryl-tetrahydropyran (14)

Trans-2-diphenylmethyl-tetrahydropyran-5-yl methanesulfonate 13 (0.39 g, 1.12 mmol) in dry DMF (50 ml) was reacted with sodium azide (0.22 g, 3.35 mmol) to yield cis-5-azido-2-diphenylmethyl-tetrahydropyran 14 (0.3 g, 92%) as an oil (Procedure B).

$^1$H NMR (300 MHz, $CDCl_3$) 1.36 (m, 1H, H-5) 1.54-1.85 (m, 2H, H-5, H-4) 1.98 (m, 1H, H-4), 3.55 (m, 1H, H-3), 3.64 (dd, J=1.18 Hz, 12.6 Hz, 1H, H-2) 3.95-4.15 (m, 3H, H-2, H-6, $Ph_2CH$) 7.16-7.38 (m, 10H, aromatic-CH).

Synthesis of Cis-(6-benzhydryl-tetrahydropyran-3-yl)-amine (15)

Cis-5-azido-2-diphenylmethyl-tetrahydropyran 14 (0.3 g, 1.02 mmol) in methanol (25 ml) was hydrogenated under the catalyst of 10% Pd—C (0.03 g, 10% wt) for 4 hr (Procedure C) to give cis-5-amino-2-diphenylmethyl-tetrahydropyran 15 (0.21 g, 78%) as an oil.

$^1$H NMR (400 MHz, $CD_3OD$) 1.31 (m, 1H, H-5eq) 1.54 (m, 1H, H-5ax) 1.70-1.86 (m, 2H, H-4) 2.90 (bs, bs, 1H, H-3) 3.68 (m, 2H, H-2) 3.96 (d, J=9.2 Hz, 1H, $Ph_2CH$) 4.13 (dt, J=2 Hz, 9.6 Hz, 1H, H-6) 7.10-7.40 (m, 10H, aromatic-CH). Free base 15 was converted to the HCl salt: mp 260-261° C. C,H,N Anal: [$C_{18}H_{21}NO.HCl$ $0.2H_2O$].

Synthesis of Cis-(6-benzhydryl-tetrahydropyran-3-yl)-(4-fluoro-benzyl)-amine (16b)

Trans-5-amino-2-diphenylmethyl-tetrahydropyran 15 (0.21 g, 0.79 mmol) was reacted with 4-fluorobenzaldehyde (0.098 g, 0.79 mmol) in the presence of glacial acetic acid (0.047 g, 0.79 mmol) in 1,2-dichloroethane (20 ml), and then reduced by $NaCNBH_3$ (0.059 g, 0.95 mmol) in methanol (5 ml) (Procedure D) to give compound 16b (0.24 g, 82%).

$^1$H NMR (300 MHz, $CDCl_3$) 1.33 (m, 1H, H-5) 1.46-1.72 (m, 2H, H-5, H-4) 1.935 (m, 1H, H-4) 2.031 (bm, 1H, NH) 2.641 (m, 1H, H-3) 3.571 (dd, J=1.8 Hz, 11.4 Hz, 1H, H-2ax) 3.75 (m, 2H, (F)Ph-$CH_2$) 3.95-4.14 (m, 3H, H-6, H-2 eq, $Ph_2CH$) 6.9-7.38 (m, 14H, aromatic-CH).

Free base 16b was converted into the oxalate: mp 229-230° C. C,H,N Anal: [$C_{25}H_{26}NOF.(COOH)_2$].

Synthesis of Cis-(6-benzhydryl-tetrahydropyran-3-yl)-(4-cyano-benzyl)-amine (16c)

Trans-5-amino-2-diphenylmethyl-tetrahydropyran 15 (0.15 g, 0.56 mmol) was reacted with 4-cyanobenzaldehyde (0.07 g, 0.56 mmol) in the presence of glacial acetic acid (0.033 g, 0.56 mmol) in 1,2-dichloroethane (20 ml), and NaCNBH$_3$ (0.042 g, 0.67 mmol) in methanol (5 ml) (Procedure D) to give compound 16c (0.17 g, 80%) as an oil.

$^1$H NMR (300 MHz, CDCl$_3$) 1.36 (m, 1H, H-5) 1.46-1.58 (m, 1H, H-5) 1.58-1.74 (m, 1H, H-4) 1.931 (m, 1H, H-4) 2.615 (bm, 1H, H-3) 3.59 (dd, J=1.8 Hz, 11.7 Hz, H-2ax) 3.83 (m, 2H, (CN)Ph-CH$_2$) 3.95-4.16 (m, 3H, H-6, H-2 eq, Ph$_2$CH) 7.16-7.62 (m, 14H, aromatic-CH). Free base 16c was converted into the oxalate: mp 241-242° C. C,H,N Anal: [C$_{26}$H$_{26}$N$_2$O(COOH)].

Synthesis of Cis-(6-benzhydryl-tetrahydropyran-3-yl)-(4-nitro-benzyl)-amine (16d)

Trans-5-amino-2-diphenylmethyl-tetrahydropyran 15 (0.1 g, 0.38 mmol) was reacted with 4-nitrobenzaldehyde (0.057 g, 0.38 mmol) in the presence of glacial acetic acid (0.023 g, 0.38 mmol) in 1,2-dichloroethane (20 ml), and then reduced by NaCNBH$_3$ (0.03 g, 0.45 mmol) in methanol (5 ml) (Procedure D) to give compound 16d (0.12 g, 80%) as an oil.

$^1$H NMR (300 MHz, CDCl$_3$) 1.35 (m, 1H, H-5) 1.53 (m, 1H, H-5)1.67 (tt, J=3.6 Hz, 13.5 Hz, 1H, H-4) 1.91 (m, 2H, H-4, NH) 2.62 (m, 1H, H-3)3.58 (dd, J=1.8 Hz, 9.6 Hz, 1H, H-2ax) 3.87 (m, 2H, (NO$_2$)Ph-CH$_2$) 3.92-4.14 (m, 3H, H-6, H-2 eq, Ph$_2$CH) 7.14-7.54, 8.12-8.2 (m, 14H, aromatic-CH). Free base 16d was converted into the oxalate: mp 236-238° C. C,H,N Anal: [C$_{25}$H$_{26}$N$_2$O$_3$. (COOH)$_2$].

Synthesis of Cis-(6-benzhydryl-tetrahydropyran-3-yl)-(4-methoxy-benzyl)-amine (16e)

Trans-5-amino-2-diphenylmethyl-tetrahydropyran 15 (0.15 g, 0.56 mmol) was reacted with 4-methoxybenzaldehyde (0.078 g, 0.56 mmol) in the presence of glacial acetic acid (0.033 g, 0.56 mmol) in 1,2-dichloroethane (20 ml), and NaCNBH$_3$ (0.042 g, 0.67 mmol) in methanol (5 ml) (Procedure D) to give compound 16e (0.17 g, 78%) as an oil.

$^1$H NMR (300 MHz, CDCl$_3$) 1.35 (m, 1H, H-5) 1.48-1.76 (m, 2H, H-5, H-4) 1.88-2.02 (m, 1H, H-4) 2.68 (bs, 1H, H-3) 3.59 (dd, J=12.3 Hz, 2.4 Hz, 1H, H-2ax) 3.76 (d, J=7.2 Hz, 2H, (CH$_3$O)Ph-CH$_2$) 3.825 (s, 3H, CH$_3$O-3.98-4.16 (m, 3H, H-6, H-2 eq, Ph$_2$CH) 6.88-6.94, 7.18-7.44 (m, 14H, aromatic-CH). Free base 16e was converted into the oxalate: mp 215-217° C. C,H,N Anal: [C$_{26}$H$_{29}$NO$_2$.(COOH)].

Synthesis of Cis-(6-benzhydryl-tetrahydropyran-3-yl)-(3-indole-methyl)-amine (16f)

Trans-5-amino-2-diphenylmethyl-tetrahydropyran 15 (0.12 g, 0.45 mmol) was reacted with 3-indole-carboxaldehyde (0.065 g, 0.45 mmol) in the presence of glacial acetic acid (0.027 g, 0.45 mmol) in 1,2-dichloroethane (20 ml), and NaCNBH$_3$ (0.034 g, 0.54 mmol) in methanol (5 ml) (Procedure D) to give compound 16f (0.15 g, 82%) as an oil.

$^1$H NMR (400 MHz, CDCl$_3$) 1.34 (m, 1H, H-5) 1.53 (m, 1H, H-5)1.67 (tt, J=14 Hz, 4 Hz, 1H, H-4) 1.93 (m, 1H, H-4) 2.37 (bm, 1H, NH) 2.65 (bs, 1H, H-3) 3.57 (dd, J=10.77 Hz, 1.6 Hz, 1H, H-2ax) 3.96 (s, 2H, 2-Indole-CH$_2$)3.92-4.14 (m, 3H, H-6, H-2 eq, Ph$_2$CH) 6.35 (s, 1H, Indole-3-H) 7.05-7.6 (m, 14H, aromatic-CH) 9.1 (s, 1H, Indole-NH). Free base 16f was converted into the oxalate: mp 177-179° C. C, H, N Anal: [C$_{27}$H$_{28}$N$_2$O—(COOH)$_2$.0.5H$_2$O].

Synthesis of Cis-(6-benzhydryl-tetrahydropyran-3-yl)-(2-indole-methyl)-amine (16g)

Trans-5-amino-2-diphenylmethyl-tetrahydropyran 15 (0.067 g, 0.25 mmol) was reacted with 2-indole-carboxaldehyde (0.036 g, 0.25 mmol) in the presence of glacial acetic acid (0.015 g, 0.25 mmol) in 1,2-dichloroethane (20 ml), and then reduced by NaCNBH$_3$ (0.019 g, 0.3 mmol) in methanol (5 ml) (Procedure. D) to give compound 16g (0.081 g, 82%) as an oil.

$^1$H NMR (300 MHz, CDCl$_3$) 1.33 (m, 1H, H-5) 1.48-1.76 (m, 2H, H-5, H-4) 1.99 (m, 1H, H-4) 2.27 (bs, 1H, NH) 2.79 (m, 1H, H-3) 3.6 (dd, J=1.8 Hz, 12.3 Hz, 1H, H-2ax) 3.998 (s, 2H, Indole-3-CH$_2$) 4.02-4.2 (m, 3H, H-6, H-2 eq, Ph$_2$CH) 7.0-7.8 (m, 14H, aromatic-CH) 8.42 (s, 1H, Indole-NH). Free base 16g was converted into the oxalate: mp 215-216° C. C, H, N Anal: [C$_{27}$H$_{28}$N$_2$O.(COOH)$_2$. 0.5H$_2$O].

Synthesis of Cis-(6-benzhydryl-tetrahydropyran-3-yl)-(4-hydroxy-benzyl)-amine (16h)

Trans-5-amino-2-diphenylmethyl-tetrahydropyran 15 (0.15 g, 0.56 mmol) was reacted with 4-hydroxybenzaldehyde (0.067 g, 0.56 mmol) in the presence of glacial acetic acid (0.034 g, 0.56 mmol) in 1,2-dichloroethane (20 ml), and NaCNBH$_3$ (0.042 g, 0.67 mmol) in methanol (5 ml) (Procedure D) to give compound 16h (0.17 g, 80%) as an oil.

$^1$H NMR (400 MHz, CDCl$_3$) 1.34 (m, 1H, H-5) 1.50 (m, 1H, H-5)1.67 (tt, J=4 Hz, 13.6 Hz, 1H, H-4) 2.02 (m, 1H, H-4) 2.71 (m, 1H, H-3) 3.56 (dd, J=1.6 Hz, 11.6 Hz, 1H, H-2ax) 3.64 (m, 2H, (HO)Ph-CH$_2$) 3.95 (d, J=8.0 Hz, 1H, Ph$_2$CH) 4.02-4.14 (m, 2H, H-6, H-2 eq) 6.52 (m, 2H, aromatic-CH) 6.9-7.38 (m, 12H, aromatic-CH). Free base 16h was converted into oxalate: mp 136-138° C. C, H, N Anal: [C$_{11}$H$_{27}$NO$_2$.(COOH)].

Synthesis of Cis-(6-benzhydryl-tetrahydropyran-3-yl)-(3,4-dichloro-benzyl)-amine (16i)

Trans-5-amino-2-diphenylmethyl-tetrahydropyran 15 (0.1 g, 0.38 mmol) was reacted with 3,4-dichlorobenzaldehyde (0.066 g, 0.38 mmol) in the presence of glacial acetic acid (0.023 g, 0.38 mmol) in 1,2-dichloroethane (20 ml), and NaCNBH$_3$ (0.03 g, 0.45 mmol) in methanol (5 ml) (Procedure D) to give compound 16i (0.12 g, 75%) as an oil.

$^1$H NMR (500 MHz, CDCl$_3$) 1.34 (m, 1H, H-5) 1.52 (m, 1H, H-5)1.66 (m, 1H, H-4) 1.79 (bs, 1H, NH) 1.91 (m, 1H, H-4) 2.61 (m, 1H, H-3)3.57 (dd, J=1.5 Hz, 11.5 Hz, 1H, H-2ax) 3.72 (m, 2H, (Cl, Cl)Ph-CH$_2$) 3.94-4.05 (m, 2H, H-2 eq, Ph$_2$CH) 4.08 (dt, J=2 Hz, 8.5 Hz, 1H, H-6) 7.1-7.5 (m, 14H, aromatic-CH). Free base 16i was converted into the oxalate: mp 251-252° C. C, H, N Anal: [C$_{25}$H$_{25}$NOCl$_2$. (COOH)$_2$].

Synthesis of Cis-(6-benzhydryl-tetrahydropyran-3-yl)-(3,4-difluoro-benzyl)-amine (16j)

Trans-5-amino-2-diphenylmethyl-tetrahydropyran 15 (0.1 g, 0.38 mmol) was reacted with 3,4-difluorobenzaldehyde (0.055 g, 0.38 mmol) in the presence of glacial acetic acid (0.023 g, 0.38 mmol) in 1,2-dichloroethane (20 ml), and NaCNBH$_3$ (0.03 g, 0.45 mmol) in methanol (5 ml) (Procedure D) to give compound 16j (0.12 g, 80%).

$^1$H NMR (300 MHz, CDCl$_3$) 1.34 (m, 1H, H-5) 1.52 (m, 1H, H-5)1.66 (tt, J=3.6 Hz, 13.5 Hz, 1H, H-4) 1.76 (bs, 1H, NH) 1.92 (m, 1H, H-4)2.61 (m, 1H, H-3) 3.57 (dd, J=1.8 Hz, 11.4 Hz, 1H, H-2ax) 3.72 (m, 2H, (F,F)Ph-CH$_2$) 3.94-4.14 (m, 3H, H-6, H-2 eq, Ph$_2$CH) 6.9-7.38 (m, 14H, aromatic-CH). Free base 16j was converted into the oxalate: mp 234-235° C. C, H, N Anal: [C$_{25}$H$_{25}$NOF$_2$.(COOH)].

Synthesis of Cis-(6-benzhydryl-tetrahydropyran-3-yl)-benzyl-amine (16k)

Trans-5-amino-2-diphenylmethyl-tetrahydropyran 15 (0.03 g, 0.11 mmol) was reacted with benzaldehyde (0.012 g, 0.11 mmol) in the presence of glacial acetic acid (0.007 g, 0.11 mmol) in 1,2-dichloroethane (20 ml), and NaCNBH$_3$ (0.009 g, 0.14 mmol) in methanol (5 ml) (Procedure D) to give compound 16k (0.034 g, 85%).

$^1$H NMR (300 MHz, CDCl$_3$) 1.30 (m, 1H, H-5) 1.44-1.70 (m, 2H, H-5, H-4) 1.80 (bs, 1H, NH) 1.92 (m, 1H, H-4) 2.64 (m, 1H, H-3) 3.55 (dd, J=1.8 Hz, 11.7 Hz, 1H, H-2ax) 3.77 (m, 2H, Ph-CH$_2$) 3.92-4.1 (m, 3H, Ph$_2$CH, H-6, H-2 eq) 7.0-7.38 (m, 15H, aromatic-CH). Free base 16k was converted into the oxalate: mp 208-210° C. C, H, N Anal: [C$_{25}$H$_{27}$NO.(COOH)$_2$].

Synthesis of Cis-(6-benzhydryl-tetrahydropyran-3-yl)-(4-bromo-benzyl)-amine (16l)

Trans-5-amino-2-diphenylmethyl-tetrahydropyran 15 (0.04 g, 0.15 mmol) was reacted with 4-bromobenzaldehyde (0.028 g, 0.15 mmol) in the presence of glacial acetic acid (0.009 g, 0.15 mmol) in 1,2-dichloroethane (20 ml), and NaCNBH$_3$ (0.012 g, 0.18 mmol) in methanol (5 ml) (Procedure D) to give compound 16l (0.052 g, 80%) as an oil.

$^1$H NMR (400 MHz, CDCl$_3$) 1.31 (m, 1H, H-5) 1.50 (m, 1H, H-5)1.64 (m, 1H, H-4) 1.80 (bs, 1H, NH) 1.90 (m, 1H, H-4) 2.61 (m, 1H, H-3)3.56 (dd, J=1.6 Hz, 11.6 Hz, 1H, H-2ax) 3.72 (m, 2H, (Br)-Ph-CH$_2$) 3.94-4.30 (m, 2H, Ph$_2$CH, H-2 eq) 4.07 (dt, J=1.6 Hz, J=9.6 Hz, 1H, H-6) 7.0-7.42 (m, 14H, aromatic-CH). Free base 16l was converted into the oxalate: mp 250-252° C. C, H, N Anal: [C$_{25}$H$_{26}$BrNO.(COOH)].

Synthesis of Cis-(6-benzhydryl-tetrahydropyran-3-yl)-(4-iodo-benzyl)-amine (16m)

Trans-5-amino-2-diphenylmethyl-tetrahydropyran 15 (0.04 g, 0.15 mmol) was reacted with 4-iodobenzaldehyde (0.045 g, 0.15 mmol) in the presence of glacial acetic acid (0.009 g, 0.15 mmol) in 1,2-dichloroethane (20 ml), and NaCNBH$_3$ (0.012 g, 0.18 mmol) in methanol (5 ml) (Procedure D) to give compound 16m (0.059 g, 81%) as an oil.

$^1$H NMR (400 MHz, CDCl$_3$) 1.28 (m, 1H, H-5) 1.50 (m, 1H, H-5)1.64 (m, 1H, H-4) 1.72 (bs, 1H, NH) 1.90 (m, 1H, H-4) 2.60 (m, 1H, H-3)3.56 (dd, J=1.6 Hz, 12.4 Hz, 1H, H-2ax) 3.71 (m, 2H, (I)-Ph-CH$_2$) 3.92-4.02 (m, 2H, Ph$_2$CH, H-2 eq) 4.06 (dt, J=1.6 Hz, J=9.2 Hz, 1H, H-6) 7.0-7.70 (m, 14H, aromatic-CH). Free base 16m was converted into the oxalate: mp 243-244° C. C, H, N Anal: [C$_{25}$H$_{26}$INO.(COOH)].

Synthesis of Cis-(6-benzhydryl-tetrahydropyran-3-yl)-(1H-iodo-5-ylmethyl)-amine (16n)

Trans-5-amino-2-diphenylmethyl-tetrahydropyran 15 (0.05 g, 0.19 mmol) was reacted with 5-indole-carboxaldehyde (0.027 g, 0.19 mmol) in the presence of glacial acetic acid (0.011 g, 0.19 mmol) in 1,2-dichloroethane (20 ml), and NaCNBH$_3$ (0.024 g, 0.37 mmol) in methanol (5 ml) (Procedure D) to give compound 16n (0.061 g, 82%) as an oil.

$^1$H NMR (400 MHz, CDCl$_3$) 1.32 (m, 1H, H-5) 1.50-1.70 (m, 2H, H-5, H-4) 1.95 (m, 2H, H-4, NH) 2.71 (m, 1H, H-3) 3.57 (dd, J=2 Hz, 12 Hz, 1H, H-2ax) 3.88 (m, 2H, Indole-CH$_2$) 3.96-4.12 (m, 3H, Ph$_2$CH, H-2 eq, H-6)6.51, 7.1-7.4, 7.57 (m, 15H, aromatic-CH) 8.36 (bs, 1H, NH). Free base 16n was converted into the oxalate: mp 128-130° C. C, H, N Anal: [C$_{27}$H$_{28}$N$_2$O (COOH)$_2$.0.5H$_2$O].

Synthesis of Cis-(6-benzhydryl-tetrahydropyran-3-yl)-(4-amino-benzyl)-amine (16o)

A mixture of cis-(6-benzhydryl-tetrahydropyran-3-yl)-(4-nitro-benzyl)-amine (16f) (0.16 g, 0.39 mmol) and SnCl$_2$/2H$_2$O (0.35 g, 1.55 mmol) in EtOH/EtOAc (20 ml, 7:3) was heated to reflux for 1.5 h (monitored by TLC, Hex/EtOAc/Et$_3$N 5:5:0.4). After removal of the solvent, the residue was diluted with 10% NaHCO$_3$ and EtOAc and stirred vigorously for 30 min. After filtration the organic phase was separated and the aqueous phase was extracted with EtOAc (20 ml×2). The combined organic phase was dried over Na$_2$SO$_4$. After removal of the solvent, flash chromatography gave 16o, cis-(6-benzhydryl-tetrahydropyran-3-yl)-(4-amino-benzyl)-amine (0.087 g, 60%).

$^1$H NMR (400 MHz, CDCl$_3$) 1.3 (m, 1H, H-5) 1.47 (m, 1H, H-5)1.64 (tt, J=4 Hz, 12.8 Hz, 1H, H-4) 1.90 (m, 1H, H-4) 2.53-2.70 (m, 3H, H-3, (NH$_2$)-PhCH$_2$) 3.54 (dd, J=1.6 Hz, 11.2 Hz, 1H, H-2ax) 3.92-4.0 (m, 2H, Ph$_2$CH, H-2 eq) 4.06 (dt, J=2.4 Hz, 9.6 Hz, 1H, H-6) 7.06-7.38 (m, 14H, aromatic-CH). Free base 16o was converted into the oxalate: mp 151-153° C. C, H, N Anal: [C$_{25}$H$_{28}$N$_2$O.2(COOH)$_2$.0.3H$_2$O].

Synthesis of Cis-N-(6-benzhydryl-tetrahydropyran-3-yl)-2-(4-fluoro-phenyl)-acetamide (17)

Into a solution of 4-fluorophenylacetic acid (0.23 g, 1.46 mmol) in dichloromethane (25 ml) was added oxalyl chloride (0.22 g, 1.76 mmol) dissolved in dichloromethane (5 ml) at 0° C. which was followed by addition of one drop of DMF. The reaction mixture was allowed to reach at room temperature over a period of 2 hours. The solvent was removed in vacuo, and the residue was dissolved in dichloromethane (5 ml) and was added into a solution of cis-N-(6-benzhydryl-tetrahydropyran-3-yl)-amine (0.26 g, 0.96 mmol) and triethylamine (0.31 g, 1.46 mmol) in dichloromethane (25 ml) at 0° C. After 20 minutes the reaction mixture was allowed to come to room temperature. After 3 hours, more dichloromethane was added and the mixture was washed in turn with 1N NaHCO$_3$, H$_2$O and brine, then dried over anhydrous Na$_2$SO$_4$. The solvent was removed in vacuo, and the residue was purified by flash chromatography (hexane/ethyl acetate 7:3) to give cis-N-(6-benzhydryl-tetrahydropyran-3-yl)-2-(4-fluorophenyl)-acetamide 17 (0.31 g, yield 80%) as an oil.

$^1$H NMR (300 MHz, CDCl$_3$) 1.1-1.4 (m, 2H, H-5) 1.6-1.93 (m, 2H, H-4) 3.49 (s, 2H, Ph-CH$_2$CO) 3.63 (dd, J=1.8 Hz, 11.7 Hz, 1H, H-2ax) 3.7-3.85 (m, 2H, Ph$_2$CH, H-3) 3.9-4.08 (m, 2H, H-6, H-2 eq) 6.9-7.4 (m, 14H, aromatic-CH).

Synthesis of Cis-(6-benzhydryl-tetrahydropyran-3-yl)-[2-(4-fluoro-phenyl)-ethyl]-amine (16p)

Into a suspension of NaBH$_4$ (0.21 g, 3.33 mmol) in dry THF (20 ml) was added BF$_3$-Et$_2$O drop wise at 0° C. The mixture was stirred for 1.5 Hours at room temperature and cooled to 0° C. A solution of cis-N-(6-benzhydryl-tetrahydropyran-3-yl)-2-(4-fluorophenyl)-acetamide 17 (0.17 g, 0.42 mmol) in dry THF (10 ml) was added dropwise into the solution. The mixture was refluxed overnight and cooled to room temperature. Methanol was added to quench the reaction followed by removal of solvent in vacuo. To the residue was added 20 ml 10% HCl/MeOH and the mixture refluxed for 1 hour. The reaction mixture was cooled down to room temperature and solid NaHCO$_3$ was added at 0° C. to pH 9.

The aqueous phase was extracted with dichloromethane (3×20 ml). The combined organic phases were dried over anhydrous $Na_2SO_4$, and the solvent was removed in vacuo. Flash chromatography gave 16p Cis-(6-benzhydryl-tetrahydropyran-3-yl)-[2-(4-fluorophenyl)-ethyl]-amine (0.13 g, yield 81%).

$^1$H NMR (300 MHz, $CDCl_3$) 1.2-1.42 (m, 2H, H-5, NH) 1.61 (m, 1H, H-5) 1.88 (m, 2H, H-4) 2.64 (m, 1H, H-3) 2.72-2.82 (m, 4H, Ph-$CH_2CH_2$) 3.55 (dd, J=1.8 Hz, 11.7 Hz, 1H, H-2ax) 3.86-3.98 (m, 2H, $Ph_2CH$, H-2 eq)4.03 (dt, J=3 Hz, 10 Hz, 1H, H-6) 6.9-7.4 (m, 14H, aromatic-CH). Free base 16p was converted into the oxalate: mp 240-242° C. C, H, N Anal: [$C_{26}H_{28}NOF$. (COOH)].

Biology. The affinity of test compounds in binding to rat DAT, SERT, and NET was assessed by measuring inhibition of binding of 5.0 nM [$^3$H]WIN 35,428, 3.5 nM [$^3$H]citalopram, and 1.1 nM [$^3$H]nisoxetine, respectively, exactly as described by us previously. Briefly, rat striatum was the source for DAT, and cerebral cortex for SERT and NET. Final [$Na^+$] was 30 mM for DAT and SERT assays, and 152 nM for NET assays. All binding assays were conducted at 0-4?, for a period of 2 h for [$^3$H]WIN 35,428 and [$^{31}$H]citalopram binding, and 3 h for [$^3$H]nisoxetine binding. Nonspecific binding of [$^3$H]WIN 35,428 and [$^3$H]citalopram binding was defined with 100 uM cocaine, and that of [$^3$H]nisoxetine binding with 1 uM desipramine. Radioligand Kd values were 2.1, 3.2 and 2.2 nM, respectively. Test compounds were dissolved in dimethyl sulfoxide (DMSO) and diluted out in 10% (v/v) DMSO. Additions from the latter stocks resulted in a final concentration of DMSO of 0.5%, which by itself did not interfere with radioligand binding. At least five triplicate concentrations of each test compound were studied, spaced evenly around the $IC_{50}$ value. For DAT uptake assays, uptake of 50 nM [$^3$H]DA into rat striatal synaptosomes was measured exactly as described by us previously. Briefly, rat striatal $P_2$ membrane fractions were incubated with test compounds for 8 min followed by the additional presence of [$^3$H]DA for 4 min at 25?. Nonspecific uptake was defined with 100 uM cocaine. Construction of inhibition curves and dissolvement of test compounds were as described above.

TABLE 2

Affinity of Drugs at Dopamine, Serotonin, and Norepinephrine Transporters in Rat Striatum

| Compound | DAT binding, $IC_{50}$, nM, [$^3$H]Win 35, 428[a] | SERT binding, $IC_{50}$, nM [$^3$H]citalopram[a] | NET binding, $IC_{50}$, nM [$^3$H]nisoxetine[a] | DAT uptake, $IC_{50}$, nM [$^3$H]DA[a] |
|---|---|---|---|---|
| Cocaine | 266 ± 37 | 737 ± 160 | 3,130 ± 550 | |
| GBR 12909 | 10.6 ± 1.9 | 132 ± 0 | 496 ± 22 | |
| 1 | 32.5 ± 12.6 | 2,220 ± 590 | 1,020 ± 72 | 45.7 ± 5.1 |
| 7a | 1,302 ± 68 | 3,313 ± 170 | 5,101 ± 1,037 | |
| 7b | 1,581 ± 283 | 4,778 ± 1,808 | 17,543 ± 2,153 | |
| 16a | 313 ± 71[b] | 8,410 ± 163 | 12,700 ± 3,180 | |
| 16b | 163 ± 29[b] | 1,860 ± 22 | 232 ± 46 | 146 ± 36 |
| 16c | 52.6 ± 5.9[b] | 863 ± 52 | 1,580 ± 89 | 58.6 ± 13.2 |
| 16d | 38.3 ± 3.9[b] | 738 ± 164 | 968 ± 98 | 102 ± 7 |
| 16e | 84 ± 6.5 | 1,180 ± 269 | 1,550 ± 682 | 59.5 ± 11.6 |
| 16f | 794 ± 111 | 2,590 ± 1,410 | 1,860 ± 847 | |
| 16g | 227 ± 67 | 1,640 ± 448 | 401 ± 96 | 135.2 ± 47.5 |
| 16h | 78.4 ± 9 | 398 ± 22 | 22.6 ± 1.4 | |
| 16i | 400 ± 31 | 780 ± 84 | 144 ± 25 | 880 ± 136 |
| 16j | 368 ± 85 | 3,520 ± 831 | 695 ± 142 | |
| 16k | 303 ± 14 | 1577 ± 97 | 274 ± 29 | 242 ± 39 |
| 16l | 202 ± 13 | 2363 ± 92 | 592 ± 12 | 251 ± 14 |
| 16m | 319 ± 21 | 2477 ± 145 | 234 ± 17 | 500 ± 34 |
| 16n | 587 ± 66 | 325 ± 20 | 56 ± 6 | |

TABLE 2-continued

Affinity of Drugs at Dopamine, Serotonin, and Norepinephrine Transporters in Rat Striatum

| Compound | DAT binding, $IC_{50}$, nM, [$^3$H]Win 35, 428[a] | SERT binding, $IC_{50}$, nM [$^3$H]citalopram[a] | NET binding, $IC_{50}$, nM [$^3$H]nisoxetine[a] | DAT uptake, $IC_{50}$, nM [$^3$H]DA[a] |
|---|---|---|---|---|
| 16o | 151 ± 13 | 1690 ± 169 | 123 ± 10 | 155 ± 14 |
| 16p | 129 ± 58 | 3,950 ± 660 | 5,210 ± 678 | |
| 15 | 777 ± 41 | | | 251 ± 31 |

[a]For binding, the DAT was labeled with [$^3$H]WIN 35, 428, the SERT with [$^3$H]citalopram and the NET with [$^3$H]nisoxetine. For uptake by DAT, [3H]DA accumulation was measured. Results are average ± SEM of three to eight independent experiments assayed in triplicate.
[b]See reference # 22.

TABLE 3

Selectivity of Various Drugs for their Activity at Monoamine Transporters

| Compound | SERT binding/ DAT binding | NET binding/ DAT binding | [3H]DA uptake/ DAT binding |
|---|---|---|---|
| Cocaine | 2.8 | 11.8 | |
| GER 12909 | 12.5 | 46.8 | |
| 1 | 68.3 | 31.4 | 1.4 |
| 7a | 2.5 | 3.9 | |
| 7b | 3 | 11.1 | |
| 16a | 26.9 | 40.6 | |
| 16b | 11.4 | 1.4 | 0.96 |
| 16c | 16.4 | 30 | 1.1 |
| 16d | 19.3 | 25.3 | 2.7 |
| 16e | 14 | 18.5 | 0.71 |
| 16f | 3.3 | 2.3 | |
| 16g | 7.2 | 1.8 | 0.60 |
| 16h | 5.1 | 0.29 | |
| 16i | 1.9 | 0.36 | |
| 16j | 9.6 | 1.9 | |
| 16k | 5.20 | 0.90 | 0.79 |
| 16l | 11.69 | 2.93 | 1.24 |
| 16m | 7.76 | 0.73 | 1.56 |
| 16n | 0.55 | 0.09 | |
| 16o | 11.19 | 0.81 | 1.02 |
| 16p | 30.6 | 40.4 | |
| 15 | | | 0.32 |

Synthesis of 3,3-Diphenylpropene (22)

Methyltriphenylphosphonium bromide (4 g, 11.12 mmol) was added over a 15-min period to a mixture of butyllithium (7.3 ml of 1.6 M solution in THF, 11.76 mmol) and dry THF (50 ml) with stirring and under nitrogen atmosphere at 0° C. The reaction mixture was stirred for 2 h at room temperature and the mixture was then recooled to −78° C. A solution of diphenylacetaldehyde (2.2 g, 11.12 mmol) in dry THF (10 ml) was added to the above mixture over a 15-min period. The reaction mixture was stirred for 24 h at room temperature, followed by addition of ethyl ether (200 ml), and the reaction mixture was then filtered. The ether extracts were washed with water (3×50 ml), brine (100 ml) and dried over anhydrous sodium sulfate. The crude material was purified by flash chromatography on silical gel (Hexane:Ethyl ether=9:1) to give pure 3,3-diphenylpropene 460 mg (46%).

$^1$HNMR ($CDCl_3$, 400 MHz) 4.82 (d, J=6.4 Hz, 1H, H-3) 5.08 (d, J=17.2 Hz, 1H, H-1) 5.31 (d, J=12 Hz, 1H, H-1) 6.39 (m, 1H, H-2) 7.2-7.4 (m, 10H, aromatic-H) $^{13}$CNMR ($CDCl_3$, 100 MHz) 55.30, 116.69, 126.67, 128.73, 128.92, 140.94, 143.59.

Synthesis of 2-Benzhydryl-oxirane (23)

A flask was charged with 3,3-diphenylpropene (5.1 g, 26.3 mmol) in 100 ml $CH_2Cl_2$. It was followed by portionwise addition of mCPBA (9.1 g, 70% purity, 52.6 mmol) at 0° C. The mixture was stirred at room temperature for 24 h and the reaction was then quenched with 30 ml 1M $Na_2SO_3$. The aqueous layer was extracted with $CH_2Cl_2$ (2×100 ml). The combined organic phases were washed in turn with saturated $NaHCO_3$, brine, and then dried over anhydrous $Na_2SO_4$. Purification by flash chromatography (Hexane/ether=9:1) gave pure 2-benzhydryl-oxirane, 4.7 g (85%).

$^1$HNMR ($CDCl_3$, 400 MHz) 2.54 (m, 1H, H-1) 2.87 (m, 1H, H-1)3.54 (m, 1H, H-2) 3.86 (d, J=7.6 Hz, 1H, $Ph_2CH$), 7.2-7.4 (m, 10H, aromatic-H) $^{13}$CNMR ($CDCl_3$, 100 MHz) 46.80, 53.58, 55.17, 127.06, 127.14, 128.70, 128.81, 141.28.

Resolution of Racemic 2-benzhydryl-oxirane (23) by HKR Reaction

A mixture of (R,R)-(–)-N,N'-Bis(3,5-di-tert-butylsalicylidene)-1,2-cyclohexane diaminocobalt (II) (0.22 g, 0.37 mmol, 0.8%), toluene (5 ml), and acetic acid (0.044 g, 0.74 mmol) was stirred for 1 h at room temperature. The solvent was removed in vacuo and the residue was dried. 2-Benzhydryl-oxirane (9.6 g, 45.7 mmol) was added in one portion and stirred, the mixture was then cooled by means of an ice-bath. $H_2O$ (0.58 g, 32 mmol) was slowly added over a 30-min period. After water addition, the ice bath was removed and the reaction mixture was stirred at room temperature for 72 h. Compounds were separated via flash chromatography on silica gel column to give (2R)-2-benzhydryl-oxirane (23a) 4.5 g ($[\alpha]_D$=(+)9.58, c=1, MeOH) and (2S)-3,3-diphenyl-propane-1,2-diol 24 3.53 g ($[\alpha]_D$=(+)48, c=1, MeOH, ee=97%). The proton and carbon NMR data of (2R)-2-benzhydryl-oxirane was identical to the racemate 2-benzhydryl-oxirane.

$^1$HNMR ($CDCl_3$, 400 MHz) 2.54 (m, 1H, H-1) 2.87 (m, 1H, H-1)3.54 (m, 1H, H-2) 3.86 (d, J=7.6 Hz, 1H, $Ph_2CH$), 7.2-7.4 (m, 10H, aromatic-H). $^{13}$CNMR ($CDCl_3$, 100 MHz) 46.80, 53.58, 55.17, 127.06, 127.14, 128.70, 128.81, 141.28.

For (2S)-3,3-diphenyl-propane-1,2-diol:

$^1$HNMR ($CDCl_3$, 400 MHz) 2.39 (bs, 2H, OH) 3.44 (m, 1H, H-1)3.60 (m, 1H, H-1), 4.02 (D, J=10 Hz, 1H, $Ph_2CH$), 4.44 (m, 1H, H-2), 7.16-7.22 (m, 10H, aromatic-H). $^{13}$CNMR ($CDCl_3$, 100 MHz) 55.08, 64.94, 74.26, 127.08, 127.23, 128.35, 128.84, 129.03, 129.17, 141.23, 141.62

Synthesis of (2S)-2-benzhydryl-oxirane (23b)

A solution of (2S)-3,3-diphenyl-propane-1,2-diol (3.5 g, 15.35 mmol), $Ph_3P$ (8.05 g, 30.7 mmol), and DEAD (5.4 g, 30.7 mmol) in benzene (50 ml) was refluxed for 24 h. Solvent was removed and the residue was diluted with ethyl ether (200 ml) to precipitate $Ph_2PO$. The filtrate was concentrated and the residue was chromatographed on silica gel (hexane/ether=9:1) to give (2S)-2-benzhydryl-oxirane 23b 2.5 g (78%, $[\alpha]_D$=(–)9.6, c=1, MeOH). The $^1$HNMR and $^{13}$CNMR were identical with (R)-isomer.

$^1$HNMR ($CDCl_3$, 400 MHz) 2.54 (m, 1H, H-1) 2.87 (m, 1H, H-1)3.54 (m, 1H, H-2) 3.86 (d, J=7.6 Hz, 1H, $Ph_2CH$), 7.2-7.4 (m, 10H, aromatic-H). $^{13}$CNMR ($CDCl_3$, 100 MHz) 46.80, 53.58, 55.17, 127.06, 127.14, 128.70, 128.81, 141.28.

Procedure A

Synthesis of (2S)-1,1-Diphenyl-pent-4-ene-2-ol (25a)

(2R)-2-benzhydryl-oxirane (0.5 g, 2.38 mmol) 23a was dissolved in dry THF (5 ml) and was added into a dry THF solution at –78° C. containing CuI (0.045 g, 0.24 mmol) and vinylmagnesium bromide (5.95 ml of 1.0M solution in THF, 5.95 mmol). The reaction mixture was stirred and allowed to reach room temperature over a period of 2 h, and then quenched with saturated $NH_4Cl$ solution. The aqueous phase was extracted with ethyl acetate (3×30 ml). The combined organic phase was washed with brine and dried over anhydrous $Na_2SO_4$. The solvent was removed and the residue was purified by flash chromatography on silica gel (Hexane/Ethyl Ether=4:1) to give 0.4 g (2S)-1,1-diphenyl-pent-4-ene-2-ol (70%, $[\alpha]_D$=(–)25, c=1, MeOH).

$^1$HNMR ($CDCl_3$, 400 MHz) 2.14 (m, 1H, H-3), 2.33 (m, 1H, H-3), 3.93 (d, J=8.8 Hz, 1H, H-1) 4.44 (m, 1H, H-2) 5.1 (m, 2H, H-5), 5.9 (m, 1H, H-4), 7.16-7.24 (m, 10H, aromatic-H). $^{13}$CNMR ($CDCl_3$, 100 MHz) 39.75, 58.21, 73.06, 118.23, 126.86, 127.08, 128.51, 128.64, 128.92, 129.00, 135.01.

Synthesis of (2R)-1,1-diphenyl-pent-4-ene-2-ol (25b)

(2S)-2-benzhydryl-oxirane (0.61 g, 2.91 mmol) was reacted with vinylmagnesium bromide (7.26 ml of 1.0M solution in THF, 7.26 mmol) in the presence of CuI (0.055 g, 0.29 mmol) (Procedure A) to yield (2R)-1,1-diphenyl-pent-4-ene-2-ol 0.48 g (70%, $[\alpha]_D$=(+)26, c=1, MeOH). The $^1$HNMR and $^{13}$CNMR were identical with (2S)-1,1-diphenyl-pent-4-ene-2-ol.

$^1$HNMR ($CDCl_3$, 400 MHz) 2.14 (m, 1H, H-3), 2.33 (m, 1H, H-3), 3.93 (d, J=8.8 Hz, 1H, H-1) 4.44 (m, 1H, H-2) 5.1 (m, 2H, H-5), 5.9 (m, 1H, H-4), 7.16-7.24 (m, 10H, aromatic-H).

$^{13}$CNMR ($CDCl_3$, 100 MHz) 39.75, 58.21, 73.06, 118.23, 126.86, 127.08, 128.51, 128.64, 128.92, 129.00, 135.01.

Procedure B

Synthesis of (2S)-1,1-Diphenyl-2-Allyloxy-Pent-4-en (26a)

(2S)-1,1-diphenyl-pent-4-ene-2-ol 25a (0.37 g, 1.57 mmol) was dissolved in dry DMF (2 ml) and was added to a suspension of NaH (60% in mineral oil, 0.13 g, 3.14 mmol) in dry DMF (20 ml) at 0° C. The reaction mixture was allowed to reach room temperature over a period of 1 h. The reaction mixture was cooled again to 0° C. employing an ice-bath, and neat allyl bromide (0.57 g, 4.71 mmol) was added via syringe. The reaction mixture was removed from the ice-bath and stirred overnight at room temperature. The reaction was cooled again to 0° C. and quenched by slowly adding $H_2O$ (20 ml). The resulting mixture was extracted with $Et_2O$ (3×50 ml), and the combined organic phases were washed in turn with H2O, brine, and then dried over anhydrous $Na_2SO_4$. Filtration followed by concentration gave crude product as light orange oil. Purification by chromatography (hexane/ethyl ether=10:1) gave 0.37 g (2S)-1,1-Diphenyl-2-Allyloxy-Pent-4-en (85%, $[\alpha]_D$=(+)19.7, c=1, MeOH).

$^1$HNMR (CDCl$_3$, 500 MHz) 2.26 (m, 1H, H-3), 2.38 (m, 1H, H-3), 3.74 (m, 1H, H-3'), 3.96 (m, 1H, H-3'), 4.1 (m, 2H, H-1, H-2), 5.0-5.16 (m, 4H, H-5, H-1'), 5.71 (m, 1H, H-2'), 5.93 (m, 1H, H-4), 7.2-7.46 (m, 10H, aromatic-H). $^{13}$CNMR (CDCl$_3$, 125 MHz) 37.27 56.24 71.74 81.80 116.71 117.63 126.4 126.62 128.38 128.70 128.83 129.36 135.21 142.26 142.87.

Synthesis of (2R)-1,1-Diphenyl-2-Allyloxy-Pent-4-en (26b)

(2R)-1,1-diphenyl-pent-4-en-2-ol 25b (0.42 g, 1.75 mmol) was reacted with allyl bromide (0.63 g, 5.25 mmol) (Procedure B) to yield (2R)-1,1-Diphenyl-2-Allyloxy-Pent-4-en 26b, 0.43 g (87%, $[\alpha]_D$=(−)20, c=1, MeOH). The $^1$HNMR and $^{13}$CNMR were identical with (2R)-1,1-diphenyl-2-alluloxy-pent-4-en shown above.

$^1$HNMR (CDCl$_3$, 500 MHz) 2.26 (m, 1H, H-3), 2.38 (m, 1H, H-3), 3.74 (m, 1H, H-3'), 3.96 (m, 1H, H-3'), 4.1 (m, 2H, H-1, H-2), 5.0-5.16 (m, 4H, H-5, H-1'), 5.71 (m, 1H, H-2'), 5.93 (m, 1H, H-4), 7.2-7.46 (m, 10H, aromatic-H). $^{13}$CNMR (CDCl$_3$, 125 MHz) 37.27 56.24 71.74 81.80 116.71 117.63 126.4 126.62 128.38 128.70 128.83 129.36 135.21 142.26 142.87.

Procedure C

Synthesis of (2S)-2-benzhydryl-3,6-dihydro-2H-pyran (27a)

Into a solution of (2S)-1,1-Diphenyl-2-Allyloxy-Pent-4-ene 26a (0.19 g, 0.68 mmol) in dry benzene was added Grubb catalyst (0.028 g, 0.034 mmol, 5%) and the solution was refluxed under N$_2$ for 20 h. The solvent was removed, and the residue was purified by flash chromatography (hexane/ether=9:1) to give 0.15 g (2S)-2-benzhydryl-3,6-dihydro-2H-pyran, 27a (88%, $[\alpha]_D$=(−)79.3, c=1, MeOH).

$^1$HNMR (CDCl$_3$, 400 MHz) 1.82 (m, 1H, H-3) 2.09 (m, 1H, H-3) 4.0 (d, J=8.8 Hz, 1H, Ph$_2$CH) 4.23 (m, 2H, H-6) 4.32 (dt, J=2.4 Hz, 9.6 Hz, H-2) 5.77 (m, 2H, H-4, H-5) 7.16-7.26 (m, 10H, aromatic-H). $^{13}$CNMR (CDCl$_3$, 100 MHz) 31.10 51.82 55.52 56.66 67.86 68.03 74.20 126.63 126.86 127.38 128.35 128.81 128.57 128.65 128.74 128.96 142.18 142.37.

Synthesis of (2R)-2-Benzhydryl-3,6-dihydro-2H-pyran (27b)

(2R)-1,1-Diphenyl-2-Allyloxy-Pent-4-en 26b (0.25 g, 0.90 mmol) was cyclized in the presence of Grubb's catalyst (0.037 g, 0.045 mmol) (Procedure C) to produce (2R)-2-Benzhydryl-3,6-dihydro-2H-pyran 27b 0.2 g (89%, $[\alpha]_D$=(+)80.8, c=1, MeOH). The $^1$HNMR and $^{13}$CNMR were identical with (2S)-2-benzhydryl-3,6-dihydro-2H-pyran 27a.

$^1$HNMR (CDCl$_3$, 400 MHz) 1.82 (m, 1H, H-3) 2.09 (m, 1H, H-3) 4.0 (d, J=8.8 Hz, 1H, Ph$_2$CH) 4.23 (m, 2H, H-6) 4.32 (dt, J=2.4 Hz, 9.6 Hz, H-2) 5.77 (m, 2H, H-4, H-5) 7.16-7.26 (m, 10H, aromatic-H). $^{13}$CNMR (CDCl$_3$, 100 MHz) 31.10 51.82 55.52 56.66 67.86 68.03 74.20 126.63 126.86 127.38 128.35 128.81 128.57 128.65 128.74 128.96 142.18 142.37.

Procedure D

Synthesis of (1S,4S,6R)-4-benzhydryl-3,7-dioxa-bicyclo[4.1.0]-heptane (28a) and (1R,4S,6S)-4-benzhydryl-3,7-dioxa-bicyclo[4.1.0]-heptane (28b)

To a solution of (2S)-2-benzhydryl-3,6-dihydro-2H-pyran 27a (0.15 g, 0.6 mmol) in CH$_2$Cl$_2$ (20 ml) was added mCPBA (0.3 g, 70%, 1.2 mmol) in a portionwise manner at 0° C. The mixture was brought to room temperature and the reaction mixture was stirred for 20 h under N$_2$. Na$_2$SO$_3$ (20 ml 1.0 M solution) was added to the reaction mixture at 0° C. to quench the reaction. The aqueous phase was extracted with CH$_2$Cl$_2$ (20 ml×2). The combined organic phase was washed in turn with saturated NaHCO$_3$ and brine, then dried over anhydrous Na$_2$SO$_4$. Evaporation of the solvent gave light brown solid residue. The crude products were purified by flash chromatography on silica gel (hexane/ethyl ether=9:1) to give 0.08 g (1S,4S,6R)-4-benzhydryl-3,7-dioxa-bicyclo[4.1.0]-heptane 28a (50.3%, $[\alpha]_D$=(−)60, c=1, MeOH) and 0.065 g 28b (1R,4S,6S)-4-benzhydryl-3,7-dioxa-bicyclo[4.1.0]-heptane (41%, $[\alpha]_D$=(−)76, c=1, MeOH).

(1S,4S,6R)-4-benzhydryl-3,7-dioxa-bicyclo[4.1.0]-heptane 28a: $^1$HNMR (CDCl$_3$, 400 MHz) 1.71 (m, 1H, H-5) 1.89 (m, 1H, H-5) 3.27 (m, 1H, H-1) 3.34 (m, 1H, H-7) 3.82 (d, J=9.6 Hz, 1H, Ph$_2$CH) 3.95 (d, J=14 Hz, 1H, H-2) 4.14 (dt, J=2.4 Hz, 10.2 Hz, H-4) 4.22 (dd, J=4 Hz, 12.8 Hz, 1H, H-2) 7.16-7.36 (m, 10H, aromatic-CH). $^{13}$CNMR (CDCl$_3$, 100 MHz) 31.1 51.82 55.52 56.67 67.86 68.03 74.20 126.63 126.86 127.38 128.35 128.51 128.57 128.65 128.74 128.96 142.18 142.37.

(1R,4S,6S)-4-benzhydryl-3,7-dioxa-bicyclo[4.1.0]-heptane 28b: $^1$HNMR (CDCl$_3$, 400 MHz) 1.66-1.86 (m, 2H, H-5) 3.06 (m, 1H, H-1) 3.28 (m, 1H, H-7) 3.78-3.98 (m, 3H, Ph$_2$CH, H-2, H-4) 4.19 (d, J=13.6 Hz, 1H, H-2) 7.16-7.36 (m, 10H, aromatic-CH). $^{13}$CNMR (CDCl$_3$, 100 MHz) 31.1 51.82 55.52 56.67 67.86 68.03 74.20 126.63 126.86 127.38 128.35 128.51 128.57 128.65 128.74 128.96 142.18 142.37.

Synthesis of (1R,4R,6S)-4-benzhydryl-3,7-dioxa-bicyclo[4.1.0]-heptane (28c) and (1S,4R,6R)-4-benzhydryl-3,7-dioxa-bicyclo[4.1.0]-heptane (28d)

(2R)-2-benzhydryl-3,6-dihydro-2H-pyran 27b (0.2 g, 0.79 mmol) was reacted with mCPBA (0.27 g, 70%, 1.58 mmol) (Procedure D) to yield the corresponding (1R,4R,6S)-4-benzhydryl-3,7-dioxa-bicyclo[4.1.0]-heptane 28c 0.11 g (52%, $[\alpha]_D$=(+)60.4, c=1, MeOH)) and (1S,4R,6R)-4-benzhydryl-3,7-dioxa-bicyclo[4.1.0]-heptane 28d 0.086 g (41%, $[\alpha]_D$=(+)78, c=1, MeOH). The $^1$HNMR and $^{13}$CNMR were identical for both (1S,4S,6R)-4-benzhydryl-3,7-dioxa-bicyclo[4.1.0]-heptane and (1R,4S,6S)-4-benzhydryl-3,7-dioxa-bicyclo[4.1.0]-heptane.

(1R,4R,6S)-4-benzhydryl-3,7-dioxa-bicyclo[4.1.0]-heptane 28c: $^1$HNMR (CDCl$_3$, 400 MHz) 1.71 (m, 1H, H-5) 1.89 (m, 1H, H-5) 3.27 (m, 1H, H-1) 3.34 (m, 1H, H-7) 3.82 (d, J=9.6 Hz, 1H, Ph$_2$CH) 3.95 (d, J=14 Hz, 1H, H-2) 4.14 (dt, J=2.4 Hz, 10.2 Hz, H-4) 4.22 (dd, J=4 Hz, 12.8 Hz, 1H, H-2) 7.16-7.36 (m, 10H, aromatic-CH). $^{13}$CNMR (CDCl$_3$, 100 MHz) 31.1 51.82 55.52 56.67 67.86 68.03 74.20 126.63 126.86 127.38 128.35 128.51 128.57 128.65 128.74 128.96 142.18 142.37.

(1S,4R,6R)-4-benzhydryl-3,7-dioxa-bicyclo[4.1.0]-heptane 28d: $^1$HNMR (CDCl$_3$, 400 MHz) 1.66-1.86 (m, 2H, H-5) 3.06 (m, 1H, H-1) 3.28 (m, 1H, H-7) 3.78-3.98 (m, 3H, Ph$_2$CH, H-2, H-4) 4.19 (d, J=13.6 Hz, 1H, H-2) 7.16-7.36 (m, 10H, aromatic-CH). $^{13}$CNMR (CDCl$_3$, 100 MHz) 31.151.82 55.52 56.67 67.86 68.03 74.20 126.63 126.86 127.38 128.35 128.51 128.57 128.65 128.74 128.96 142.18 142.37.

Procedure E

Synthesis of (2S,4R,5R)-2-benzhydryl-5-(4-methoxy-benzylamino)-tetrahydropyran-4-ol (−)29a A mixture of (1S,4S,6R)-4-benzhydryl-3,7-dioxa-bicyclo[4.1.0]-heptane 28a (0.027 g, 0.10 mmol) and p-methoxybenzylamine (0.28 g, 2.03 mmol) in ethanol (1 ml) was refluxed under N$_2$ overnight. The solvent was removed and the residue was purified by flash chromatography on silica gel (hexane/ethyl acetate/Et$_3$N=6:4:0.2) to give (2S,4R,5R)-2-benzhydryl-5-(4-methoxy-benzylamino)-tetrahydropyran-4-ol, (−)-29a, 0.03 g (73.2%, [α]$_D$=(−) 71.9, c=1, MeOH).

$^1$HNMR (CDCl$_3$, 400 MHz) 1.42 (m, 1H, H-3) 1.72 (m, 3H, H-3, NH, OH) 2.44 (m, 1H, H-5) 3.66 (d, J=12.8 Hz, H-6) 3.74-3.84 (m, 5H, —OCH3, Ph-CH2) 3.87-3.98 (m, 3H, H-4, H-6, Ph$_2$CH) 4.50 (dt, J=2.4 Hz, 9.6 Hz, 1H, H-2) 6.80-7.40 (m, 14H, aromatic-CH). $^{13}$CNMR (CDCl$_3$, 100 MHz) 33.69 51.04 55.51 56.71 56.79 65.08 67.82 73.81 114.03 126.55 126.75 128.61 128.87 129.47 142.18 142.37.

Free base was converted into oxalate: mp 230-232° C. C, H, N Anal: [C$_{26}$H$_{29}$NO$_3$.(COOH)$_2$].

Synthesis of (2R,4S,5S)-2-benzhydryl-5-(4-methoxy-benzylamino)-tetrahydro-pyran-4-ol(+)29a (1R,4R,6S)-4-benzhydryl-3,7-dioxa-bicyclo[4.1.0]-heptane 28c (0.02 g, 0.075 mmol) was reacted with p-methoxy-benzylamine (0.21 g, 1.50 mmol) in ethanol (Procedure E) to yield (2R,4S,5S)-2-benzhydryl-5-(4-methoxy-benzylamino)-tetrahydropyran-4-ol (+)-29a 0.024 g (80%, [α]$_D$=(+)72.8, c=1, MeOH). The $^1$HNMR and $^{13}$CNMR were identical with (2S,4R,5R)-2-benzhydryl-5-(4-methoxy-benzylamino)-tetrahydropyran-4-ol.

$^1$HNMR (CDCl$_3$, 400 MHz) 1.42 (m, 1H, H-3) 1.72 (m, 3H, H-3, NH, OH) 2.44 (m, 1H, H-5) 3.66 (d, J=12.8 Hz, H-6) 3.74-3.84 (m, 5H, —OCH3, Ph-CH2) 3.87-3.98 (m, 3H, H-4, H-6, Ph$_2$CH) 4.50 (dt, J=2.4 Hz, 9.6 Hz, 1H, H-2) 6.80-7.40 (m, 14H, aromatic-CH). $^{13}$CNMR (CDCl$_3$, 100 MHz) 33.69 51.04 55.51 56.71 56.79 65.08 67.82 73.81 114.03 126.55 126.75 128.61 128.87 129.47 142.18 142.37.

Free base (+)-29a was converted into the oxalate: mp 230-232° C. C, H, N Anal: [C$_{26}$H$_{29}$NO$_3$.(COOH)$_2$. 0.5H$_2$O].

Synthesis of (2R,4S,5S)-2-benzhydryl-5-benzylamino-tetrahydro-pyran-4-ol (+)29d (1R,4R,6S)-4-benzhydryl-3,7-dioxa-bicyclo[4.1.0]-heptane 28c (0.022 g, 0.082 mmol) was reacted with benzylamine (0.18 g, 1.64 mmol) in ethanol (Procedure E) to yield (2R,4S,5S)-2-benzhydryl-5-benzylamino-tetrahydro-pyran-4-ol, (+)-29d 0.025 g (81%, [α]$_D$=(+)53.7, c=1, MeOH).

$^1$HNMR (CDCl$_3$, 400 MHz) 1.43 (m, 1H, H-3) 1.62-1.80 (m, 3H, H-3, NH, OH) 2.54 (m, 1H, H-5) 3.73 (d, J=13.6 Hz, 1H, Ph-CH$_2$) 3.79 (m, 1H, H-6) 3.86-4.02 (m, 4H, H-4, H-6, Ph$_2$CH, Ph-CH$_2$) 4.50 (dt, J=2.4 Hz, 9.6 Hz, 1H, H-2) 7.00-7.40 (m, 15H, aromatic-CH). $^{13}$CNMR (CDCl$_3$, 100 MHz) 33.67 51.64 56.78 56.83 65.10 67.83 73.80 126.57 126.77 127.24 128.30 128.63 128.89 142.25 142.34.

Free base (+)-29d was converted into the oxalate: mp 249-251° C. C, H, N Anal: [C$_{25}$H$_{27}$NO$_2$.(COOH)$_2$.0.3H$_2$O].

Synthesis of (2S,4R,5R)-2-benzhydryl-5-benzylamino-tetrahydro-pyran 4-ol (−)29d (1S,4S,6R)-4-Benzhydryl-3,7-dioxa-bicyclo[4.1.0]-heptane 28a (0.03 g, 0.09 mmol) reacted with benzylamine (0.20 g, 1.88 mmol) in ethanol (Procedure E) to yield (−)-29d, 0.03 g (Yield; 86%), [α]$_D$=(−)54.0, c=1, MeOH).

$^1$HNMR (CDCl$_3$, 400 MHz): 1.43 (m, 1H, H-3 eq), 1.69 (s, 2H, NH, OH), 1.74 (dt, J=2.8 Hz, 10.8 Hz, 1H, H-3ax), 2.45 (m, 1H, H-5), 3.73 (d, J=13.2 Hz, 1H, Ph-CH$_2$), 3.79 (dd, J=2.0 Hz, 12.0 Hz, 1H, H-6), 3.86-4.02 (m, 4H, H-4, H-6, Ph$_2$CH, Ph-CH$_2$), 4.50 (dt, J=2.4 Hz, 10.0 Hz, 1H, H-2), 7.00-7.40 (m, 15H, aromatic-CH).

Free base was converted into oxalate: mp 250-252° C. Anal. [C$_{25}$H$_{27}$NO$_2$.(COOH)$_2$ 0.5H$_2$O] C, H, N.

Synthesis of (3R,4R,6S)-6-benzhydryl-4-(4-methoxy-benzylamino)-tetrahydro-pyran-3-ol(−)29g (1R,4S,6S)-4-benzhydryl-3,7-dioxa-bicyclo[4.1.0]heptane 28b (0.021 g, 0.079 mmol) was reacted with p-methoxy-benzylamine (0.22 g, 1.58 mmol) (Procedure E) to yield (3R,4R,6S)-6-benzhydryl-4-(4-methoxy-benzylamino)-tetrahydropyran-3-ol, (−)-29g 0.02 g (63%, [α]$_D$=(−)63.75, c=1, MeOH).

$^1$HNMR (CDCl$_3$, 400 MHz) 1.37 (m, 1H, H-5) 1.81 (m, 1H, H-5) 2.95 (m, 1H, H-4) 3.46 (m, 1H, H-3) 3.56-3.72 (m, 3H, H-2, PhCH$_2$) 3.81 (s, 3H, —OCH3) 3.96 (d, J=9.6 Hz, 1H, Ph$_2$CH) 4.04 (dd, J=1.6 Hz, 12 Hz, 1H, H-2) 4.53 (dt, J=2.4 Hz, 9.6 Hz, 1H, H-6) 6.8-7.4 (m, 14H, aromatic-CH). $^{13}$CNMR (CDCl$_3$, 100 MHz) 31.14 51.23 55.45 55.53 56.64 67.84 68.05 74.20 126.63 126.86 127.38 128.35 128.51 128.57 128.65 128.74 128.96 142.18 142.37.

Free base (−)-29g was converted into the oxalate: mp 234-235° C. C, H, N Anal: [C$_{26}$H$_{29}$NO$_3$.(COOH)$_2$.0.2H$_2$O].

Synthesis of (3S,4S,6R)-6-benzhydryl-4-(methoxy-benzylamino)-tetrahydro-pyran-3-ol (+)29g (1S,4R,6R)-4-benzhydryl-3,7-dioxa-bicyclo[4.1.0]heptane 28d (0.02 g, 0.075 mmol) was reacted with p-methoxy-benzylamine (0.21 g, 1.50 mmol) (Procedure E) to yield (3S,4S,6R)-6-benzhydryl-4-(4-methoxy-benzylamino)-tetrahydropyran-3-ol, (+)-29g, 0.029 (94%, [α]$_D$=(+)65, c=1, MeOH). The $^1$HNMR and $^{13}$CNMR were identical with (3R,4R,6S)-6-benzhydryl-4-(4-methoxy-benzylamino)-tetrahydropyran-3-ol.

$^1$HNMR (CDCl$_3$, 400 MHz) 1.37 (m, 1H, H-5) 1.81 (m, 1H, H-5) 2.95 (m, 1H, H-4) 3.46 (m, 1H, H-3) 3.56-3.72 (m, 3H, H-2, PhCH$_2$) 3.81 (s, 3H, —OCH3) 3.96 (d, J=9.6 Hz, 1H, Ph$_2$CH) 4.04 (dd, J=1.6 Hz, 12 Hz, 1H, H-2) 4.53 (dt, J=2.4 Hz, 9.6 Hz, 1H, H-6) 6.8-7.4 (m, 14H, aromatic-CH). $^{13}$CNMR (CDCl$_3$, 100 MHz) 31.14 51.23 55.45 55.53 56.64 67.84 68.05 74.20 126.63 126.86 127.38 128.35 128.51 128.57 128.65 128.74 128.96 142.18 142.37.

Free base (+)-29g was converted into the oxalate: mp 235-237° C. C, H, N Anal: [C$_{26}$H$_{29}$NO$_3$.(COOH)$_2$.0.2H$_2$O].

Synthesis of (3S,4S,6R)-benzhydryl-4-benzylamino-tetrahydropyran-3-ol (+)29h (1S,4R,6R)-4-benzhydryl-3,7-dioxa-bicyclo[4.1.0]heptane 28d (0.019 g, 0.071 mmol) was reacted with benzylamine (0.15 g, 1.43 mmol) (Procedure E) to yield (3S,4S,6R)-6-benzhydryl-4-benzylamino-tetrahydropyran-3-ol, (+)-29h, 0.023 (85%, [α]$_D$=(+)70.1, c=1, MeOH).

$^1$HNMR (CDCl$_3$, 400 MHz) 1.38 (m, 1H, H-5) 1.81 (m, 1H, H-5) 2.96 (m, 1H, H-4) 3.48 (m, 1H, H-3) 3.62-3.78 (m, 3H, H-2, PhCH$_2$) 3.96 (d, J=9.6 Hz, 1H, Ph$_2$CH) 4.05 (m, 1H, H-2) 4.54 (dt, J=2.4 Hz, 9.6 Hz, 1H, H-6) 7.0-7.4 (m, 15H, aromatic-CH). $^{13}$CNMR (CDCl$_3$, 100 MHz) 31.10 51.82 55.52 56.66 67.86 68.03 74.20 126.63 126.86 127.38 128.35 128.51 128.57 128.65 128.74 128.96 142.18 142.37.

Free base (+)-29h was converted into the oxalate: mp 259-260° C. C, H, N Anal: [C$_{25}$H$_{27}$NO$_2$.(COOH)$_2$.0.25H$_2$O].

Synthesis of (2S,4R,5R)-2-benzhydryl-5-(4-fluoro-benzylamino)-tetrahydro-pyran-4-ol (−)29b (1S,4S,6R)-4-benzhydryl-3,7-dioxa-bicyclo[4.1.0]-heptane 28a (0.025 g, 0.094 mmol) was reacted with para-fluorobenzylamine (0.24 g, 1.88 mmol) in ethanol (Procedure E) to yield (2S,4R,5R)-2-benzhydryl-5-(4-fluoro-benzylamino)-tetrahydropyran-4-ol, (−)-29b, 0.032 g (86%, [α]$_D$=(−)77.2, c=1, MeOH).

$^1$HNMR (CDCl$_3$, 400 MHz) 1.40 (m, 1H, H-3) 1.71 (m, 1H, H-3)1.78 (bs, 2H, NH, OH) 2.41 (m, 1H, H-5) 3.66 (d, J=13.2 Hz, 1H, H-6) 3.72-3.96 (m, 5H, H-4, H-6, Ph$_2$CH, PhCH$_2$) 4.49 (dt, J=2.4 Hz, 10.4 Hz, 1H, H-2)6.8-7.4 (m, 14H, aromatic-CH). $^{13}$CNMR (CDCl$_3$, 100 MHz) 33.69 50.85 56.70 56.85 65.05 67.70 73.80 115.2 115.50 126.57 126.77 128.61 128.64 128.86 129.74 129.83 142.1 142.31.

Free base (−)-29b was converted into the oxalate: mp 222-223° C. C, H, N Anal: [C$_{25}$H$_{26}$NFO$_2$.(COOH)$_2$].

Synthesis of (2R,4S,5S)-2-benzhydryl-5-(4-fluoro-benzylamino)-tetrahydro-pyran-4-ol (+)29b (1R,4R,6S)-4-benzhydryl-3,7-dioxa-bicyclo[4.1.0]-heptane, 28c, (0.02 g, 0.075 mmol) was reacted with para-fluorobenzylamine (0.19 g, 1.50 mmol) in ethanol (Procedure E) to yield (2R,4S,5S)-2-benzhydryl-5-(4-fluoro-benzylamino)-tetrahydropyran-4-ol, (+)-29b, 0.028 g (94%, [α]$_D$=(+)77.6, c=1, MeOH).

$^1$HNMR (CDCl$_3$, 400 MHz) 1.43 (m, 1H, H-3) 1.68-1.78 (m, 3H, H-3, NH, OH) 2.43 (m, 1H, H-5) 3.68 (d, J=13.2 Hz, 1H, H-6) 3.74-4.00 (m, 5H, H-4, H-6, Ph$_2$CH, PhCH$_2$) 4.50 (dt, J=2.4 Hz, 10.4 Hz, 1H, H-2) 6.8-7.4 (m, 14H, aromatic-CH). $^{13}$CNMR (CDCl$_3$, 100 MHz) 33.71 50.87 56.72 56.85 65.06 67.75 73.81 115.30 115.51 126.57 126.78 128.65 128.87 129.75 129.83 142.20 142.31.

Free base (+)-29b was converted into the oxalate: mp 223-225° C. C, H, N Anal: [C$_{25}$H$_{26}$NFO$_2$.(COOH)$_2$.0.2H$_2$O].

Synthesis of (2S,4R,5R)-2-benzhydryl-5-[2-(4-fluoro-phenyl)-ethylamino]-tetrahydropyran-4-ol (−)29c (1S,4S,6R)-4-benzhydryl-3,7-dioxa-bicyclo[4.1.0]-heptane 28a (0.025 g, 0.094 mmol) was reacted with 2-(4-fluorophenyl)-ethylamine (0.26 g, 1.88 mmol) in ethanol (Procedure E) to yield (2S,4R,5R)-2-benzhydryl-5-[2-(4-fluorophenyl)-ethylamino]-tetrahydropyran-4-ol, (−)-29c, 0.04 g (98%, [α]$_D$=(−)62.9, c=1, MeOH).

$^1$HNMR (CDCl$_3$, 400 MHz) 1.40 (m, 1H, H-3) 1.63 (m, 1H, H-3)1.84 (s, 2H, NH, OH) 2.43 (m, 1H, H-5) 2.73, 2.92 (m, 4H, (F)PhCH$_2$CH$_2$)3.70 (dd, J=2 Hz, 11.6 Hz, 1H, H-6) 3.86-3.98 (m, 3H, H-4, H-6, Ph$_2$CH)4.49 (dt, J=2.4 Hz, 10 Hz, 1H, H-2) 6.8-7.4 (m, 14H, aromatic-CH). $^{13}$CNMR (CDCl$_3$, 100 MHz) 33.70 36.19 49.28 56.74 57.66 65.21 67.35 73.81 115.34 115.55 126.58 126.7 128.61 128.88 130.20 130.30 142.18 142.30.

Free base (−)-29c was converted into the oxalate: mp 205-207° C. C, H, N Anal: [C$_{26}$H$_{28}$NFO$_2$.(COOH)$_2$.0.1H$_2$O].

Synthesis of (2R,4S,5S)-2-benzhydryl-5-[2-(4-fluoro-phenyl)-ethylamino]-tetrahydropyran-4-ol (+)29c (1R,4R,6S)-4-benzhydryl-3,7-dioxa-bicyclo[4.1.0]-heptane 28c (0.02 g, 0.075 mmol) was reacted with 2-(4-fluorophenyl)-ethylamine (0.21 g, 1.50 mmol) in ethanol (Procedure E) to yield (2R,4S,5S)-2-benzhydryl-5-[2-(4-fluorophenyl)-ethylamino]-tetrahydropyran-4-ol, (+)-29c, 0.030 g (98%, [α]$_D$=(+)63.4, c=1, MeOH).

$^1$HNMR (CDCl$_3$, 400 MHz) 1.40 (m, 1H, H-3) 1.63 (m, 1H, H-3)1.84 (s, 2H, NH, OH) 2.43 (m, 1H, H-5) 2.73, 2.92 (m, 4H, (F)PhCH$_2$CH$_2$)3.70 (dd, J=2 Hz, 11.6 Hz, 1H, H-6) 3.86-3.98 (m, 3H, H-4, H-6, Ph$_2$CH)4.49 (dt, J=2.4 Hz, 10 Hz, 1H, H-2) 6.8-7.4 (m, 14H, aromatic-CH). $^{13}$CNMR (CDCl$_3$, 100 MHz) 33.72 36.26 49.33 56.74 57.67 65.28 67.47 73.80 115.33 115.53 126.57 126.78 128.61 128.88 130.22 130.30 142.1 142.30.

Free base (+)-29c was converted into the oxalate: mp 203-205° C. C, H, N Anal: [C$_{26}$H$_{28}$NFO$_2$.(COOH)$_2$.0.5H$_2$O].

Synthesis of (3S,4R,6S)-6-benzhydryl-4-benzylamino-tetrahydropyran-3-ol (−)29h (1R,4S,6S)-4-benzhydryl-3,7-dioxa-bicyclo[4.1.0]-heptane 28b (0.03 g, 0.09 mmol) reacted with benzylamine (0.20 g, 1.88 mmol) (Procedure E) to yield (3S,4R,6S)-6-benzhydryl-4-benzylamino-tetrahydropyran-3-ol, (−)-29h, 0.03 g (Yield; 86%), [α]$_D$=(−)70.6, c=1, MeOH).

$^1$HNMR (CDCl$_3$, 400 MHz): 1.30 (td, J=3.2 Hz, 14 Hz, 1H, H-5 eq), 1.68-1.80 (m, 3H, H-5ax, NH, OH), 2.88 (m, 1H, H-4), 3.40 (m, 1H, H-3), 3.54-3.70 (m, 3H, H-2, PhCH$_2$), 3.88 (d, J=9.60 Hz, 1H, Ph$_2$CH), 3.96 (dd, J=1.60 Hz, 12.00 Hz, 1H, H-2), 4.46 (dt, J=2.40 Hz, 10.00 Hz, 1H, H-6) 7.00-7.40 (m, 15H, aromatic-CH).

Free base (−)-29h was converted into the oxalate: mp 259-260° C. C, H, N Anal: [C$_{15}$H$_{27}$NO$_2$.(COOH)$_2$.0.25H$_2$O].

Synthesis of (2S,4R,5R)-2-benzhydryl-5-(3,5-dimethoxy-benzylamino)-tetrahydropyran-4-ol (−)-29f (1S,4S,6R)-4-benzhydryl-3,7-dioxa-bicyclo[4.1.0]-heptane 28a (0.020 g, 0.075 mmol) was reacted with 3,5-dimethoxybenzylamine (0.25 g, 1.50 mmol) (Procedure E) to yield (2S,4R,5R)-2-benzhydryl-5-(3,5-dimethoxy-benzylamino)-tetrahydropyran-4-ol, (−)-29f, 0.03 g (Yield; 95%, [α]$_D$=(−)58.60, c=1, CHCl$_3$).

$^1$HNMR (CDCl$_3$, 400 MHz): 1.40 (m, 1H, H-3), 1.72 (m, 1H, H-3), 2.42 (m, 1H, H-5), 3.62-4.00 (m, 12H, H-4, H-6, PhCH$_2$, —OCH$_3$, Ph$_2$CH), 4.49 (dt, J=2.00 Hz, 10.00 Hz, 1H, H-2), 6.34, 6.48, 7.10-7.40 (m, 13H, aromatic-CH).

Free base (−)-29f was converted into oxalate: mp 245-247° C. C, H, N Anal: [C$_{27}$H$_{31}$NO$_4$ (COOH)2 0.2H$_2$O].

Synthesis of (2S,4R,5R)-2-benzhydryl-5-(2,4-dimethoxy-benzylamino)-tetrahydropyran-4-ol (−)-29e (1S,4S,6R)-4-benzhydryl-3,7-dioxa-bicyclo[4.1.0]heptane 28a (0.020 g, 0.075 mmol) was reacted with 2,4-dimethoxybenzylamine (0.25 g, 1.50 mmol) (Procedure E) to yield (2S,4R,5R)-2-benzhydryl-5-(2,4-dimethoxybenzylamino)-tetrahydropyran-4-ol, (−)-29e, 0.025 g (Yield; 70%, [α]$_D$=(−)3.70, c=1, CHCl$_3$).

$^1$HNMR (CDCl$_3$, 400 MHz): 1.42 (m, 1H, H-3), 1.77 (m, 1H, H-3), 2.10 (bs, 2H, OH, NH), 2.47 (m, 1H, H-5), 3.66-4.06 (m, 12H, H-4, H-6, PhCH$_2$, —OCH$_3$, Ph$_2$CH), 4.50 (dt, J=2.80 Hz, 9.60 Hz, 1H, H-2), 6.40, 7.10-7.40 (m, 13H, aromatic-CH).

Free base (−)-29e was converted into the oxalate: mp 208-210° C. C, H, N Anal: [C$_{27}$H$_{31}$NO$_4$ (COOH)$_2$].

Procedure F

Synthesis of (2S,4R,5R)-5-Azido-2-benzhydryl-tetrahydro-pyran-4-ol (30a)

A solution of (1S,4S,6R)-4-benzhydryl-3,7-dioxa-bicyclo[4.1.0]-heptane 28a (0.05 g, 0.19 mmol) in a 8:1 MeOH/H$_2$O (2 ml) mixture was treated with NaN₃ (0.061 g, 0.94 mmol) and NH₄Cl (0.022 g, 0.41 mmol) and the resulting reaction mixture was stirred at 80° C. overnight. The reaction mixture was diluted with ether and the organic layer was separated. Evaporation of the washed (saturated aqueous NaHCO₃, water) ether extracts afforded a crude solid product. Purification of the product by flash chromatography (Hexane/Ethyl Acetate=4:1) yielded (2S,4R,5R)-5-Azido-2-benzhydryl-tetrahydropyran-4-ol 30a 0.05 g (95%, [α]$_D$=(−)109.3, c=1, MeOH).

¹HNMR (CDCl₃, 400 MHz) 1.44 (m, 1H, H-3) 1.79 (m, 1H, H-3)1.91 (s, 1H, OH) 3.258 (m, 1H, H-5) 3.82-4.04 (m, 4H, H-4, H-6, Ph₂CH)4.49 (dt, J=2.4 Hz, 10 Hz, 1H, H-2) 7.0-7.4 (m, 10H, aromatic-CH). ¹³CNMR (CDCl₃, 100 MHz) 33.56 56.96 59.63 64.81 66.32 73.56 126.64 126.88 128.62 128.64 128.67 128.92 142.04.

Synthesis of (2R,4S,5S)-5-Azido-2-benzhydryl-tetrahydro-pyran-4-ol (30b)

(1R,4R,7S)-4-benzhydryl-3,7-dioxa-bicyclo[4.1.0]-heptane 8c (0.04 g, 0.15 mmol) was treated with NaN₃ (0.05 g, 0.75 mmol) and NH₄Cl (0.018 g, 0.33 mmol) (Procedure F) yielded (2R,4S,5S)-5-Azido-2-benzhydryl-tetrahydro-pyran-4-ol 30b, 0.04 g (95%, [α]$_D$=(+)108, c=1, MeOH).

¹HNMR (CDCl₃, 400 MHz) 1.45 (m, 1H, H-3) 1.80 (m, 1H, H-3)1.91 (s, 1H, OH) 3.27 (m, 1H, H-5) 3.84-4.05 (m, 4H, H-4, H-6, Ph₂CH)4.50 (dt, J=2.4 Hz, 10 Hz, 1H, H-2) 7.0-7.4 (m, 10H, aromatic-CH). ¹³CNMR (CDCl₃, 100 MHz) 33.59 56.96 59.64 64.81 66.35 73.56 126.64 126.87 128.62 128.64 128.67 128.92 142.06.

Procedure G

Synthesis of (2S,4R,5R)-5-Amino-2-benzhydryl-tetrahydro-pyran-4-ol (31a)

(2S,4R,5R)-5-Azido-2-benzhydryl-tetrahydro-pyran-4-ol (0.05 g, 0.18 mmol) dissolved in methanol (20 ml) was hydrogenated in the presence of 10% Pd/C (0.006 g). The mixture was filtered through a short bed of cellite, and evaporation of the solvent gave (2S,4R,5R)-5-amino-2-benzhydryl-tetrahydro-pyran-4-ol 0.05 g (97%, [α]$_D$=(−)66, c=1, MeOH), which was pure enough for the next reaction.

¹HNMR (CDCl₃, 400 MHz) 1.40 (m, 1H, H-3) 1.70 (m, 1H, H-3)2.73 (s, 1H, H-5) 3.20 (m, 3H, NH, OH) 3.60 (m, 1H, H-6) 3.8-4.0 (m, 3H, H-4, H-6, Ph₂CH) 4.46 (t, J=10 Hz, 1H, H-2) 7.0-7.4 (m, 10H, aromatic-CH). ¹³CNMR (CDCl₃, 100 MHz) 32.87 51.26 56.68 67.25 67.85 74.15 126.60 126.82 128.61 128.65 128.8 142.15 142.18.

Synthesis of (2R,4S,5S)-5-Amino-2-benzhydryl-tetrahydro-pyran-4-ol (31b)

(2R,4S,5S)-5-Azido-2-benzhydryl-tetrahydropyran-4-ol (0.05 g, 0.14 mmol) was hydrogenated (Procedure G) to yield (2R,4S,5S)-5-amino-2-benzhydryl-tetrahydropyran-4-ol 0.04 g (97%, [α]$_D$=(+)66.2, c=1, MeOH).

¹HNMR (CD3OD, 400 MHz) 1.43 (m, 1H, H-3) 1.72 (m, 1H, H-3) 2.65 (m, 1H, H-5) 3.57 (m, 1H, H-6) 3.82 (m, 1H, H-4) 3.92-4.0 (m, 2H, H-6, Ph₂CH) 4.52 (dt, J=2 Hz, 10.4 Hz, 1H, H-2) 7.0-7.4 (m, 10H, aromatic-CH). ¹³CNMR (CD3OD, 100 MHz) 32.40 50.67 56.92 66.65 67.47 74.04 125.96 126.35 128.01 128.38 128.42 142.44 142.77.

Procedure H

Synthesis of (2S,4R,5R)-2-benzhydryl-5-(4-hydroxy-benzylamino)-tetrahydropyran-4-ol (−)32a To a solution of (2S,4R,5R)-5-amino-2-benzhydryl-tetrahydro-pyran-4-ol 31a (0.02 g, 0.09 mmol), 4-hydroxybenzaldehyde (0.01 g, 0.09 mmol) and glacial acetic acid (0.005 g, 0.09 mmol) in 1,2-dichloroethane (5 ml) was added portionwise NaCNBH₃ (0.007 g, 0.11 mmol) in methanol (1 ml). The reaction was continued for 4 hr. Water was added to quench the reaction and the mixture was stirred for 30 minutes at 0° C. The reaction mixture was stirred with saturated aqueous NaHCO₃ and the product was extracted with methylene chloride (3×10 ml). The combined organic phases were washed with brine, water and dried over anhydrous Na₂SO₄. Solvent was removed under reduced pressure, and the residue was purified by flash chromatography (Hexane/Ethyl Acetate/Triethylamine 3:2:0.2) to give (2S,4R,5R)-2-benzhydryl-5-(4-hydroxy-benzylamino)-tetrahydropyran-4-ol, (−)-32a, 0.03 g (80%, [α]$_D$=(−)72.6, c=1, MeOH).

¹HNMR (CDCl₃, 400 MHz) 1.40 (m, 1H, H-3) 1.66 (m, 1H, H-3)2.45 (s, 1H, H-5) 3.23 (bs, NH, OH) 3.58 (d, J=12.4 Hz, 1H, (OH)PhCH₂) 3.7-3.8 (m, 2H, H-6, (OH)PhCH₂) 3.84-4.0 (m, 3H, H-4, H-6, Ph₂CH) 4.49 (dt, J=2 Hz, 10 Hz, 1H, H-2) 6.57, 7.03, 7.1-7.36 (m, 14H, aromatic-CH). ¹³CNMR (CDCl₃, 100 MHz) 33.56 50.86 56.49 56.60 64.55 67.19 73.95 115.82 126.61 126.7 128.5 128.64 128.68 128.87 129.91 130.87 142.0 142.2 155.61.

Free base (−)-32a was converted into the oxalate: C, H, N Anal: [C₂₅H₂₇NO₃—(COOH)₂.0.4H₂O].

Synthesis of (2S,4R,5R)-2-benzhydryl-5-[(1H-indol-5-ylmethyl)-amino]-tetrahydropyran-4-ol (−)32b (2S,4R,5R)-5-amino-2-benzhydryl-tetrahydropyran-4-ol 31a (0.03 g, 0.11 mmol) was reacted with 1H-indol-5-carbaldehyde (0.02 g, 0.11 mmol), glacial acetic acid (0.01 g, 0.11 mmol), and NaCNBH₃ (0.01 g, 0.21 mmol) (Procedure C) to give (2S,4R,5R)-2-benzhydryl-5-[(1H-indol-5-ylmethyl)-amino]-tetrahydropyran-4-ol, (−)32b, 0.04 g (92%, [α]$_D$=(−)69.90, c=1, Acetone).

¹HNMR (DMSO, 400 MHz): 1.24 (m, 1H, H-3 eq), 1.63 (dt, J=2.80 Hz, 12.00 Hz, 1H, H-3ax), 2.35 (m, 1H, H-5), 3.35 (bs, NH, OH), 3.61 (d, J=10.40 Hz, 1H, H-6), 3.68-3.90 (m, 4H, H-4, H-6, indol-CH₂), 3.97 (d, J=10.00 Hz, 1H, Ph₂CH), 4.45 (dt, J=2.00 Hz, 10.00 Hz, 1H, H-2), 6.40, 7.00-7.60 (m, 15H, aromatic-CH). ¹³CNMR (DMSO, 100 MHz): 33.81, 51.72, 56.67, 56.87, 65.03, 65.93, 73.78, 101.52, 111.73, 120.01, 122.45, 126.00, 126.46, 126.88, 128.21, 128.78, 128.95, 128.99, 129.13, 135.69, 143.35, 143.93.

Free base (−)-32b was converted into the oxalate: C, H, N Anal: [C₂₇H₂₈N₂O₂.(COOH)₂.0.5H₂O]

Synthesis of (2R,4S,5S)-2-benzhydryl-5-(4-hydroxybenzylamino)-tetrahydro-pyran-4-ol (+)32a (2R,4S,5S)-5-amino-2-benzhydryl-tetrahydropyran-4-ol 31b (0.02 g, 0.07 mmol) was reacted with 4-hydroxybenzaldehyde (0.009 g, 0.071 mmol), glacial acetic acid (0.004 g, 0.071 mmol) and NaCNBH₃ (0.005 g, 0.085 mmol) (Procedure H) to give (2R,4S,5S)-2-benzhydryl-5-(4-hydroxy-benzylamino)-tetrahydropyran-4-ol, (+)-32a, 0.023 g (85%, [α]$_D$=(+)72.4, c=1, MeOH).

¹HNMR (CDCl₃, 400 MHz) 1.42 (m, 1H, H-3) 1.68 (m, 1H, H-3)2.46 (m, 1H, H-5) 3.52 (bs, NH, OH) 3.60 (d, J=13.6 Hz, 1H, (OH)PhCH₂)3.72-3.82 (m, 2H, H-6, (OH)PhCH₂)

3.86-4.0 (m, 3H, H-4, H-6, Ph$_2$CH)4.50 (dt, J=2.4 Hz, 10.4 Hz, 1H, H-2) 6.58, 7.05, 7.1-7.36 (m, 14H, aromatic-CH). $^{13}$CNMR (CDCl$_3$, 100 MHz) 33.62 50.94 56.59 64.64 67.36 73.93 115.78 126.62 126.7 128.5 128.64 128.6 128.88 129.87 142.08 142.23 155.51.

Free base (+)-32a was converted into the oxalate: C, H, N Anal: [C$_{25}$H$_{27}$NO$_3$.(COOH)$_2$.0.4H$_2$O].

Synthesis of (2R,4S,5S)-2-benzhydryl-5-[(1H-indol-5-ylmethyl)-amino]-tetrahydropyran-4-ol (+)32b (2R,4S,5S)-5-amino-2-benzhydryl-tetrahydropyran-4-ol 31b (0.05 g, 0.18 mmol) was reacted with 1H-indol-5-carbaldehyde (0.03 g, 0.18 mmol), glacial acetic acid (0.01 g, 0.18 mmol) and NaCNBH$_3$ (0.02 g, 0.35 mmol) (Procedure C) to give (2R,4S,5S)-2-benzhydryl-5-[(1H-indol-5-ylmethyl)-amino]-tetrahydropyran-4-ol, (+)32b, 0.05 g (69%, [α]$_D$=(+)70.9, c=1, Acetone).

$^1$HNMR (Acetone, 400 MHz): 1.27 (td, J=2.80 Hz, 14.00 Hz, 1H, H-3 eq), 1.61 (dt, J=2.80 Hz, 14.00 Hz, 1H, H-3ax), 2.34 (m, 1H, H-5), 3.58 (d, J=12.00 Hz, 1H, H-6), 3.68-3.90 (m, 5H, H-4, H-6, indol-CH$_2$, Ph$_2$CH), 4.41 (dt, J=2.40 Hz, 10.00 Hz, 1H, H-2), 6.28, 6.94-7.44 (m, 15H, aromatic-CH). $^{13}$CNMR (Acetone, 100 MHz): 33.59, 51.76, 56.74, 57.07, 64.94, 66.47, 73.74, 101.59, 111.20, 119.95, 122.39, 125.07, 126.01, 126.39, 128.20, 128.57, 128.74, 128.89, 143.22, 143.50.

Free base (+)-32b was converted into the oxalate: C, H, N Anal: [C$_{27}$H$_{28}$N$_2$O$_2$.(COOH)$_2$]

Procedure I

Synthesis of (3R,6S)-6-benzhydryl-tetrahydropyran-3-ol (33a)

(1S,4S,6R)-4-benzhydryl-3,7-dioxa-bicyclo[4.1.0]-heptane 28a (0.3 g, 1.13 mmol) in dry pentane (10 ml) was added to a suspension of LiAlH$_4$ (0.21 g, 5.64 mmol) in dry pentane (20 ml). The resulting reaction mixture was stirred under N$_2$ for 20 hr at room temperature, and then quenched with 10% NaOH, diluted with ethyl acetate (30 ml), and the precipitate removed by filtration. The organic phase was washed with brine and dried over anhydrous Na$_2$SO$_4$. Removal of solvent followed by flash chromatography of the crude product produced pure (3R,6S)-6-benzhydryl-tetrahydro-pyran-3-ol, 33a, 0.23 g (75%, [α]$_D$=(−)-61.6, c=1, MeOH).

$^1$HNMR (CDCl$_3$, 400 MHz) 1.40 (m, 2H, H-5) 1.58 (m, 1H, H-4)2.07 (m, 1H, H-4) 3.14 (t, J=10.4 Hz, 1H, H-2) 3.69 (m, 1H, H-3) 3.82-4.04 (m, 3H, H-2, H-6, Ph$_2$CH) 7.1-7.4 (m, 10H, aromatic-CH). $^{13}$CNMR (CDCl$_3$, 100 MHz) 29.47 33.18 57.40 66.55 73.12 78.95 126.51 126.74 128.54 128.60 128.7 142.41 142.77.

Synthesis of (3S,6R)-6-benzhydryl-tetrahydropyran-3-ol (33b)

(1R,4R,6S)-4-benzhydryl-3,7-dioxa-bicyclo[4.1.0]-heptane (0.05 g, 0.19 mmol) was treated with LiAlH$_4$ (0.036 g, 0.94 mmol) (Procedure I) in dry pentane to yield trans-(3S,6R)-6-benzhydryl-tetrahydro-pyran-3-ol 33b 0.035 g (70%, [α]$_D$=(+)61.7, c=1, MeOH).

$^1$HNMR (CDCl$_3$, 400 MHz) 1.40 (m, 2H, H-5), 1.58 (m, 1H, H-4), 2.07 (m, 1H, H-4), 3.14 (t, J=10.4 Hz, 1H, H-2), 3.69 (m, 1H, H-3), 3.82-4.04 (m, 3H, H-2, H-6, Ph$_2$CH), 7.1-7.4 (m, 10H, aromatic-CH). $^{13}$CNMR (CDCl$_3$, 100 MHz) 29.47 33.18 57.40 66.55 73.12 78.95 126.51 126.74 128.54 128.60 128.7 142.41 142.77.

An Alternative Procedure for the Synthesis of (3S,6R)-6-benzhydryl-tetrahydro-pyran-3-ol (33b)

Synthesis of (3R,6R)-6-benzhydryl-tetrahydropyran-3-ol (38)

Treatment of (1S,4R,6R)-4-benzhydryl-3,7-dioxa-bicyclo [4.1.0]heptane 28d (0.06 g, 0.23 mmol) with a suspension of LiAlH$_4$ (0.06 g, 1.58 mmol) in pentane along with 12-crown-4 ether (0.31 g, 1.74 mmol) for 15 h at room temperature afforded (3R,6R)-6-benzhydryl-tetrahydropyran-3-ol 38 0.046 g (77%, [α]$_D$=(+)74.9, c=1, MeOH).

$^1$HNMR (CDCl$_3$, 400 MHz) 1.28 (m, 1H, H-5) 1.58-1.74 (m, 2H, H-4, H-5) 1.88 (m, 1H, H-5) 2.20 (bs, 1H, OH) 3.63 (m, 1H, H-2) 3.75 (bs, 1H, H-3) 3.88-4.10 (m, 3H, H-2, H-6, Ph$_2$CH) 7.1-7.4 (m, 10H, aromatic-CH). $^{13}$CNMR (CDCl$_3$, 100 MHz) 24.95 30.15 57.78 64.77 73.02 79.64 126.56 126.77 128.58 128.6 128.71 128.81 142.30 142.42.

Procedure J

Synthesis of methanesulfonic acid cis-(3R,6R)6-benzhydryl-tetra-hydropyran-3-yl ester (39)

Methanesulfonyl chloride (0.067 g, 0.58 mmol) was reacted with cis-(3R,6R)-6-diphenylmethyl-tetrahydropyran-3-ol 38 (0.078 g, 0.29 mmol) in the presence of triethylamine (0.044 g, 0.44 mmol) in dry methylene chloride (10 ml) to give cis-(3R,6R)-6-diphenylmethyl tetrahydropyran-3-yl methanesulfonate 39 0.1 g (quantitative yield, [α]$_D$=(+)65.7, c=1, MeOH).

$^1$HNMR (CDCl$_3$, 400 MHz) 1.46 (m, 1H, H-5) 1.62-1.78 (m, 2H, H-4, H-5) 2.24 (m, 1H, H-5) 2.96 (s, 3H, CH$_3$SO$_2$) 3.36 (t, J=10.4 Hz, 1H, H-2)3.88 (d, J=8.8 Hz, 1H, Ph$_2$CH) 4.0 (dt, J=2 Hz, 8.8 Hz, 1H, H-2) 4.14 (m, 1H, H-2) 4.61 (m, 1H, H-3) 7.1-7.4 (m, 10H, aromatic-CH). $^{13}$CNMR (CDCl$_3$, 100 MHz) 29.49 30.58 38.71 57.10 69.87 75.23 79.07 126.6 126.93 128.57 128.60 128.67 128.8 141.94 142.33.

Synthesis of (3S,6R)-6-benzhydryl-tetrahydropyran-3-ol (13b)

cis-(3R,6R)-6-diphenylmethyl tetrahydropyran-3-yl methanesulfonate 39 (0.1 g, 0.29 mmol) and 18-crown-6 (0.76 g, 2.9 mmol) are dissolved in a 1:1 mixture of DMSO and DMF (15 ml). KO$_2$ (0.062 g, 0.87 mmol) was added and the solution was stirred under N$_2$. After 5 hr, the reaction was over. H2O (1 ml) and a few drops of 1M solution of HCl were added and the solution was extracted with Et$_2$O (3×10 ml). The ether phase was washed with water and saturated brine, dried over anhydrous Na$_2$SO$_4$ and evaporated to dryness. The crude product was chromatographed on silica gel using hexane/ethyl acetate 1:1 to yield pure trans-(3S,6R)-6-benzhydryl-tetrahydropyran-3-ol 33b 0.062 g (80%, [α]$_D$=(+)62.8, c=1, MeOH).

$^1$HNMR (CDCl$_3$, 400 MHz) 1.40 (m, 2H, H-5) 1.58 (m, 1H, H-4)2.07 (m, 1H, H-4) 3.14 (t, J=10.4 Hz, 1H, H-2) 3.69 (m, 1H, H-3) 3.82-4.04 (m, 3H, H-2, H-6, Ph$_2$CH) 7.1-7.4 (m, 10H, aromatic-CH). $^{13}$CNMR (CDCl$_3$, 100 MHz) 29.47 33.18 57.40 66.55 73.12 78.95 126.51 126.74 128.54 128.60 128.7 142.41 142.77.

Synthesis of methanesulfonic acid trans-(3R,6S)-6-benzhydryl-tetra-hydropyran-3-yl ester (34a)

Methanesulfonyl chloride (0.20 g, 1.7 mmol) was reacted with trans-(3R,6S)-6-diphenylmethyl-tetrahydropyran-3-ol 33a (0.23 g, 0.85 mmol) (Procedure J) to give trans-(3R,6S)-6-diphenylmethyl tetrahydropyran-3-yl methanesulfonate 34a 0.23 g (80%, $[\alpha]_D$=(−)54, c=1, MeOH).

$^1$H NMR (400 MHz, CDCl$_3$) 1.47 (m, 1H, H-5) 1.62-1.80 (m, 2H, H-5, H-4) 2.25 (m, 1H, H-4) 2.98 (s, 3H, CH$_3$SO$_2$) 3.37 (t, J=10.4 Hz, 1H, H-2ax) 3.89 (d, J=8.8 Hz, 1H, Ph$_2$CH) 4.01 (dt, J=2 Hz, 9.6 Hz, 1H, H-6) 4.15 (m, 1H, H-2 eq) 4.62 (m, 1H, H-3) 7.16-7.38 (m, 10H, aromatic-CH). $^{13}$C NMR (100 MHz, CDCl$_3$) δ(ppm) 29.46, 30.57, 38.71, 57.07, 69.85, 75.19, 79.04, 126.67, 126.90, 128.54, 128.57, 128.63, 128.86, 141.87, 142.28.

Synthesis of methanesulfonic acid trans-(3S,6R)-6-benzhydryl-tetra-hydropyran-3-yl ester 34b Trans-(3S,6R)-6-benzhydryl-tetrahydropyran-3-ol (0.025 g, 0.093 mmol) was reacted with methanesulfonyl chloride (0.021 g, 0.19 mmol) (Procedure J) to yield trans-(3S,6R)-6-benzhydryl-tetrahydropyran-3-yl ester 34b 0.028 g (88%, $[\alpha]_D$=(+)54.8, c=1, MeOH).

$^1$H NMR (400 MHz, CDCl$_3$) 1.47 (m, 1H, H-5) 1.62-1.80 (m, 2H, H-5, H-4) 2.25 (m, 1H, H-4) 2.98 (s, 3H, CH$_3$SO$_2$) 3.37 (t, J=10.4 Hz, 1H, H-2ax) 3.89 (d, J=8.8 Hz, 1H, Ph$_2$CH) 4.01 (dt, J=2 Hz, 9.6 Hz, 1H, H-6) 4.15 (m, 1H, H-2 eq) 4.62 (m, 1H, H-3) 7.16-7.38 (m, 10H, aromatic-CH). $^{13}$C NMR (100 MHz, CDCl$_3$) δ(ppm) 29.46, 30.57, 38.71, 57.07, 69.85, 75.19, 79.04, 126.67, 126.90, 128.54, 128.57, 128.63, 128.86, 141.87, 142.28.

Procedure K

Synthesis of Cis-(3S,6S)-3-azido-6-benzhydryl-tetrahydropyran 35a

Trans-(3R,6S)-6-diphenylmethyl-tetrahydropyran-3-yl methanesulfonate 34a (0.23 g, 0.68 mmol) in dry DMF (10 ml) was reacted with sodium azide (0.13 g, 2.03 mmol) to yield cis-(3S,6S)-3-azido-6-diphenylmethyl-tetrahydropyran, 35a, 0.17 g (86%, $[\alpha]_D$=(−)78.2, c=1, MeOH).

$^1$H NMR (400 MHz, CDCl$_3$) 1.38 (m, 1H, H-5) 1.60-1.84 (m, 2H, H-5, H-4) 1.98 (m, 1H, H-4), 3.55 (m, 1H, H-3), 3.63 (dd, J=2 Hz, 12.4 Hz, 1H, H-2) 3.98-4.12 (m, 3H, H-2, H-6, Ph$_2$CH) 7.16-7.40 (m, 10H, aromatic-CH). $^{13}$C NMR (100 MHz, CDCl$_3$) 25.47, 27.70, 55.60, 57.58, 69.79, 79.48, 126.58, 126.84, 128.59, 128.69, 128.76, 128.86 142.28 142.29.

Procedure L

Synthesis of Cis-(3S,6S)-(6-benzhydryl-tetrahydropyran-3-yl)-amine (36a)

Cis-(3S,6S)-3-azido-6-diphenylmethyl-tetrahydropyran 35a (0.17 g, 0.58 mmol) in methanol (25 ml) was hydrogenated employing as catalyst 10% Pd—C (0.017 g, 10% wt) for 4 hr to give cis-(3S,6S)-(6-diphenylmethyl-tetrahydropyran-3-yl)-amine 36a, 0.12 g (78%, $[\alpha]_D$=(−)74.3, c=1, MeOH).

$^1$H NMR (400 MHz, CD$_3$OD) 1.27 (m, 1H, H-5) 1.52 (m, 1H, H-5)1.62-1.80 (m, 2H, H-4) 2.78 (bs, 1H, H-3) 3.63 (m, 2H, H-2) 3.95 (d, J=8.8 Hz, 1H, Ph$_2$CH) 4.10 (dt, J=2 Hz, 9.6 Hz, 1H, H-6) 7.0-7.40 (m, 10H, aromatic-CH). $^{13}$C NMR (100 MHz, CDCl$_3$) 24.47, 29.29, 45.15, 57.32, 72.08, 79.28, 125.97, 126.34, 128.02, 128.39, 128.42 128.54 142.72 142.82.

Synthesis of Cis-(3R,6R)-(6-benzhydryl-tetrahydropyran-3-yl)-amine (34b)

Synthesis of Cis-(3R,6R)-3-azido-6-benzhydryl-tetrahydropyran

Trans-(3S,6R)-6-diphenylmethyl-tetrahydropyran-3-yl methanesulfonate (0.028 g, 0.082 mmol) was reacted with NaN$_3$ (0.016 g, 0.25 mmol) (Procedure L) to yield cis-(3R,6R)-3-azido-6-benzhydryl-tetrahydropyran 0.024 g (quantitative yield, $[\alpha]_D$=(+)77.6, c=1, MeOH).

$^1$H NMR (400 MHz, CDCl$_3$) 1.38 (m, 1H, H-5) 1.60-1.84 (m, 2H, H-5, H-4) 1.98 (m, 1H, H-4), 3.55 (m, 1H, H-3), 3.63 (dd, J=2 Hz, 12.4 Hz, 1H, H-2) 3.98-4.12 (m, 3H, H-2, H-6, Ph$_2$CH) 7.16-7.40 (m, 10H, aromatic-CH). $^{13}$C NMR (100 MHz, CDCl$_3$) 25.47, 27.70, 55.60, 57.58, 69.79, 79.48, 126.58, 126.84, 128.59, 128.69, 128.76, 128.86 142.28 142.29.

Cis-(3R,6R)-3-azido-6-diphenylmethyl-tetrahydropyran (0.024 g, 0.082 mmol) was hydrogenated (Procedure M) to yield cis-(3R,6R)-(6-benzhydryl-tetrahydropyran-3-yl)-amine 34b 0.02 g (92%, $[\alpha]_D$=(+)74.0, c=1, MeOH).

$^1$H NMR (400 MHz, CD$_3$OD) 1.27 (m, 1H, H-5) 1.52 (m, 1H, H-5)1.62-1.80 (m, 2H, H-4) 2.78 (bs, bs, 1H, H-3) 3.63 (m, 2H, H-2) 3.95 (d, J=8.8 Hz, 1H, Ph$_2$CH) 4.10 (dt, J=2 Hz, 9.6 Hz, 1H, H-6) 7.0-7.40 (m, 10H, aromatic-CH). $^{13}$C NMR (100 MHz, CDCl$_3$) 24.47, 29.29, 45.15, 57.32, 72.08, 79.28, 125.97, 126.34, 128.02, 128.39, 128.42 128.54 142.72 142.82.

Synthesis of cis-(3S,6S)-(6-benzhydryl-tetrahydropyran-3-yl)-(4-hydroxy-benzyl)-amine (−)37a Cis-(3S,6S)-3-amino-6-diphenylmethylpyran 36a (0.02 g, 0.075 mmol) was reacted with 4-hydroxybenzaldehyde (0.009 g, 0.075 mmol) in the presence of glacial acetic acid (0.005 g, 0.075 mmol) in 1,2-dichloroethane (10 ml), then was reduced by NaCNBH$_3$ (0.0057 g, 0.09 mmol) (Procedure H) to give cis-(3S,6S)-(6-benzhydryl-tetrahydropyran-3-yl)-(4-fluorobenzyl)-amine (−)-37a, 0.02 g (72%, $[\alpha]_D$=(−) 38.3, c=1, MeOH).

$^1$H NMR (400 MHz, CDCl$_3$) 1.36 (m, 1H, H-5) 1.51 (m, 1H, H-5)1.68 (m, 1H, H-4) 2.0 (m, 1H, H-4) 2.71 (s, 1H, H-3) 3.56 (dd, J=1.6 Hz, 11.6 Hz, 1H, H-2) 3.64 (m, 2H, (HO)Ph-CH) 3.96 (d, J=8.4 Hz, 1H, Ph$_2$CH) 4.02-4.16 (m, 2H, H-6, H-2) 6.52 (m, 2H, aromatic-CH) 6.98-7.38 (m, 12H, aromatic-CH). $^{13}$C NMR (100 MHz, CDCl$_3$) 25.28 27.31 50.39 50.68 57.21 69.88 79.45 116.04 126.56 126.67 128.54 128.70 128.73 128.93 129.86 130.47 142.16 142.58 155.93.

Free base (−)-37a was converted into the oxalate: mp 136-138° C. C, H, N Anal: [C$_{25}$H$_{27}$NO$_2$.(COOH)$_2$.0.6H$_2$O].

Synthesis of cis-(3R,6R)-(6-benzhydryl-tetrahydropyran-3-yl)-(4-hydroxy-benzyl)-amine (+)37a cis-(3R,6R)-3-amino-6-diphenylmethylpyran 34b (0.024 g, 0.09 mmol) was reacted with 4-hydroxybenzaldehyde (0.011 g, 0.09 mmol) in the presence of glacial acetic acid (0.0054 g, 0.09 mmol) in 1,2-dichloroethane (10 ml), then was reduced by NaCNBH$_3$ (0.012 g, 0.18 mmol) (Procedure H) to give cis-(3R,6R)-(6-benzhydryl-tetrahydropyran-3-yl)-(4-fluorobenzyl)-amine 0.024 g (+)-37a (71%, $[\alpha]_D$=(+) 40.1, c=, MeOH).

$^1$H NMR (400 MHz, CDCl$_3$) 1.34 (m, 1H, H-5) 1.51 (m, 1H, H-5)1.65 (m, 1H, H-4) 1.96 (m, 1H, H-4) 2.67 (m, 1H, H-3) 3.56 (dd, J=1.6 Hz, 11.6 Hz, 1H, H-2) 3.66 (m, 2H, (HO)Ph-CH$_2$) 3.96 (d, J=8.8 Hz, 1H, Ph$_2$CH)3.98-4.12 (m,

2H, H-6, H-2) 6.65 (m, 2H, aromatic-CH) 7.06-7.38 (m, 12H, aromatic-CH). $^{13}$C NMR (100 MHz, CDCl$_3$) 25.28 27.31 50.39 50.68 57.21 69.88 79.45 116.04 126.56 126.67 128.54 128.70 128.73 128.93 129.86 130.47 142.16 142.58 155.93.

Free base (+)-37a was converted into the oxalate: mp 136-138° C. C, H, N Anal: [C$_{25}$H$_{27}$NO$_2$.(COOH)$_2$.1.8H$_2$O].

TABLE 4

Affinity of Drugs at DAT, SERT, and NET in Rat Brain.

| Compound | DAT binding, IC$_{50}$, nM, [$^3$H]Win 35, 428$^a$ | DAT uptake, IC$_{50}$, nM [$^3$H]DA$^a$ | SERT uptake, IC$_{50}$, nM [$^3$H]5-HT$^a$ | NET uptake, IC$_{50}$, nM [$^3$H]NE$^a$ |
|---|---|---|---|---|
| GBR 12909$^b$ | 10.6 ± 1.9 | 14.2 ± 2.9 | 101.4 ± 14.2 | 114 ± 36 |
| (+)-29a | 182 ± 11 | 148 ± 22 | 745 ± 30 | 445 ± 39 |
| (+)-29g | 3750 ± 620 | 2670 ± 260 | 3810 ± 460 | 1840 ± 580 |
| (+)-29b | 1030 ± 120 | 440 ± 30 | 5560 ± 640 | 1130 ± 580 |
| (+)-29c | 443 ± 52 | 218 ± 20 | 2950 ± 380 | 77.3 ± 3.0 |
| (+)-29d | 596 ± 84 | 341 ± 43 | 6120 ± 730 | 770 ± 33 |
| (+)-29h | 1250 ± 100 | 962 ± 97 | 4420 ± 410 | 3220 ± 570 |
| (−)-29a | 226 ± 40 | 155 ± 16 | 28.9 ± 4.1 | 17.7 ± 5.9 |
| (−)-29g | 771 ± 86 | 822 ± 120 | 1070 ± 100 | 765 ± 34 |
| (−)-29b | 308 ± 25 | 169 ± 20 | 676 ± 33 | 13.3 ± 1.0 |
| (−)-29c | 1050 ± 40 | 427 ± 67 | 3570 ± 140 | 439 ± 14 |
| (−)-29d | 1860 ± 710 | 600 ± 79 | 862 ± 36 | 5.59 ± 1.05 |
| (−)-29h | 4640 ± 1030 | 2610 ± 140 | 10,000 ± 1400 | 336 ± 33 |
| (−)-29e | 1,060 ± 100 | 710 ± 130 | 24.0 ± 4.0 | 115 ± 14 |
| (−)-29f | 298 ± 29 | 135 ± 3 | 25.4 ± 2.0 | 108 ± 11 |
| (−)-32a | 289 ± 23 | 232 ± 28 | 265 ± 14 | 11.22 ± 1.01 |
| (−)-32b | 705 ± 176 | 162 ± 11 | 18.7 ± 1.6 | 2.42 ± 0.47 |
| (+)-32a | 155 ± 6 | 123 ± 10 | 2833 ± 480 | 102 ± 20 |
| (+)-32b | 494 ± 96 | 247 ± 21 | 272 ± 55 | 15.0 ± 4.5 |
| (−)-37a | 280 ± 8 | 114 ± 8 | 42 ± 3 | 5.5 ± 0.1 |
| (−)-37b | | | | |
| (+)-37a | 141 ± 2.2 | 90.7 ± 4 | 209 ± 25 | 45.6 ± 6 |
| (+)-37b | | | | |

TABLE 5

Affinity of Drugs at Dopamine, Serotonin, and Norepinephrine Transporters in Rat Striatum

| Compound | DAT binding, IC$_{50}$, nM, [$^3$H]Win 35, 428$^a$ | SERT binding, IC$_{50}$, nM [$^3$H]citalopram$^a$ | NET binding, IC$_{50}$, nM [$^3$H]nisoxetine$^a$ | DAT uptake, IC$_{50}$, nM [$^3$H]DA$^a$ |
|---|---|---|---|---|
| Cocaine | 266 ± 37 | 737 ± 160 | 3,130 ± 550 | |
| GBR 12909 | 10.6 ± 1.9 | 132 ± 0 | 496 ± 22 | |
| 48 | 80.4 ± 17.4 | >10,000 | 1328 ± 592 | 104 ± 49 |
| 52 | 162 ± 19 | >10,000 | 1435 ± | 165 ± 17 |
| 57 | 398 ± 33 | 4400 | 3432 ± 1752 | 215 ± 14 |
| 63 | 420 ± 38 | 1491 ± 134$^b$ | 1486 ± 443$^b$ | 158 ± 28 |
| 64 | 296 ± 42 | 2441 ± 188 | 255 ± 52 | |

$^b$Uptake inhibition values

The most widely accepted basis of the cause of depression focuses on monoamines. Imbalances in the level of dopamine (DA), serotonin (5-HT) and norepinephrine (NE) neurotransmitter systems are responsible for such neurodegeneration. Clinical studies as well as basic research in neurobiology has demonstrated that two monoaminergic systems are involved in the etiology and therapy of affective disorders, namely serotonin and norepinephrine. The common basis of pharmacotherapy is based on the increase of intracellular concentration of serotonin and norepinephrine by blocking the reuptake mechanism of serotonin and norepinephrine transporters. It is evident from Table 4 that the compounds (−)-29a, (−)-29e, (−)-29f, (−)-32b and (−)-37a are potent blockers for both SERT and NET. Compounds with such properties are known as SNRI and are potent antidepressants. The known antidepressant drugs belonging to this SNRI category and used in the clinics are venlafaxine, milnacipran, chlorimipramine and duloxetine. SNRI are considered to have faster onset of action compared to SSRI and are more effective to treat depression. On the other hand, compounds (−)-29b, (−)-29d, (−)-32a, (+)-32a and (+)-37a are selective blockers for NET. Compounds with such biological-property are known as NRI and are also considered potent antidepressants. A known potent NRI which was recently approved for antidepressant treatment, is Reboxetine.

Current existing SNRI, SSRI and RNI are also being used in other related neurodisorders including post-traumatic stress disorder, social phobia, obsessive compulsive disorders, anxiety and urinary stress incontinence. For this reason the compounds included in this application will also have use in neurodisorders like post-traumatic stress disorder, social phobia, obsessive compulsive disorders, anxiety and urinary stress incontinence.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:
1. A compound having formula X:

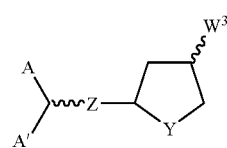

or a pharmaceutically acceptable salt thereof, wherein:
A and A' are individually selected from the group of optionally substituted C$_4$-C$_{14}$ aryl and heteroaryl wherein heteroatoms of heteroaryl A and/or A' are selected from the group consisting of O, N, and S;
Z is a chemical bond or —Y—(CH$_2$)$_o$;
Y is NH or O;
o is 0, 1, 2, 3, or 4;
and
W$^3$ is an alkyl amine or an aryl amine.
2. The compound of claim 1 having formula:

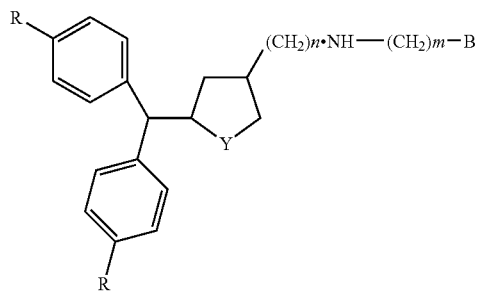

-continued

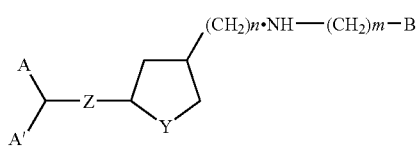
XIb or a pharmaceutically acceptable salt thereof, wherein:
m and n are 0-4;
Z is a chemical bond or —Y—(CH$_2$)$_o$—;
Y is NH or O;
o is 0, 1, 2, 3, or 4;
at least one of A and A' are selected from the group consisting of:

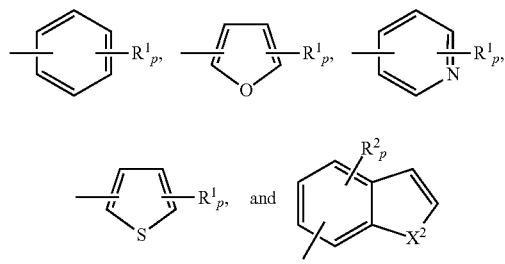

p is 0-6;
R$^1$ is C$_{1-4}$ alkyl, C$_{2-6}$ alkenyl, C$_{2-6}$ optionally halogenated alkynyl, C$_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or —OR$^8$;
R$^2$ has the meaning of R$^1$ or a 5 or 6 membered heterocycle containing 1 or more heteroatoms selected from the group consisting of N, O, and S;
X$^2$ is N, O, or S;
R$^4$ is H, C$_{1-18}$ alkyl, C$_{5-10}$ cycloalkyl, or C$_{2-18}$ alkylene;
R$^8$ is C$_{1-8}$ alkyl, C$_{5-6}$ cycloalkyl, C$_{2-8}$ alkenyl, or a 5 or 6-member aromatic ring including heterocyclic rings;
B is selected from the group consisting of:

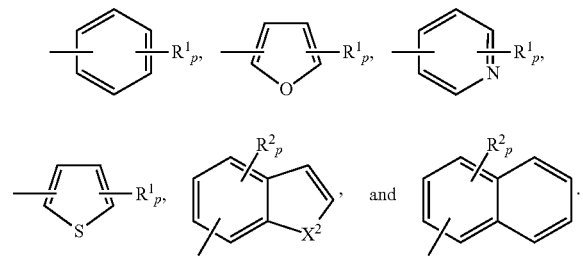

3. The compound of claim 1 having formula:

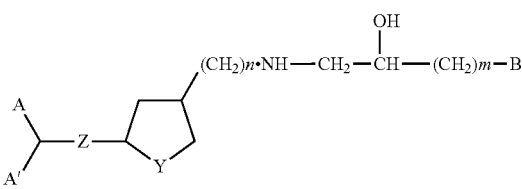

or a pharmaceutically acceptable salt thereof, wherein:
m and n are 0-4;
Z is selected from the group consisting of a chemical bond and —Y—(CH$_2$)$_o$;
Y is NH or O;
o is 0, 1, 2, 3, or 4;
at least one of A and A' are selected from the group consisting of:

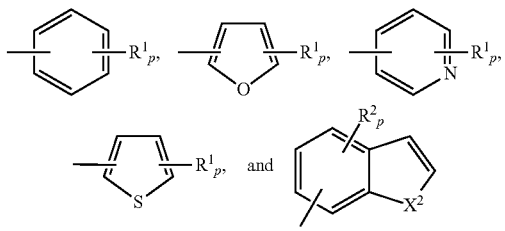

p is 0-6;
R$^1$ is C$_{1-4}$ alkyl, C$_{2-6}$ alkenyl, C$_{2-6}$ optionally halogenated alkynyl, C$_{2-6}$ hydroxyalkynyl, halo, —CN, —COOR$^4$, —OH, —NO$_2$, —NH$_2$, —NHR$^4$, —SO$_2$NH$_2$, —NHSO$_2$R$^8$, —OCF$_3$, or -Ole;
R$^2$ has the meaning of R$^1$ or a 5 or 6 membered heterocycle containing 1 or more heteroatoms selected from the group consisting of N, O, and S;
X$^2$ is N, O, or S;
R$^4$ is H, C$_{1-18}$ alkyl, C$_{5-10}$ cycloalkyl, or C$_{2-18}$ alkylene; and
R$^8$ is C$_{1-8}$ alkyl, C$_{5-6}$ cycloalkyl, C$_{2-8}$ alkenyl, or a 5 or 6-member aromatic ring including heterocyclic rings; and
B is selected from the group consisting of:

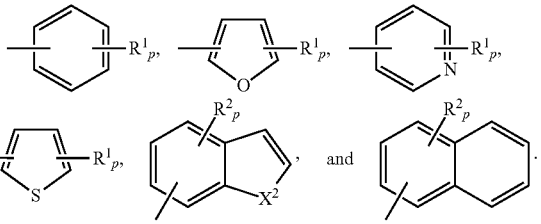

\* \* \* \* \*